United States Patent
Meess et al.

(10) Patent No.: US 10,913,125 B2
(45) Date of Patent: Feb. 9, 2021

(54) WELDING SYSTEM PROVIDING VISUAL AND AUDIO CUES TO A WELDING HELMET WITH A DISPLAY

(71) Applicant: LINCOLN GLOBAL, INC., Santa Fe Springs, CA (US)

(72) Inventors: Brian Meess, Cleveland, OH (US); Sarah Evans, Garrettsville, OH (US)

(73) Assignee: LINCOLN GLOBAL, INC., Santa Fe Springs, CA (US)

( * ) Notice: Subject to any disclaimer, the term of this patent is extended or adjusted under 35 U.S.C. 154(b) by 178 days.

(21) Appl. No.: 15/785,489

(22) Filed: Oct. 17, 2017

(65) Prior Publication Data

US 2018/0126476 A1    May 10, 2018

Related U.S. Application Data

(60) Provisional application No. 62/418,737, filed on Nov. 7, 2016.

(51) Int. Cl.
*B23K 9/095* (2006.01)
*A61F 9/06* (2006.01)
(Continued)

(52) U.S. Cl.
CPC .............. *B23K 9/0953* (2013.01); *A61F 9/06* (2013.01); *A61F 9/064* (2013.01); *B23K 9/0956* (2013.01);
(Continued)

(58) Field of Classification Search
CPC .... B23K 9/0953; B23K 9/1087; B23K 9/322; B23K 9/0956; A61F 9/064; A61F 9/06; G08B 3/10; G06T 11/60; G06K 9/00671; G09B 19/24; G02B 2027/0138; G02B 2027/0141; G02B 2027/014;
(Continued)

(56) References Cited

U.S. PATENT DOCUMENTS

| 317,063 A | 5/1885 | Wittenstrom |
| 428,459 A | 5/1890 | Coffin |

(Continued)

FOREIGN PATENT DOCUMENTS

| CA | 2698078 A1 | 9/2011 |
| CN | 101193723 A | 6/2008 |

(Continued)

OTHER PUBLICATIONS

The Lincoln Electric Company, Check Point Operator's Manual, 188 pages, issue date Aug. 2015.
(Continued)

*Primary Examiner* — Charles R Kasenge
(74) *Attorney, Agent, or Firm* — David J. Muzilla

(57) ABSTRACT

A system for aiding a user in at least one of welding, cutting, joining, and cladding operations is provided. The system includes a welding tool and a welding helmet with a face-mounted display. The system also includes a spatial tracker configured to track the welding helmet and the welding tool in 3-D space relative to an object to be worked on. A processor based subsystem is configured to generate visual cues based on information from the spatial tracker and transmit the visual cues to a predetermined location on the face-mounted display.

31 Claims, 25 Drawing Sheets

(51) Int. Cl.

| | |
|---|---|
| *G02B 27/01* | (2006.01) |
| *G05B 19/18* | (2006.01) |
| *G08B 3/10* | (2006.01) |
| *G06T 11/60* | (2006.01) |
| *G06K 9/00* | (2006.01) |
| *G09B 19/24* | (2006.01) |
| *B23K 9/10* | (2006.01) |
| *B23K 9/32* | (2006.01) |
| *G06F 3/0482* | (2013.01) |

(52) U.S. Cl.
CPC ............ *B23K 9/1087* (2013.01); *B23K 9/322* (2013.01); *G02B 27/0172* (2013.01); *G05B 19/182* (2013.01); *G06K 9/00671* (2013.01); *G06T 11/60* (2013.01); *G08B 3/10* (2013.01); *G09B 19/24* (2013.01); *G02B 2027/014* (2013.01); *G02B 2027/0138* (2013.01); *G02B 2027/0141* (2013.01); *G05B 2219/45044* (2013.01); *G05B 2219/45135* (2013.01); *G06F 3/0482* (2013.01)

(58) Field of Classification Search
CPC .............. G02B 27/0172; G06F 3/0482; G05B 2219/45044; G05B 2219/45135; G05B 19/182

See application file for complete search history.

(56) References Cited

U.S. PATENT DOCUMENTS

| | | |
|---|---|---|
| 483,428 A | 9/1892 | Coffin |
| 1,159,119 A | 11/1915 | Springer |
| D140,630 S | 3/1945 | Garibay |
| D142,377 S | 9/1945 | Dunn |
| D152,049 S | 12/1948 | Welch, Jr. |
| 2,681,969 A | 6/1954 | Burke |
| D174,208 S | 3/1955 | Abildgaard |
| 2,728,838 A | 12/1955 | Barnes |
| D176,942 S | 2/1956 | Cross |
| 2,894,086 A | 7/1959 | Rizer |
| 3,035,155 A | 5/1962 | Hawk |
| 3,059,519 A | 10/1962 | Stanton |
| 3,356,823 A | 12/1967 | Waters et al. |
| 3,555,239 A | 1/1971 | Kerth |
| 3,621,177 A | 11/1971 | McPherson et al. |
| 3,654,421 A | 4/1972 | Streetman et al. |
| 3,739,140 A | 6/1973 | Rotilio |
| 3,866,011 A | 2/1975 | Cole |
| 3,867,769 A | 2/1975 | Schow et al. |
| 3,904,845 A | 9/1975 | Minkiewicz |
| 3,988,913 A | 11/1976 | Metcalfe et al. |
| D243,459 S | 2/1977 | Bliss |
| 4,024,371 A | 5/1977 | Drake |
| 4,041,615 A | 8/1977 | Whitehill |
| D247,421 S | 3/1978 | Driscoll |
| 4,124,944 A | 11/1978 | Blair |
| 4,132,014 A | 1/1979 | Schow |
| 4,237,365 A | 12/1980 | Lambros et al. |
| 4,275,266 A | 6/1981 | Laser |
| 4,280,041 A | 7/1981 | Kiessling et al. |
| 4,280,042 A | 7/1981 | Berger et al. |
| 4,280,137 A | 7/1981 | Ashida et al. |
| 4,314,125 A | 2/1982 | Nakamura |
| 4,354,087 A | 10/1982 | Osterlitz |
| 4,359,622 A | 11/1982 | Dostoomian et al. |
| 4,375,026 A | 2/1983 | Kearney |
| 4,410,787 A | 10/1983 | Kremers et al. |
| 4,429,266 A | 1/1984 | Tradt |
| 4,452,589 A | 6/1984 | Denison |
| D275,292 S | 8/1984 | Bouman |
| D277,761 S | 2/1985 | Korovin et al. |
| 4,523,808 A | 6/1985 | Miller |
| 4,525,619 A | 6/1985 | Ide et al. |
| D280,329 S | 8/1985 | Bouman |
| 4,611,111 A | 9/1986 | Baheti et al. |
| 4,616,326 A | 10/1986 | Meier et al. |
| 4,629,860 A | 12/1986 | Lindbom |
| 4,641,282 A | 2/1987 | Ounuma |
| 4,677,277 A | 6/1987 | Cook et al. |
| 4,680,014 A | 7/1987 | Paton et al. |
| 4,689,021 A | 8/1987 | Vasiliev et al. |
| 4,707,582 A | 11/1987 | Beyer |
| 4,716,273 A | 12/1987 | Paton et al. |
| D297,704 S | 9/1988 | Bulow |
| 4,867,685 A | 9/1989 | Brush et al. |
| 4,877,940 A | 10/1989 | Bangs et al. |
| 4,897,521 A | 1/1990 | Burr |
| 4,907,973 A | 3/1990 | Hon |
| 4,931,018 A | 6/1990 | Herbst |
| 4,973,814 A | 11/1990 | Kojima et al. |
| 4,998,050 A | 3/1991 | Nishiyama et al. |
| 5,034,593 A | 7/1991 | Rice et al. |
| 5,061,841 A | 10/1991 | Richardson |
| 5,089,914 A | 2/1992 | Prescott |
| 5,192,845 A | 3/1993 | Kirmsse et al. |
| 5,206,472 A | 4/1993 | Myking et al. |
| 5,266,930 A | 11/1993 | Ichikawa et al. |
| 5,285,916 A | 2/1994 | Ross |
| 5,305,183 A | 4/1994 | Teynor |
| 5,320,538 A | 6/1994 | Baum |
| 5,337,611 A | 8/1994 | Fleming et al. |
| 5,360,156 A | 11/1994 | Ishizaka et al. |
| 5,360,960 A | 11/1994 | Shirk |
| 5,370,071 A | 12/1994 | Ackermann |
| D359,296 S | 6/1995 | Witherspoon |
| 5,424,634 A | 6/1995 | Goldfarb et al. |
| 5,436,638 A | 7/1995 | Bolas et al. |
| 5,464,957 A | 11/1995 | Kidwell et al. |
| D365,583 S | 12/1995 | Viken |
| 5,562,843 A | 10/1996 | Yasumoto |
| 5,662,822 A | 9/1997 | Tada |
| 5,670,071 A | 9/1997 | Ueyama et al. |
| 5,671,158 A | 9/1997 | Fournier |
| 5,676,503 A | 10/1997 | Lang |
| 5,676,867 A | 10/1997 | Van Allen |
| 5,708,253 A | 1/1998 | Bloch et al. |
| 5,710,405 A | 1/1998 | Solomon et al. |
| 5,719,369 A | 2/1998 | White et al. |
| D392,534 S | 3/1998 | Degen et al. |
| 5,728,991 A | 3/1998 | Takada et al. |
| 5,734,421 A | 3/1998 | Maguire, Jr. |
| 5,751,258 A | 5/1998 | Fergason et al. |
| D395,296 S | 6/1998 | Kaye et al. |
| D396,238 S | 7/1998 | Schmitt |
| 5,781,258 A | 7/1998 | Dabral et al. |
| 5,823,785 A | 10/1998 | Matherne, Jr. |
| 5,835,077 A | 11/1998 | Dao et al. |
| 5,835,277 A | 11/1998 | Hegg |
| 5,845,053 A | 12/1998 | Watanabe et al. |
| 5,877,777 A | 3/1999 | Colwell |
| 5,896,579 A | 4/1999 | Johnson |
| 5,916,464 A | 6/1999 | Geiger |
| 5,963,891 A | 10/1999 | Walker et al. |
| 6,008,470 A | 12/1999 | Zhang et al. |
| 6,037,948 A | 3/2000 | Liepa |
| 6,049,059 A | 4/2000 | Kim |
| 6,051,805 A | 4/2000 | Vaidya et al. |
| 6,114,645 A | 9/2000 | Burgess |
| 6,155,475 A | 12/2000 | Ekelof et al. |
| 6,155,928 A | 12/2000 | Burdick |
| 6,230,327 B1 | 5/2001 | Briand |
| 6,236,013 B1 | 5/2001 | Delzenne |
| 6,236,017 B1 | 5/2001 | Smartt et al. |
| 6,242,711 B1 | 6/2001 | Cooper |
| 6,271,500 B1 | 8/2001 | Hirayama et al. |
| 6,330,938 B1 | 12/2001 | Herve et al. |
| 6,330,966 B1 | 12/2001 | Eissfeller |
| 6,331,848 B1 | 12/2001 | Stove et al. |
| D456,428 S | 4/2002 | Aronson, II et al. |
| 6,373,465 B2 | 4/2002 | Jolly et al. |
| D456,828 S | 5/2002 | Aronson, II et al. |
| 6,397,186 B1 | 5/2002 | Bush |

(56) References Cited

U.S. PATENT DOCUMENTS

| | | |
|---|---|---|
| D461,383 S | 8/2002 | Blackburn |
| 6,441,342 B1 | 8/2002 | Hsu |
| 6,445,964 B1 | 9/2002 | White et al. |
| 6,492,618 B1 | 12/2002 | Flood et al. |
| 6,506,997 B2 | 1/2003 | Matsuyama |
| 6,552,303 B1 | 4/2003 | Blankenship et al. |
| 6,560,029 B1 | 5/2003 | Dobbie et al. |
| 6,563,489 B1 | 5/2003 | Latypov et al. |
| 6,568,846 B1 | 5/2003 | Cote et al. |
| D475,726 S | 6/2003 | Suga et al. |
| 6,572,379 B1 | 6/2003 | Sears et al. |
| 6,583,386 B1 | 6/2003 | Ivkovich |
| 6,621,049 B2 | 9/2003 | Suzuki |
| 6,624,388 B1 | 9/2003 | Blankenship et al. |
| D482,171 S | 11/2003 | Vui et al. |
| 6,647,288 B2 | 11/2003 | Madill et al. |
| 6,649,858 B2 | 11/2003 | Wakeman |
| 6,655,645 B1 | 12/2003 | Lu et al. |
| 6,660,965 B2 | 12/2003 | Simpson |
| 6,697,701 B2 | 2/2004 | Hillen et al. |
| 6,697,770 B1 | 2/2004 | Nagetgaal |
| 6,703,585 B2 | 3/2004 | Suzuki |
| 6,708,385 B1 | 3/2004 | Lemelson |
| 6,710,298 B2 | 3/2004 | Eriksson |
| 6,710,299 B2 | 3/2004 | Blankenship et al. |
| 6,715,502 B1 | 4/2004 | Rome et al. |
| 6,720,878 B2 | 4/2004 | Jumpertz |
| D490,347 S | 5/2004 | Meyers |
| 6,730,875 B2 | 5/2004 | Hsu |
| 6,734,393 B1 | 5/2004 | Friedl et al. |
| 6,744,011 B1 | 6/2004 | Hu et al. |
| 6,750,428 B2 | 6/2004 | Okamoto et al. |
| 6,765,584 B1 | 7/2004 | Wloka et al. |
| 6,768,974 B1 | 7/2004 | Nanjundan et al. |
| 6,772,802 B2 | 8/2004 | Few |
| 6,788,442 B1 | 9/2004 | Potin et al. |
| 6,795,778 B2 | 9/2004 | Dodge et al. |
| 6,798,974 B1 | 9/2004 | Nakano et al. |
| 6,857,553 B1 | 2/2005 | Hartman et al. |
| 6,858,817 B2 | 2/2005 | Blankenship et al. |
| 6,865,926 B2 | 3/2005 | O'Brien et al. |
| 6,871,958 B2 | 3/2005 | Christensen |
| D504,449 S | 4/2005 | Butchko |
| 6,920,371 B2 | 7/2005 | Hillen et al. |
| 6,940,037 B1 | 9/2005 | Kovacevic et al. |
| 6,940,039 B2 | 9/2005 | Blankenship et al. |
| 7,021,937 B2 | 4/2006 | Simpson et al. |
| 7,024,342 B1 | 4/2006 | Waite et al. |
| 7,126,078 B2 | 10/2006 | Demers et al. |
| 7,132,617 B2 | 11/2006 | Lee et al. |
| 7,170,032 B2 | 1/2007 | Flood |
| 7,194,447 B2 | 3/2007 | Harvey et al. |
| 7,247,814 B2 | 7/2007 | Ott |
| D555,446 S | 11/2007 | Picaza Ibarrondo et al. |
| 7,315,241 B1 | 1/2008 | Daily et al. |
| D561,973 S | 2/2008 | Kinsley et al. |
| 7,346,972 B2 | 3/2008 | Inget |
| 7,353,715 B2 | 4/2008 | Myers |
| 7,363,137 B2 | 4/2008 | Brant et al. |
| 7,375,304 B2 | 5/2008 | Kainec et al. |
| 7,381,923 B2 | 6/2008 | Gordon et al. |
| 7,414,595 B1 | 8/2008 | Muffler |
| 7,465,230 B2 | 12/2008 | LeMay et al. |
| 7,478,108 B2 | 1/2009 | Townsend et al. |
| D587,975 S | 3/2009 | Aronson, II et al. |
| 7,516,022 B2 | 4/2009 | Lee et al. |
| 7,557,327 B2 | 7/2009 | Matthews |
| 7,580,821 B2 | 8/2009 | Schirm et al. |
| D602,057 S | 10/2009 | Osicki |
| 7,621,171 B2 | 11/2009 | O'Brien |
| D606,102 S | 12/2009 | Bender et al. |
| 7,643,890 B1 | 1/2010 | Hillen et al. |
| 7,687,741 B2 | 3/2010 | Kainec et al. |
| D614,217 S | 4/2010 | Peters et al. |
| D615,573 S | 5/2010 | Peters et al. |
| 7,817,162 B2 | 10/2010 | Bolick et al. |
| 7,853,645 B2 | 12/2010 | Brown et al. |
| D631,074 S | 1/2011 | Peters et al. |
| 7,874,921 B2 | 1/2011 | Baszucki et al. |
| 7,926,228 B1 | 4/2011 | Becker |
| 7,970,172 B1 | 6/2011 | Hendrickson |
| 7,972,129 B2 | 7/2011 | O'Donoghue |
| 7,991,587 B2 | 8/2011 | Ihn |
| 8,069,017 B2 | 11/2011 | Hallquist |
| 8,224,881 B1 | 7/2012 | Spear et al. |
| 8,248,324 B2 | 8/2012 | Nangle |
| 8,265,886 B2 | 9/2012 | Bisiaux et al. |
| 8,274,013 B2 | 9/2012 | Wallace |
| 8,287,522 B2 | 10/2012 | Moses et al. |
| 8,316,462 B2 | 11/2012 | Becker |
| 8,363,048 B2 | 1/2013 | Gering |
| 8,365,603 B2 | 2/2013 | Lesage et al. |
| 8,512,043 B2 | 8/2013 | Choquet |
| 8,569,646 B2 | 10/2013 | Daniel et al. |
| 8,657,605 B2 | 2/2014 | Wallace |
| 8,680,434 B2 | 3/2014 | Stoger et al. |
| 8,747,116 B2 | 6/2014 | Zboray et al. |
| 8,777,629 B2 | 7/2014 | Kreindl et al. |
| RE45,062 E | 8/2014 | Maguire, Jr. |
| 8,851,896 B2 | 10/2014 | Wallace |
| 8,860,760 B2 | 10/2014 | Chen |
| 8,915,740 B2 | 12/2014 | Zboray |
| RE45,398 E | 3/2015 | Wallace |
| 8,992,226 B1 | 3/2015 | Leach et al. |
| 9,011,154 B2 | 4/2015 | Kindig |
| 9,293,056 B2 | 3/2016 | Zboray et al. |
| 9,293,057 B2 | 3/2016 | Zboray et al. |
| 9,318,026 B2 | 4/2016 | Peters |
| 9,323,056 B2 | 4/2016 | Williams |
| 9,522,437 B2 | 12/2016 | Pfeifer |
| 9,761,153 B2 | 9/2017 | Zboray et al. |
| 9,767,712 B2 | 9/2017 | Postlethwaite |
| 9,779,636 B2 | 10/2017 | Zboray et al. |
| 9,818,312 B2 | 11/2017 | Zboray et al. |
| 9,836,994 B2 | 12/2017 | Kindig et al. |
| 9,911,359 B2 | 3/2018 | Wallace |
| 9,911,360 B2 | 3/2018 | Wallace |
| 9,928,755 B2 | 3/2018 | Wallace et al. |
| 2001/0045808 A1 | 11/2001 | Hietmann et al. |
| 2001/0052893 A1 | 12/2001 | Jolly et al. |
| 2002/0032553 A1 | 3/2002 | Simpson et al. |
| 2002/0046999 A1 | 4/2002 | Veikkolainen et al. |
| 2002/0050984 A1 | 5/2002 | Roberts |
| 2002/0085843 A1 | 7/2002 | Mann |
| 2002/0175897 A1 | 11/2002 | Pelosi |
| 2003/0000931 A1 | 1/2003 | Ueda et al. |
| 2003/0025884 A1 | 2/2003 | Hamana et al. |
| 2003/0069866 A1 | 4/2003 | Ohno |
| 2003/0075534 A1 | 4/2003 | Okamoto et al. |
| 2003/0106787 A1 | 6/2003 | Santilli |
| 2003/0111451 A1 | 6/2003 | Blankenship et al. |
| 2003/0172032 A1 | 9/2003 | Choquet |
| 2003/0186199 A1 | 10/2003 | McCool et al. |
| 2003/0206491 A1 | 11/2003 | Pacheco |
| 2003/0223592 A1 | 12/2003 | Deruginsky et al. |
| 2003/0234885 A1 | 12/2003 | Pilu |
| 2004/0020907 A1 | 2/2004 | Zauner et al. |
| 2004/0035990 A1 | 2/2004 | Ackeret |
| 2004/0050824 A1 | 3/2004 | Samler |
| 2004/0088071 A1 | 5/2004 | Kouno et al. |
| 2004/0140301 A1 | 7/2004 | Blankenship et al. |
| 2004/0181382 A1 | 9/2004 | Hu et al. |
| 2004/0217096 A1 | 11/2004 | Lipnevicius |
| 2005/0007504 A1 | 1/2005 | Fergason |
| 2005/0017152 A1 | 1/2005 | Fergason |
| 2005/0029326 A1 | 2/2005 | Henrickson |
| 2005/0046584 A1 | 3/2005 | Breed |
| 2005/0050168 A1 | 3/2005 | Wen et al. |
| 2005/0101767 A1 | 5/2005 | Clapham et al. |
| 2005/0103766 A1 | 5/2005 | Iizuka et al. |
| 2005/0103767 A1 | 5/2005 | Kainec et al. |
| 2005/0109735 A1 | 5/2005 | Flood |
| 2005/0128186 A1 | 6/2005 | Shahoian et al. |
| 2005/0133488 A1 | 6/2005 | Blankenship et al. |

(56) References Cited

U.S. PATENT DOCUMENTS

| | | |
|---|---|---|
| 2005/0159840 A1 | 7/2005 | Lin et al. |
| 2005/0163364 A1 | 7/2005 | Beck et al. |
| 2005/0189336 A1 | 9/2005 | Ku |
| 2005/0199602 A1 | 9/2005 | Kaddani et al. |
| 2005/0230573 A1 | 10/2005 | Ligertwood |
| 2005/0252897 A1 | 11/2005 | Hsu et al. |
| 2005/0275913 A1 | 12/2005 | Vesely et al. |
| 2005/0275914 A1 | 12/2005 | Vesely et al. |
| 2006/0014130 A1 | 1/2006 | Weinstein |
| 2006/0076321 A1 | 4/2006 | Maev et al. |
| 2006/0136183 A1 | 6/2006 | Choquet |
| 2006/0142656 A1 | 6/2006 | Malackowski et al. |
| 2006/0154226 A1 | 7/2006 | Maxfield |
| 2006/0163227 A1 | 7/2006 | Hillen et al. |
| 2006/0166174 A1 | 7/2006 | Rowe et al. |
| 2006/0169682 A1 | 8/2006 | Kainec et al. |
| 2006/0173619 A1 | 8/2006 | Brant et al. |
| 2006/0189260 A1 | 8/2006 | Sung |
| 2006/0207980 A1 | 9/2006 | Jacovetty et al. |
| 2006/0213892 A1 | 9/2006 | Ott |
| 2006/0214924 A1 | 9/2006 | Kawamoto et al. |
| 2006/0226137 A1 | 10/2006 | Huismann et al. |
| 2006/0252543 A1 | 11/2006 | Van Noland et al. |
| 2006/0258447 A1 | 11/2006 | Baszucki et al. |
| 2007/0034611 A1 | 2/2007 | Drius et al. |
| 2007/0038400 A1 | 2/2007 | Lee et al. |
| 2007/0045488 A1 | 3/2007 | Shin |
| 2007/0088536 A1 | 4/2007 | Ishikawa |
| 2007/0112889 A1 | 5/2007 | Cook et al. |
| 2007/0198117 A1 | 8/2007 | Wajihuddin |
| 2007/0209586 A1 | 9/2007 | Ebensberger et al. |
| 2007/0211026 A1 | 9/2007 | Ohta |
| 2007/0221797 A1 | 9/2007 | Thompson et al. |
| 2007/0256503 A1 | 11/2007 | Wong et al. |
| 2007/0277611 A1 | 12/2007 | Portzgen et al. |
| 2007/0291035 A1 | 12/2007 | Vesely et al. |
| 2008/0021311 A1 | 1/2008 | Goldbach |
| 2008/0031774 A1 | 2/2008 | Magnant et al. |
| 2008/0038702 A1 | 2/2008 | Choquet |
| 2008/0061113 A9 | 3/2008 | Seki et al. |
| 2008/0078811 A1 | 4/2008 | Hillen et al. |
| 2008/0078812 A1 | 4/2008 | Peters et al. |
| 2008/0117203 A1 | 5/2008 | Gering |
| 2008/0120075 A1 | 5/2008 | Wloka |
| 2008/0128398 A1 | 6/2008 | Schneider |
| 2008/0135533 A1 | 6/2008 | Ertmer et al. |
| 2008/0140815 A1 | 6/2008 | Brant et al. |
| 2008/0149686 A1 | 6/2008 | Daniel et al. |
| 2008/0203075 A1 | 8/2008 | Feldhausen et al. |
| 2008/0233550 A1 | 9/2008 | Solomon |
| 2008/0303197 A1 | 12/2008 | Paquette et al. |
| 2008/0314887 A1 | 12/2008 | Stoger et al. |
| 2009/0015585 A1 | 1/2009 | Klusza |
| 2009/0021514 A1 | 1/2009 | Klusza |
| 2009/0045183 A1 | 2/2009 | Artelsmair et al. |
| 2009/0050612 A1 | 2/2009 | Serruys |
| 2009/0057286 A1 | 3/2009 | Ihara et al. |
| 2009/0152251 A1 | 6/2009 | Dantinne et al. |
| 2009/0173726 A1 | 7/2009 | Davidson et al. |
| 2009/0184098 A1 | 7/2009 | Daniel et al. |
| 2009/0200281 A1 | 8/2009 | Hampton |
| 2009/0200282 A1 | 8/2009 | Hampton |
| 2009/0231423 A1 | 9/2009 | Becker et al. |
| 2009/0259444 A1 | 10/2009 | Dolansky et al. |
| 2009/0298024 A1 | 12/2009 | Batzler et al. |
| 2009/0325699 A1 | 12/2009 | Delgiannidis |
| 2010/0012017 A1 | 1/2010 | Miller |
| 2010/0012637 A1 | 1/2010 | Jaeger |
| 2010/0048273 A1 | 2/2010 | Wallace et al. |
| 2010/0062405 A1 | 3/2010 | Zboray et al. |
| 2010/0062406 A1 | 3/2010 | Zboray |
| 2010/0096373 A1 | 4/2010 | Hillen et al. |
| 2010/0121472 A1 | 5/2010 | Babu et al. |
| 2010/0133247 A1 | 6/2010 | Mazumder et al. |
| 2010/0133250 A1 | 6/2010 | Sardy et al. |
| 2010/0176107 A1 | 7/2010 | Bong |
| 2010/0201803 A1 | 8/2010 | Melikian |
| 2010/0223706 A1 | 9/2010 | Becker |
| 2010/0224610 A1 | 9/2010 | Wallace |
| 2010/0276396 A1 | 11/2010 | Cooper et al. |
| 2010/0299101 A1 | 11/2010 | Shimada et al. |
| 2010/0307249 A1 | 12/2010 | Lesage et al. |
| 2011/0006047 A1 | 1/2011 | Penrod et al. |
| 2011/0060568 A1 | 3/2011 | Goldline et al. |
| 2011/0091846 A1 | 4/2011 | Kreindl et al. |
| 2011/0114615 A1 | 5/2011 | Daniel et al. |
| 2011/0116076 A1 | 5/2011 | Chantry et al. |
| 2011/0117527 A1 | 5/2011 | Conrardy et al. |
| 2011/0122495 A1 | 5/2011 | Togashi |
| 2011/0183304 A1 | 7/2011 | Wallace et al. |
| 2011/0187746 A1 | 8/2011 | Suto et al. |
| 2011/0248864 A1 | 10/2011 | Becker et al. |
| 2011/0290765 A1 | 12/2011 | Albrecht et al. |
| 2011/0316516 A1 | 12/2011 | Schiefermuller et al. |
| 2012/0122062 A1 | 5/2012 | Yang et al. |
| 2012/0189993 A1 | 7/2012 | Kindig et al. |
| 2012/0291172 A1 | 11/2012 | Wills et al. |
| 2012/0298640 A1 | 11/2012 | Conrardy et al. |
| 2013/0026150 A1 | 1/2013 | Chantry et al. |
| 2013/0040270 A1 | 2/2013 | Albrecht |
| 2013/0049976 A1 | 2/2013 | Maggiore |
| 2013/0075380 A1 | 3/2013 | Albrech et al. |
| 2013/0182070 A1 | 7/2013 | Peters et al. |
| 2013/0183645 A1 | 7/2013 | Wallace et al. |
| 2013/0189657 A1 | 7/2013 | Wallace et al. |
| 2013/0189658 A1 | 7/2013 | Peters et al. |
| 2013/0206741 A1* | 8/2013 | Pfeifer .............. B23K 9/095 219/130.01 |
| 2013/0209976 A1 | 8/2013 | Postlethwaite et al. |
| 2013/0230832 A1 | 9/2013 | Peters et al. |
| 2013/0231980 A1 | 9/2013 | Elgart et al. |
| 2013/0327747 A1 | 12/2013 | Dantinne et al. |
| 2014/0013478 A1* | 1/2014 | Cole .............. A61F 9/06 2/8.2 |
| 2014/0017642 A1 | 1/2014 | Postlethwaite |
| 2014/0038143 A1 | 2/2014 | Daniel et al. |
| 2014/0065584 A1 | 3/2014 | Wallace et al. |
| 2014/0134579 A1 | 5/2014 | Becker |
| 2014/0134580 A1 | 5/2014 | Becker |
| 2014/0220522 A1 | 8/2014 | Peters |
| 2014/0263224 A1 | 9/2014 | Becker |
| 2014/0272835 A1 | 9/2014 | Becker |
| 2014/0272836 A1 | 9/2014 | Becker |
| 2014/0272837 A1 | 9/2014 | Becker |
| 2014/0272838 A1 | 9/2014 | Becker |
| 2014/0312020 A1 | 10/2014 | Daniel |
| 2014/0315167 A1 | 10/2014 | Kreindl et al. |
| 2014/0322684 A1 | 10/2014 | Wallace |
| 2014/0346158 A1 | 11/2014 | Matthews |
| 2015/0056584 A1 | 2/2015 | Boulware et al. |
| 2015/0056585 A1 | 2/2015 | Boulware et al. |
| 2015/0056586 A1 | 2/2015 | Penrod et al. |
| 2015/0154884 A1* | 6/2015 | Salsich .............. G09B 19/24 434/234 |
| 2015/0170539 A1* | 6/2015 | Chica Barrera ......... G09B 9/00 434/234 |
| 2015/0190875 A1* | 7/2015 | Becker .............. B23K 9/10 700/160 |
| 2015/0190876 A1* | 7/2015 | Becker .............. B23K 9/0956 219/124.34 |
| 2015/0190887 A1* | 7/2015 | Becker .............. B23K 37/00 228/103 |
| 2015/0190888 A1* | 7/2015 | Becker .............. B23K 37/006 434/234 |
| 2015/0194072 A1* | 7/2015 | Becker .............. G09B 19/24 434/234 |
| 2015/0194073 A1* | 7/2015 | Becker .............. G09B 19/24 434/234 |
| 2015/0209887 A1* | 7/2015 | DeLisio .............. B23K 9/0953 219/130.01 |
| 2015/0228203 A1 | 8/2015 | Kindig |
| 2015/0248845 A1* | 9/2015 | Postlethwaite ......... G09B 19/24 434/234 |

(56) References Cited

U.S. PATENT DOCUMENTS

| | | | | |
|---|---|---|---|---|
| 2015/0283640 A1* | 10/2015 | Walker | | B23K 9/0956 219/121.54 |
| 2015/0375323 A1* | 12/2015 | Becker | | B23K 9/0953 700/160 |
| 2015/0375324 A1* | 12/2015 | Becker | | B23K 9/0953 700/212 |
| 2015/0375327 A1* | 12/2015 | Becker | | B23K 9/0956 345/440 |
| 2015/0379894 A1* | 12/2015 | Becker | | G09B 9/00 219/124.1 |
| 2016/0039034 A1* | 2/2016 | Becker | | A61F 9/06 219/137 R |
| 2016/0039053 A1* | 2/2016 | Becker | | G09B 19/24 228/102 |
| 2016/0125592 A1* | 5/2016 | Becker | | G06T 7/73 348/90 |
| 2016/0125593 A1* | 5/2016 | Becker | | G06T 7/73 |
| 2016/0125594 A1* | 5/2016 | Becker | | B23K 9/0953 |
| 2016/0125653 A1* | 5/2016 | Denis | | B23K 9/322 348/90 |
| 2016/0125761 A1* | 5/2016 | Becker | | G09B 19/24 434/234 |
| 2016/0125762 A1* | 5/2016 | Becker | | B23K 9/0956 434/234 |
| 2016/0125763 A1* | 5/2016 | Becker | | B23K 9/126 434/234 |
| 2016/0125764 A1* | 5/2016 | Becker | | G09B 19/24 434/234 |
| 2016/0163221 A1* | 6/2016 | Sommers | | A61F 9/06 434/234 |
| 2016/0260261 A1* | 9/2016 | Hsu | | G06T 19/006 |
| 2016/0267806 A1* | 9/2016 | Hsu | | G09B 19/24 |
| 2016/0288236 A1* | 10/2016 | Becker | | B23K 9/0953 |
| 2016/0321954 A1* | 11/2016 | Peters | | G09B 19/24 |
| 2016/0358503 A1* | 12/2016 | Batzler | | B23K 9/32 |
| 2017/0046974 A1 | 2/2017 | Becker | | |
| 2017/0046975 A1* | 2/2017 | Becker | | G09B 19/003 |
| 2017/0046976 A1* | 2/2017 | Becker | | G09B 19/003 |
| 2017/0046977 A1* | 2/2017 | Becker | | B23K 9/0953 |
| 2017/0053557 A1* | 2/2017 | Daniel | | G09B 19/24 |
| 2017/0080509 A1* | 3/2017 | Pfeifer | | B23K 9/095 |
| 2017/0289424 A1* | 10/2017 | Beeson | | H04N 5/2258 |
| 2019/0035306 A1* | 1/2019 | Becker | | G09B 9/00 |
| 2019/0172195 A1* | 6/2019 | Becker | | G06T 7/0004 |

FOREIGN PATENT DOCUMENTS

| | | |
|---|---|---|
| CN | 101209512 A | 7/2008 |
| CN | 101214178 A | 7/2008 |
| CN | 201083660 Y | 7/2008 |
| CN | 101419755 A | 4/2009 |
| CN | 201229711 Y | 4/2009 |
| CN | 101571887 A | 11/2009 |
| CN | 101587659 A | 11/2009 |
| CN | 102014819 A | 4/2011 |
| CN | 102165504 A | 8/2011 |
| CN | 102298858 A | 12/2011 |
| CN | 202684308 U | 1/2013 |
| CN | 103871279 A | 6/2014 |
| CN | 105057869 A | 11/2015 |
| CN | 107316544 A | 11/2017 |
| DE | 2833638 A1 | 2/1980 |
| DE | 3046634 A1 | 7/1982 |
| DE | 3244307 A1 | 5/1984 |
| DE | 3522581 A1 | 1/1987 |
| DE | 4037879 A1 | 6/1991 |
| DE | 19615069 A1 | 10/1997 |
| DE | 19739720 C1 | 10/1998 |
| DE | 19834205 A1 | 2/2000 |
| DE | 20009543 U1 | 8/2001 |
| DE | 102005047204 A1 | 4/2007 |
| DE | 102010038902 A1 | 2/2012 |
| DE | 202012013151 U1 | 2/2015 |
| EP | 0108599 A1 | 5/1984 |
| EP | 0127299 A1 | 12/1984 |
| EP | 0145891 A1 | 6/1985 |
| EP | 0319623 A1 | 6/1989 |
| EP | 0852986 A1 | 7/1998 |
| EP | 1010490 | 6/2000 |
| EP | 1527852 A1 | 5/2005 |
| EP | 1905533 A2 | 4/2008 |
| ES | 2274736 A1 | 5/2007 |
| FR | 1456780 A | 7/1966 |
| FR | 2827066 A1 | 1/2003 |
| FR | 2926660 A1 | 7/2009 |
| GB | 1455972 A | 11/1976 |
| GB | 1511608 A | 5/1978 |
| GB | 2254172 A | 9/1992 |
| GB | 2435838 A | 9/2007 |
| GB | 2454232 A | 5/2009 |
| JP | 478719 S | 10/1972 |
| JP | 5098035 U | 8/1975 |
| JP | 2224877 | 9/1990 |
| JP | 5329645 | 12/1993 |
| JP | 07047471 | 2/1995 |
| JP | 07232270 | 9/1995 |
| JP | 8132274 A | 5/1996 |
| JP | 8150476 | 6/1996 |
| JP | H08505091 A | 6/1996 |
| JP | 11104833 | 4/1999 |
| JP | 2000167666 A | 6/2000 |
| JP | 2001071140 A | 3/2001 |
| JP | 2002278670 A | 9/2002 |
| JP | 2002366021 A | 12/2002 |
| JP | 2003200372 A | 7/2003 |
| JP | 2003271048 A | 9/2003 |
| JP | 2003326362 A | 11/2003 |
| JP | 2006006604 A | 1/2006 |
| JP | 2006281270 A | 10/2006 |
| JP | 2007290025 A | 11/2007 |
| JP | 2009500178 A | 1/2009 |
| JP | 2009160636 A | 7/2009 |
| JP | 2011528283 | 11/2011 |
| JP | 2012024867 A | 2/2012 |
| KR | 10-0876425 | 12/2008 |
| KR | 20090010693 A | 1/2009 |
| KR | 10-2011-0068544 | 6/2011 |
| KR | 20140030644 A | 3/2014 |
| RU | 2008108601 A | 9/2009 |
| SU | 1038963 A1 | 8/1983 |
| SU | 1651309 A1 | 5/1991 |
| WO | WO-9845078 A1 | 10/1998 |
| WO | 2001009867 | 2/2001 |
| WO | WO-0112376 A1 | 2/2001 |
| WO | WO-0143910 A1 | 6/2001 |
| WO | WO-0158400 A1 | 8/2001 |
| WO | WO-2005102230 A1 | 11/2005 |
| WO | WO-2006034571 A1 | 4/2006 |
| WO | WO-2007009131 A1 | 1/2007 |
| WO | WO-2007039278 A1 | 4/2007 |
| WO | WO-2009060231 A1 | 5/2009 |
| WO | WO-2009120921 A1 | 10/2009 |
| WO | 2009/146359 A1 | 12/2009 |
| WO | WO-2009149740 A1 | 12/2009 |
| WO | WO-2010000003 A2 | 1/2010 |
| WO | WO-2010020867 A2 | 2/2010 |
| WO | WO-2010020870 A2 | 2/2010 |
| WO | WO-2010044982 A1 | 4/2010 |
| WO | WO-2010091493 A1 | 8/2010 |
| WO | WO-2011045654 A1 | 4/2011 |
| WO | WO-2011058433 A1 | 5/2011 |
| WO | WO-2011067447 A1 | 6/2011 |
| WO | WO-2011097035 A2 | 8/2011 |
| WO | 2011148258 A2 | 12/2011 |
| WO | WO-2012082105 A1 | 6/2012 |
| WO | WO-2012143327 A1 | 10/2012 |
| WO | WO-2013014202 A1 | 1/2013 |
| WO | WO-2013061518 A1 | 5/2013 |
| WO | WO-2013114189 A1 | 8/2013 |
| WO | WO-2013175079 A1 | 11/2013 |
| WO | WO-2014007830 A1 | 1/2014 |
| WO | WO-2014019045 A1 | 2/2014 |

(56) References Cited

FOREIGN PATENT DOCUMENTS

| WO | WO-2014020386 A1 | 2/2014 |
|----|------------------|--------|
| WO | 2016137578 A1 | 1/2016 |
| WO | 2014140721 | 9/2017 |

OTHER PUBLICATIONS

William Huff, Khoi Nguyen,"Computer Vision Based Registration Techniques for Augmented Reality", Colorado School of Mines, Division of Engineering, Proceedings of Intellectual Robots and Computer Vision XV, pp. 538-548; SPIE vol. 2904, Nov. 18-22, 1996, Boston MA.
European Search Report for European Patent Application 10860823. 3-1702, pp. 1-8, dated Jun. 6, 2017.
Benkai Xie, Qiang Zhou and Liang Yu; A Real Time Welding Training System Base on Virtual Reality; ONEW 360; Wuhan University of Technology; IEEE Virtual Reality Conference; Mar. 23-27, 2015.
Extended European Search Report from Corresponding Application No. EP17001819.6; dated Apr. 11, 2018.
"High Performance Computer Architectures_ A Historical Perspective," downloaded May 5, 2016.
http://homepages.inf.ed.ac.uk/cgi/rni/comparch. pl?Paru/perf.html,Paru/perf-f.html,Paru/menu-76.html.
Abbas, et al., Code Aster (Software) EDR (France) 14 pages, Oct. 2001.
Abbas, et al., Code_Aster; Introduction to Code_Aster; User Manual; Booket U1.0-: Introduction to Code_Aster; Document: U1.02.00; Version 7.4; Jul. 22, 2005.
Abida et al., "Numerical simulation to study the effect of tack welds and root gap on welding deformations and residual stresses of a pipe-flange joint", Faculty of Mechanical Engineering, GIK Institute of Engineering Sciences and Technology, Topi, NWFP, Pakistan. Available online Aug. 25, 2005.
Adams, et al., "Adaptively sampled particle fluids," ACM SIG-GRAPH 2007 papers, Aug. 5-9, 2007, San Diego, California.
Agren, "Sensor Integration for Robotic Arc Welding;" 1995; vol. 5604C of Dissertations Abstracts International p. 1123; Dissertation Abs Online (Dialog® File 35): © 2012 ProQuest Info& Learning: http://dialogweb.com/cgi/dwclient?req=1331233317524; one (1) page; printed Mar. 8, 2012.
Aidun et al., Penetration in Spot GTA Welds during Centrifugation, Journal of Materials Engineering and Performance vol. 7(5) Oct. 1998—597.
Aidun, D., "Influence of Simulated High-g on the Weld Size of Al—Li Alloy" Elevator Science Ltd.; 2001; 4 pages.
Aiteanu et al., "Generation and Rendering of a Virtual Welding Seam in an Augmented Reality Training Environment" Proceedings of the Sixth IASTED International Conference, Aug. 2006, 8 pages.
Aiteanu, "Virtual and Augmented Reality Supervisor for a New Welding Helmet" Dissertation Nov. 15, 2005.
Aiteanu, et al., "A Step Forward in Manual Welding:; Demonstration of Augmented Reality Helmet" Institute of Automation, University of Bremen,; Germany, Proceedings of the Second IEEE and ACM International Symposium on Mixed and; Augmented Reality; 2003; 2 pages.
Aiteanu, et al., "Computer-Aided Manual Welding Using an Augmented; Reality Supervisor" Sheet Metal Welding Conference XII, Livonia, MI, May 9-12, 2006, 14 pages.
American Welding Society Advance Program of Programs and Events. Nov. 11-14, 2007. 31 pages. Chicago, IL.
American Welding Society Detroit Section, "Sheet Metal Welding Conference XII", May 2006, 11 pages.
American Welding Society, "Vision for Welding Industry"; 41 pages, Estimated Jan. 1998.
American Welding Society, ANSI/A WS D 10.11 MID 10. 11 :2007 Guide for Root Pass Welding of Pipe without Backing Edition: 3rd American Welding Society / Oct. 13, 2006/36 pages ISBN: 0871716445.

American Welding Society, http://www.nsrp.org/6-presentations/WDVirtual_Welder. pdf (Virtual Reality Welder Training,; Project No. S1051, Navy ManTech Program, Project Review for Ship Tech 2005); 22 pages.; Biloxi, MS.
American Welding Society, https://app.aws.org/conferences/defense/live index.html (AWS Welding in the Defense; Industry conference schedule, estimated Jan. 2004); 12 pages.
American Welding Society, https://app.aws.org/w/r/www/wj/2005/03/WJ_2005_03.pdf (AWS Welding Journal, Mar. 2005; (see, e.g., p. 54)).; 114 pages.
American Welding Society, https://app.aws.org/wj/2004/04/052/njc (AWS Virtual Reality Program to Train Welders for; Shipbuilding, workshop information, 2004); 7 pages.
American Welding Society, https://app.aws.org/wj/2007 /11/WJ200711. pdf (AWS Welding Journal, Nov. 2007); 240 pages.
American Welding Society, Welding Handbook, Welding Science & Technology, Ninth Ed., Copyright 2001. Appendix A "Terms and Definitions".
Antonelli et al, "A Semi-Automated Welding Station Exploiting Human-Robot Interaction," Advanced Manufacturing Systems and Technology (2011) pp. 249-260.
ARC+—Archived Press Release from WayBack Machine from Jan. 31, 2008—Apr. 22, 2013, Page, https://web.archive.org/web/20121006041803/http://www.123certification.com/en/article_press/index.htm, Jan. 21, 2016, 3 pages.
ARC+ simulator; http://www.123arc.com/en/depliant_ang.pdf; Estimated Jan. 2000.
Kenneth Fast; Virtual Welding—A Low Cost Virtual Reality Welder system training system phase II; NSRP ASE Technology Investment Agreement: Feb. 29. 2012: pp. 1-54.
ArcSentry Weld Quality Monitoring System; Native American Technologies, allegedly 2002, 5; pages.
ARS Electronica Linz Gmbh, Fronius, 2 pages, May 18, 1997.
ARVIKA Forum Vorstellung Projekt PAARi. BMW Group Virtual Reality Center. 4 pages.; Nuernberg. 2003.
asciencetutor.com, A division of Advanced Science and Automation Corp., VWL (Virtual Welding Lab), 2 pages, 2007.
ASME Definitions, Consumables, Welding Positions, dated Mar. 19, 2001. See http://www.gowelding.com/wp/asme4.htm.
Balijepalli, et al. "Haptic Interfaces for Virtual Environment and Teleoperator Systems," Haptics 2003, Department of Mechanical & Aerospace Engineering, State University of New York at Buffalo, NY.
Bargteil, et al., "A semi-lagrangian contouring method for fluid simulation," ACM Transactions on Graphics, 25(1), 2006.
Bargteil, et al., "A texture synthesis method for liquid animations," In Proceedings of the ACM SIGGRAPH/Eurographics Symposium on Computer Animation, Sep. 2006.
Bender Shipbuilding and Repair Co. Virtual Welding—A Low Cost Virtual Reality Welding; Training System. Proposal submitted pursuant to MSRP Advanced Shipbuilding Enterprise; Research Announcement, Jan. 23, 2008. 28 pages, See also, http://www.nsrp.org/6-; Presentations/WD/020409 Virtual Weldinq Wilbur.pdf.
Borzecki, et al., Specialist Committee V.3 Fabrication Technology Committee Mandate, Aug. 20-25, 2006, 49 pages, vol. 2, 16th International Ship and Offshore Structures Congress, Southampton, UK.
Catalina, et al., "Interaction of Porosity with a Planar Solid/Liquid Interface" ("Catalina"), Metallurgical and Materials Transactions, vol. 35A, May 2004, pp. 1525-1538.
ChemWeb.com—Journal of Materials Engineering (printedSep. 26, 2012) (01928041).
Chen, et al., "Self-Learning Fuzzy Neural Networks and Computer Vision for Control of Pulsed GTAW," dated May 1997.
Chentanez, et al., "Liquid simulation on lattice-based tetrahedral meshes." In ACM SIGGRAPH/Eurographics Symposium on Computer Animation 2007, pp. 219-228, Aug. 2007.
Chentanez, et al., "Simultaneous coupling of fluids and deformable bodies," In ACM SIGGRAPH/Eurographics Symposium on Computer Animation, pp. 83-89, Aug. 2006.
Choquet, C., "ARC+: Today's Virtual Reality Solution for Welders" Internet Page, Jan. 1, 2008; 6 pages.

(56) References Cited

OTHER PUBLICATIONS

Choquet, C., "ARC+®: Today's Virtual Reality Solution for Welders", Published in Proceedings of the IIW Internatioal Conference; Jul. 10-11, 2008; 19 pages.
Clausen, et al., "Simulating liquids and solid-liquid interactions with lagrangian meshes," ACM Transactions on Graphics, 32(2):17:1-15, Apr. 2013. Presented at SIGGRAPH 2013.
Cooperative Research Program, Virtual Reality Welder Training, Summary Report SR 0512, 4 pages, Jul. 2005.
CS WAVE, The Virtual Welding Trainer, 6 pages, 2 estimated Jan. 2007.
CS Wave—Manual, "Virtual Welding Workbench User Manual 3.0" estimated Jan. 2007.
CUDA Programming Guide Version 1.1, Nov. 29, 2007.
Da Dalto, et al. "CS WAVE, A Virtual learning tool for welding motion", 10 pages, Mar. 14, 2008.
Da Dalto, et al. "CS Wave: Learning welding motion in a virtual environment" Published in Proceedings of the IIW International Conference, Jul. 10-11, 2008.
Desroches, X.; Code-Aster, Note of use for aciculations of welding; Instruction manual U2.03 booklet: Thermomechanical; Document: U2.03.05; Oct. 1, 2003.
D'Huart, et al., "Virtual Environment for Training" 6th International Conference, ITS 20002, Jun. 2002; 6 pages.
Dotson, "Augmented Reality Welding Helmet Prototypes How Awesome the Technology Can Get," Sep. 26, 2012, Retrieved from the Internet: URL:http://siliconangle.com/blog/2012/09/26/augmented-reality-welding-helmet-prototypes-how-awesome-the-technology-can-get/,retrieved on Sep. 26, 2014, 1 page.
Echtler et al, "17 The Intelligent Welding Gun: Augmented Reality for Experimental Vehicle Construction," Virtual and Augmented Reality Applications in Manufacturing (2003) pp. 1-27.
Edison Welding Institute, E-Weld Predictor, 3 pages, 2008.
Eduwelding+, Training Activities with arc+ simulator; Weld Into The Future, Online Welding Simulator—A virtual training environment; 123arc.com; 6 pages, May 2008.
Eduwelding+, Weld Into the Future; Online Welding Seminar—A virtual training environment; 123arc.com; 4 pages, 2005.
Energetics, Inc. "Welding Technology Roadmap", Sep. 2000, 38 pages.
Fast, K. et al., "Virtual Training for Welding", Mixed and Augmented Reality, 2004, ISMAR 2004, Third IEEE and CM International Symposium on Arlington, VA, Nov. 2-5, 2004.
Feldman, et al., "Animating Suspended Particle Explosions". In Proceedings of ACM SIGGRAPH 2003, pp. 708-715, Aug. 2003.
Feldman, et al., "Fluids in deforming meshes" In ACM SIGGRAPH/Eurographics Symposium on Computer Animation 2005, Jul. 2005.
Fite-Georgel, "Is there a Reality in Industrial Augmented Reality?" 10th IEEE International Symposium on Mixed and Augmented Reality (ISMAR). 10 pages, allegedly 2011.
Foster, et al., "Realistic animation of liquids," Graphical Models and Image Processing, v.58 n.5, p. 471-483, Sep. 1996.
Foster, et al., "Practical animation of liquids," Proceedings of the 28th annual conference on Computer graphics and interactive techniques, p. 23-30, Aug. 2001.
Garcia-Allende, et al., "Defect Detection in Arc-Welding Processes by Means of the Line-to-Continuum Method and Feature Selection" www.mdpi.com/journal/sensors; Sensors 2009, 9, 7753-7770; DOI; 10.3390/s91007753.
Goktekin, et al., "A Method for Animating Viscoelastic Fluids". ACM Transactions on Graphics (Proc. of ACM SIGGRAPH 2004), 23(3):463-468, 2004.
Graham, "Texture Mapping" Carnegie Mellon University Class 15-462 Computer graphics, Lecture 10 dated Feb. 13, 2003; 53 pages.

Grahn, A., "Interactive Simulation of Contrast Fluid using Smoothed Particle Hydrodynamics," Jan. 1, 2008, Master's Thesis in Computing Science, Umeå University, Department of Computing Science, Umeå, Sweden.
Guu et al., "Technique for Simultaneous Real-Time Measurements of Weld Pool Surface Geometry and Arc Force," Dec. 1992.
Heston, Virtually Welding—raining in a virtual environment gives welding students a leg up, retrieved on Apr. 12, 2010 from: http://www.thefabricator.com/article/arcwelding/virtually-welding.
Hillers, et al., "Augmented Reality—Helmet for the Manual; Welding Process" Institute of Automation, University of Bremen, Germany; 21 pages, 2004.
Hillers, et al., "Direct welding arc observation without harsh flicker," 8 pages, allegedly Fabtech International and AWS welding show, 2007.
Hillers, et al., "Real time Arc-Welding Video Observation System." 62nd International Conference of IIW, Jul. 12-17, 2009, 5 pages Singapore 2009.
Hillers, et al., "TEREBES:; Welding Helmet with AR Capabilities", Institute of Automatic University Bremen; Institute of; Industrial Engineering and Ergonomics, 10 pages, allegedly 2004.
Hillis, et al., "Data Parallel Algorithms", Communications of the ACM, Dec. 1986, vol. 29, No. 12, p. 1170.
Hirche, et al. "Hardware Accelerated Per-Pixel Displacement Mapping" University of Tubingen, Germany, Alexander Ehlert, Stefan Guthe, WStIGRfS & Michael Doggett, ATI Research; 8 pages.
Holmberg et al, "Efficient modeling and rendering of turbulent water over natural terrain," In Proceedings of the 2nd international conference on Computer graphics and interactive techniques in Australasia and South East Asia (GRAPHITE '04) 2004.
Sun Yaoming; Application of Micro Computer in Robotic Technologies; Science and Technology Literature Press; Catalogue of New Books of Science and Technology; Sep. 1987, pp. 360-363.
Hu et al. "Heat and mass transfer in gas metal arc welding. Part 1: the arc" found in ScienceDirect, International Journal of Heat and Mass transfer 50 (2007) 833-846 Available on Line on Oct. 24, 2006 http://web.mst.edu/~tsai/publications/Hu-IJHMT-2007-1-60.pdf.
Impact Welding: examples from current and archived website, trade shows, etc. See, e.g.,; http://www.impactweldinq.com. 53 pages; estimated Jan. 2000.
Irving, et al., "Efficient simulation of large bodies of water by coupling two and three dimensional techniques," ACM SIGGRAPH 2006 Papers, Jul. 30-Aug. 3, 2006, Boston, Massachusetts.
Jeffus, "Welding Principles and Applications" Sixth Edition, 2008, 10 pages.
Jonsson et al. "Simulation of Tack Welding Procedures in Butt Joint Welding of Plates" Research Supplement, Oct. 1985.
Juan Vicenete Rosell Gonzales, "RV-Sold: simulator virtual para la formacion de soldadores"; Deformacion Metalica, Es. vol. 34, No. 301 Jan. 1, 2008.
Kass, et al., "Rapid, Stable Fluid Dynamics for Computer Graphics," Proceedings of SIGGRAH '90, in Computer Graphics, vol. 24, No. 4, pp. 49-57, 1990.
Klingner, et al., "Fluid animation with dynamic meshes," In Proceedings of ACM SIGGRAPH 2006, pp. 820-825, Aug. 2006.
Kobayashi, et al., "Simulator of Manual Metal Arc Welding with Haptic Display" ("Kobayashi 2001"), Proc. of the 11th International Conf. on Artificial Reality and Telexistence (ICAT), Dec. 5-7, 2001, pp. 175-178, Tokyo, Japan.
Kobayashi, et al., "Skill Training System of Manual Arc Welding by Means of Face-Shield-Like HMD and Virtual Electrode" ("Kobayashi 2003"), Entertainment Computing, vol. 112 of the International Federation for Information Processing (IFIP), Springer Science + Business Media, New York, copyright 2003, pp. 389-396.
Lincoln Global, Inc., "VRTEX 360: Virtual Reality Arc Welding Trainer" Brochure (2015) 4 pages.
Lindholm, et al., "NVIDIA Testla: A Unifired Graphics and Computing Architecture", IEEE Computer Society, 2008.
Mahrle, A., et al.; "The influence of fluid flow phenomena on the laser beam welding process" International Journal of Heat and Fluid Flow 23 (2002, No. 3, pp. 288-297; Institute of Fluid Dynamics and Thermodynamics, Otto-von-Guericke University Magdeburg, P.O. Box 4120, D-39016 Magdeburg, Germany.

(56) References Cited

OTHER PUBLICATIONS

Mann, et al., "Realtime HDR (High Dynamic Range) Video for Eyetap Wearable Computers, FPGA-Based Seeing Aids, and Glasseyes (EYETAPS)," 2012 25th IEEE Canadian Conference on Electrical and Computer Engineering (CCECE),pp. 1-6, Apr. 29, 2012, 6 pages.

Mantinband, et al., "Autosteroscopic, field-sequential display with full freedom of movement or Let the display were the shutterglasses," 3ality (Israel) Ltd., 2002.

Mavrikios D et al, A prototype virtual reality-based demonstrator for immersive and interactive simulation of welding processes, International Journal of Computer Integrated manufacturing, Taylor and Francis, Basingstoke, GB, vol. 19, No. 3, Apr. 1, 2006, pp. 294-300.

Miller Electric Mfg. Co, "LiveArc: Welding Performance Management System" Owner's Manual, (Jul. 2014) 64 pages.

Miller Electric Mfg. Co., "LiveArc Welding Performance Management System" Brochure, (Dec. 2014) 4 pages.

Miller Electric Mfg. Co.; MIG Welding System features weld monitoring software; NewsRoom 2010 (Dialog® File 992); © 2011 Dialog. 2010; http://www.dialogweb.com/cgi/dwclient?reg=1331233430487; three (3) pages; printed Mar. 8, 2012.

Moore, "No exponential is forever: but 'Forever' can be delayed!," IEEE International Solid-State Circuits Conference, 2003.

Müller, et al., "Particle-based fluid simulation for interactive applications," Proceedings of the 2003 ACM SIGGRAPH/Eurographics symposium on Computer animation, Jul. 26-27, 2003, San Diego, California.

Müller, et al., "Point Based Animation of Elastic, Plastic and Melting Objects," Eurographics/ACM SIGGRAPH Symposium on Computer Animation (2004).

N. A. Tech., P/NA.3 Process Modeling and Optimization, 11 pages, Jun. 4, 2008.

Nasios, "Improving Chemical Plant Safety Training Using Virtual Reality," Thesis submitted to the University of Nottingham for the Degree of Doctor of Philosophy, Dec. 2001.

Nealen, A., "Point-Based Animation of Elastic, Plastic, and Melting Objects," CG topics, Feb. 2005.

Nordruch, et al., "Visual Online Monitoring of PGMAW Without a Lighting Unit", Jan. 2005.

NSRP ASE, Low-Cost Virtual Realtiy Welder Training System, 1 page, 2008.

O'Brien et al.,"Dynamic Simulation of Splashing Fluids". In Proceedings of Computer Animation 95, pp. 198-205, Apr. 1995.

O'Brien, "Google's Project Glass gets some more details", Jun. 27, 2012 (Jun. 27, 2012), Retrieved from the Internet: http://www.engadget.com/2012/06/27/googles-project-glass-gets-some-more-details/, retrieved on Sep. 26, 2014, 1 page.

P/NA.3 Process Modelling and Optimization; Native American Technologies, allegedly 2002,; 5 pages.

Penrod, "New Welder Training Tools." EWI PowerPoint presentation; 16 pages allegedly 2008.

Phar, "GPU Gems 2 Programming Techniques for High-Performance Graphics and General-Purpose Computation," 2005, 12 pages.

Porter, et al. Virtual Reality Welder Trainer, Session 5: Joining Technologies for Naval Applications: earliest date Jul. 14, 2006 (http://weayback.archive.org) Edision Welding Institute; J. Allan Cote, General Dynamics Electric Boat; Timothy D. Gifford, VRSim, and Wim Lam, FCS Controls.

Porter, et al., Virtual Reality Training, Paper No. 2005-P19, 14 pages, 2005.

Porter, et al., Virtual Reality Training, vol. 22, No. 3, Aug. 2006; 13 pages.

Porter, et al., Virtual Reality Welder Training, dated Jul. 14, 2006.

Praxair Technology Inc., "The RealWeld Trainer System: Real Weld Training Under Real Conditions" Brochure (Est. Jan. 2013) 2 pages.

Premoze, et al., "Particle-based simulation of fluids," Comput. Graph. Forum 22, 3, 401-410, 2003.

Rasmussen, et al., "Directable photorealistic liquids," Proceedings of the 2004 ACM SIGGRAPH/Eurographics symposium on Computer animation, Aug. 27-29, 2004, Grenoble, France.

Ratnam, et al., "Automatic classification of weld defects using simulated data and an MLP neutral network." Insight vol. 49, No. 3; Mar. 2007.

Reeves, "Particles Systems—A Technique for Modeling a Class of Fuzzy Objects", Computer Graphics 17:3 pp. 359-376, 1983.

Renwick, et al., "Experimental Investigation of GTA Weld Pool Oscillations" Welding Research—Supplement to the Welding Journal, Feb. 1983, 7 pages.

Rodjito, "Position tracking and motion prediction using Fuzzy Logic," 2006, Colby College.

Russel, et al., "Artificial Intelligence: A Modern Approach", Prentice-Hall (Copywrite 1995).

Sandor, et al., "Lessons Learned in Designing Ubiquitous Augmented; Reality User Interfaces." 21 pages, allegedly from Emerging Technologies of Augmented; Reality: Interfaces Eds. Haller, M.; Billinghurst, M.; Thomas, B. Idea Group Inc. 2006.

Sandor, et al., "PAARTI: Development of an Intelligent Welding Gun for; BMW." PIA2003, 7 pages, Tokyo. 2003.

Sandter, et al. Fronius—virtual welding, FH Joanne UM, Gesellschaft mbH, University of; Annlied Sciences 2 pages, May 12, 2008.

Schoder, "Design and Implementation of a Video Sensor for Closed Loop Control of Back Bead Weld Puddle Width," Massachusetts Institute of Technology, Dept. of Mechanical Engineering, May 27, 1983.

Screen Shot of CS Wave Control Centre V3.0.0 https://web.archive.org/web/20081128081915/http://wave.c-s.fr/images/english/snap_evolution4.jpg; Estimated Jan. 2007.

Screen Shot of CS Wave Control Centre V3.0.0 https://web.archive.org/web/20081128081817/http://wave.c-s.fr/images/english/snap_evolution6.jpg, estimated Jan. 2007.

Screen Shot of CS Wave Exercise 135.FWPG Root Pass Level 1 https://web.archive.org/web/20081128081858/http:/wave.c-s.fr/images/english/snap_evolution2.jpg, estimated Jan. 2007.

SimWelder, retrieved on Apr. 12, 2010 from: http://www.simwelder.com.

SIMFOR / CESOL, "RV-SOLD" Welding Simulator, Technical and Functional Features, 20 pages, estimated Jan. 2010.

Slater, et al., "Mechanisms and Mechanical Devices Sourcebook," McGraw Hill; 2nd Addition, 1996.

Stam, J., "Stable fluids," Proceedings of the 26th annual conference on Computer graphics and interactive techniques, p. 121-128, Jul. 1999.

SWANTEC corporate web page downloaded Apr. 19, 2016. http://www.swantec.com/technology/numerical-simulation/.

Tamasi, T., "The Evolution of Computer Graphics," NVIDIA, 2008.

Teeravarunyou, et al, "Computer Based Welding Training System," International Journal of Industrial Engineering (2009) 16(2): 116-125.

Terebes: examples from http://www.terebes.uni-bremen.de.; 6 pages.

The Fabricator, Virtual Welding, 4 pages, Mar. 2008.

The Lincoln Electric Company, "VRTEX Virtual Reality Arc Welding Trainer," http://www.lincolnelectric.com/en-us/equipment/training-equipment/Pages/vrtex.aspx as accessed on Jul. 10, 2015, 3 pages.

The Lincoln Electric Company, Production Monitoring 2 brochure, 4 pages, May 2009.

The Lincoln Electric Company; CheckPoint Production Monitoring borchure; four (4) pages; http://www.lincolnelectric.com/assets/en_US/products/literature/s232.pdf; Publication S2.32; Issue Date Feb. 2012.

Thurey, et al., "Real-time Breaking Waves for Shallow Water Simulations," In Proceedings of the 15th Pacific Conference on Computer Graphics and Applications (PG '07) 2007.

Tonnesen, D., "Modeling Liquids and Solids using Thermal Particles," Proceedings of Graphics Interface'91, pp. 255-262, Calgary, Alberta, 1991.

Tschirner, et al., "Virtual and Augmented Reality for Quality Improvement of Manual Welds" National Institute of Standards and Technology, Jan. 2002, Publication 973, 24 pages.

(56) References Cited

OTHER PUBLICATIONS

Tschirner, et al, "A Concept for the Application of Augmented Reality in Manual Gas Metal Arc Welding." Proceedings of the International Symposium on Mixed and Augmented Reality; 2 pages; 2002.
Vesterlund, M., "Simulation and Rendering of a Viscous Fluid using Smoothed Particle Hydrodynamics," Dec. 3, 2004, Master's Thesis in Computing Science, Umeå University, Department of Computing Science, Umeå, Sweden.
Viega, et al. "Simulation of a Work Cell in the IGRIP Program" dated 2006; 50 pages.
Virtual Welding: A Low Cost Virtual Reality Welder Training System, NSRP RA 07-01—BRP Oral Review Meeting in Charleston, SC at ATI, Mar. 2008.
ViziTech USA, "Changing the Way America Learns," http://vizitechusa.com/ accessed on Mar. 27, 2014; 2 pages.
VRSim Inc. "About Us—History" www.vrsim.net/history, 2016, 1 page.
VRSim Powering Virtual Reality, www.lincolnelectric.com/en-us/equipmenl/lraining-equipmenl/Pages/powered-by-; 'rsim.aspx, 2016, 1 page.
Wade, "Human uses of ultrasound: ancient and modern", Ultrasonics vol. 38, dated 2000.
Wahi, et al., "Finite-Difference Simulation of a Multi-Pass Pipe Weld" ("Wahi"), vol. L, paper 3/1, International Conference on Structural Mechanics in Reactor Technology, San Francisco, CA, Aug. 15-19, 1977.
Wang, et al. "Numerical Analysis of Metal Tranfser in Gas Metal Arc Welding, " Departements of Mechanical and Electrical Engineering. University of Kentucky, Dec. 10, 2001.
Wang, et al., "Impingement of Filler Droplets and Weld Pool During Gas Metal Arc Welding Process" International Journal of Heat and Mass Transfer, Sep. 1999, 14 pages.
Wang, et al., "Study on welder training by means of haptic guidance and virtual reality for arc welding," 2006 IEEE International Conference on Robotics and Biomimetics, ROBIO 2006 ISBN—10: 1424405718, p. 954-958.
Webster's II new college dictionary, 3rd ed., Houghton Mifflin Co., copyright 2005, Boston, MA, p. 1271, definition of "wake.".
White, et al., Virtual welder training, 2009 IEEE Virtual Reality Conference, p. 303, 2009.
Wu, "Microcomputer-based welder training simulator", Computers in Industry, vol. 20, No. 3, Oct. 1992, pp. 321-325, XP000205597, Elsevier Science Publishers, Amsterdam, NL.
Wuhan Onew Technology Co Ltd, "ONEW-360 Welding Training Simulator" http://en.onewtech.com/_d276479751.htm as accessed on Jul. 10, 2015, 12 pages.
Yao, et al., "Development of a Robot System for Pipe Welding" 2010 International Conference on Measuring Technology and Mechatronics Automation. Retrieved from the Internet: http://ieeexplore.ieee.org/stamp/stamp.jsp?tp=&arnumber=5460347&tag=1; pp. 1109-1112.
Yoder, Fletcher, Opinion U.S. Pat. No. Re. 45,398 and U.S. Appl. No. 14/589,317, including Appendices ; filed Sep. 9, 2015; 1700 pages.
United States Provisional Patent Application for "System for Characterizing Manual Welding Operations on Pipe and Other Curved Structures," U.S. Appl. No. 62/055,724, filed Sep. 26, 2014, 35 pages.
Office Action from U.S. Appl. No. 14/526,914 dated Feb. 3, 2017.
Arc Simulation & Certification, Weld Into the Future, 4 pages, 2005, Jan. 2008.
International Search Report and Written Opinion from PCT/IB10/02913 dated Apr. 19, 2011.
International Search Report for PCT/IB2014/001796, dated Mar. 24, 3016; 8 pages.
International Search Report for PCT/IB2015/000161, dated Aug. 25, 2016; 9 pages.

International Search Report for PCT/IB2015/000777, dated Dec. 15, 2016; 11 pages.
International Search Report for PCT/IB2015/000814 dated Dec. 15, 2016; 9 pages.
International Preliminary Report from PCT/IB2015/001084 dated Jan. 26, 2017.
Petition for Inter Partes Review of U.S. Pat. No. 8,747,116; IPR 2016-00749; Apr. 7, 2016; 70 pages.
Declaration of Edward Bohnart, Apr. 27, 2016, exhibit to IPR 2016-00749.
Declaration of Dr. Michael Zyda, May 3, 2016, exhibit to IPR 2016-00749.
Trial Denied IPR Proceeding of U.S. Pat. No. 8,747,116; IPR 2016-00749; Sep. 21, 2016; 21 pages.
Petition for Inter Partes Review of U.S. Pat. No. Re. 45,398; IPR 2016-00840; Apr. 18, 2016; 71 pages.
Declaration of AxelGraeser, Apr. 17, 2016, exhibit to IPR 2016-00840; 88 pages.
Decision Denying Request for Rehearing of U.S. Pat. No. Re. 45,398; IPR 2016-00840; Nov. 17, 2016; 10 pages.
Petition for Inter Partes Review of U.S. Pat. No. 8,747,116; IPR 2016-01568; Aug. 9, 2016; 75 pages.
Decision Termination Proceeding of U.S. Pat. No. 8,747,116; IPR 2016-01568; Nov. 15, 2016; 4 pages.
Petition for Inter Partes Review of U.S. Pat. No. 9,293,056; IPR 2016-00904; May 9, 2016; 91 pages.
Declaration of Edward Bohnart, Apr. 27, 2016, exhibit to IPR 2016-00904; 22 pages.
Declaration of Dr. Michael Zyda, May 3, 2016, exhibit to IPR 2016-00904; 76 pages.
Decision Trial Denied IPR Proceeding of U.S. Pat. No. 9,293,056; IPR 2016-00904; Nov. 3, 2016; 15 pages.
Petition for Inter Partes Review of U.S. Pat. No. 9,293,057; IPR 2016-00905; May 9, 2016; 87 pages.
Declaration of Edward Bohnart, Apr. 27, 2016, exhibit to IPR 2016-00905; 23 pages.
Declaration of Dr. Michael Zyda, May 3, 2016, exhibit to IPR 2016-00905; 72 pages.
Decision Trial Denied IPR Proceeding of U.S. Pat. No. 9,293,057; IPR 2016-00905; Nov. 3, 2016; 21 pages.
*Lincoln Electric Company et al v. Seabery Soluciones SL et al*—1:15-cv-01575-DCN—Complaint filed Aug. 15, 2015 (Dkt 01).
*Lincoln Electric Company et al v. Seabery Soluciones SL et al*—1:15-cv-01575-DCN—Amended Answer filed Mar. 1, 2016 by Seabery North America (docket 44).
*Lincoln Electric Company et al v. Seabery Soluciones SL et al*—1:15-cv-01575-DCN—Amended Answer filed Mar. 1, 2016 by Seabery Soluciones SL (docket 45).
*Lincoln Electric Company et al v. Seabery Soluciones SL et al*—1:15-cv-01575-DCN—Amended Answer filed Mar. 22, 2016 by Lincoln Electri c Company (docket 46).
*Lincoln Electric Company et al v. Seabery Soluciones SL et al*—1:15-cv-01575-DCN—Answer filed Mar. 22, 2016 by Lincoln Global Inc. (docket 47).
Exhibit B from Declaration of Morgan Lincoln in *Lincoln Electric Co. et al. v. Seabery Soluciones, S.L. et al.*, Case No. 1:15-cv-01575-DCN, dated Dec. 20, 2016, 5 pages.
International Serach Report and Written Opinion for International Application No. PCT/IB2009/006605.
European Examination Report for application No. 17001820.4,4 pages, dated May 16, 2019.
U.S. Appl. No. 15/784,979, filed Oct. 16, 2017, System and Method for Calibrating a Welding Trainer.
U.S. Appl. No. 15/785,019, filed Oct. 16, 2017, Welding Trainer Utilizing a Head Up Display to Display Simulated and Real-World Objects.
U.S. Appl. No. 15/785,513, filed Oct. 17, 2017, Communication Between a Welding Machine and a Live Welding Training Device.

* cited by examiner

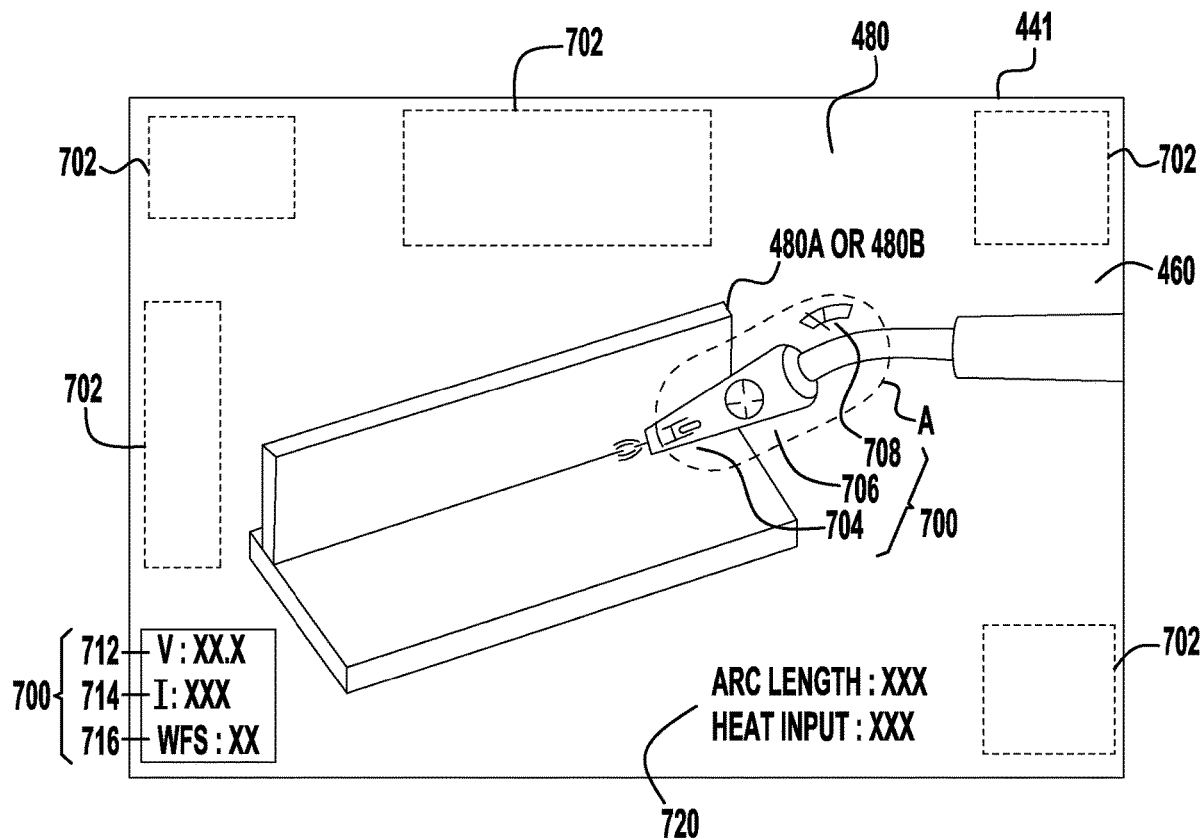
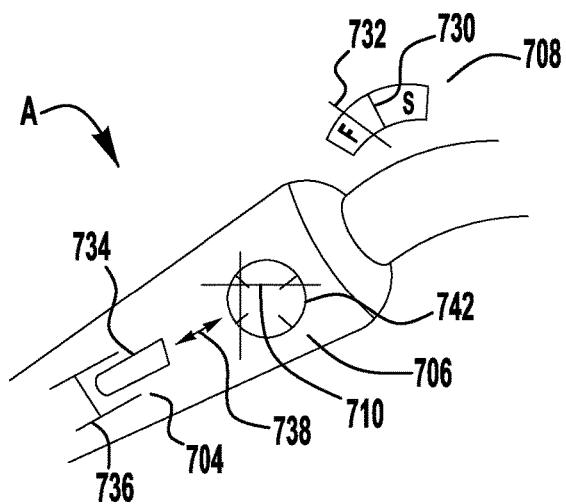
FIG. 18

WELDING SYSTEM PROVIDING VISUAL AND AUDIO CUES TO A WELDING HELMET WITH A DISPLAY

PRIORITY AND INCORPORATION BY REFERENCE

This U.S. Non-Provisional Patent Application claims priority to U.S. Provisional Application Ser. No. 62/418,737, filed Nov. 7, 2016, which is incorporated herein by reference in its entirety. The specifications of U.S. application Ser. No. 14/682,340, filed Apr. 9, 2015; U.S. application Ser. No. 14/037,699, filed Sep. 26, 2013; U.S. application Ser. No. 12/577,824, filed on Oct. 13, 2009, which issued as U.S. Pat. No. 8,569,655; and U.S. Provisional Patent Application No. 61/977,275, filed Apr. 9, 2014, are incorporated herein by reference in their entirety.

BRIEF SUMMARY OF THE INVENTION

Field of the Invention

This invention relates in general to equipment used in welding. Devices, systems, and methods consistent with the invention relate to the monitoring of welding parameters and specifically to a welding system that provides visual and audio cues to a display located in the welder's helmet.

Description of the Related Art

Welding is an important process in the manufacture and construction of various products and structures. Applications for welding are widespread and used throughout the world, for example, the construction and repair of ships, buildings, bridges, vehicles, and pipe lines, to name a few. Welding may performed in a variety of locations, such as in a factory with a fixed welding operation or on site with a portable welder.

In manual or semi-automated welding a user/operator (i.e. welder) directs welding equipment to make a weld. For example, in arc welding the welder may manually position a welding rod or welding wire and produce a heat generating arc at a weld location. In this type of welding the spacing of the electrode from the weld location is related to the arc produced and to the achievement of optimum melting/fusing of the base and welding rod or wire metals. The quality of such a weld is often directly dependent upon the skill of the welder.

Welders generally rely upon a variety of information when welding. This information includes, for example, current and voltage. Traditionally, welders would need to look at gauges on the control panel of the welding equipment to gain this information. This would require the welder to direct their field of vision away from the welding work area and as such was undesirable. In addition, in many cases, the welding machine may not be located close to the work space. In such cases, the welding machine is operated by a cable-connected remote control that can be used to change parameters such as, e.g., welding power, polarity, arc characteristics, etc. However, before the process can be set up, the welder may need to see the display readouts that are physically located on the machine. The setting-up process may require many trips before the set-up is completed.

In the past, efforts have been made to provide welders with information during welding, such as in the method disclosed in U.S. Pat. No. 4,677,277, where current and voltage are monitored to produce an audio indication to the operator as to the condition of the arc in arc welding. However, monitors consisting only of audio arc parameter indicators are hard to hear and interpolate and are not capable of achieving the desired closeness of control and quality of weld often required.

More recently, as disclosed in U.S. Pat. No. 6,242,711, an apparatus for monitoring arc welding has been developed that provides a welder with real-time voltage and current conditions of the welding arc where information in the form of lights, illuminated bar graphs, light projections, illuminated see-through displays, or the like are placed within the visual range of the helmet wearing operator and located in proximity to the helmet viewing window in the helmet. However, in this apparatus a welder must still move their visual focus away from the welding work area in order to focus on the information located proximate to the welding window or the welder must accept the information peripherally while continuing to focus on the welding work area. In addition, related art welding devices have limited guidance with respect to aiding the welder, whether a beginner or exercised, as the weld is being performed.

BRIEF SUMMARY OF THE INVENTION

This invention relates to a welding helmet that is capable of providing an image representative of information from an associated welding operation where the image appears on a display in the welding helmet. The display can be face-mounted display such as an LCD display or a head up display (HUD).

Various aspects will become apparent to those skilled in the art from the following detailed description and the accompanying drawings.

BRIEF DESCRIPTION OF THE DRAWINGS

The above and/or other aspects of the invention will be more apparent by describing in detail exemplary embodiments of the invention with reference to the accompanying drawings, in which:

FIG. 18 illustrates a perspective view of the welding environment as viewed on or through the display of a welding helmet.

DETAILED DESCRIPTION OF EXEMPLARY EMBODIMENTS

Figure 1:
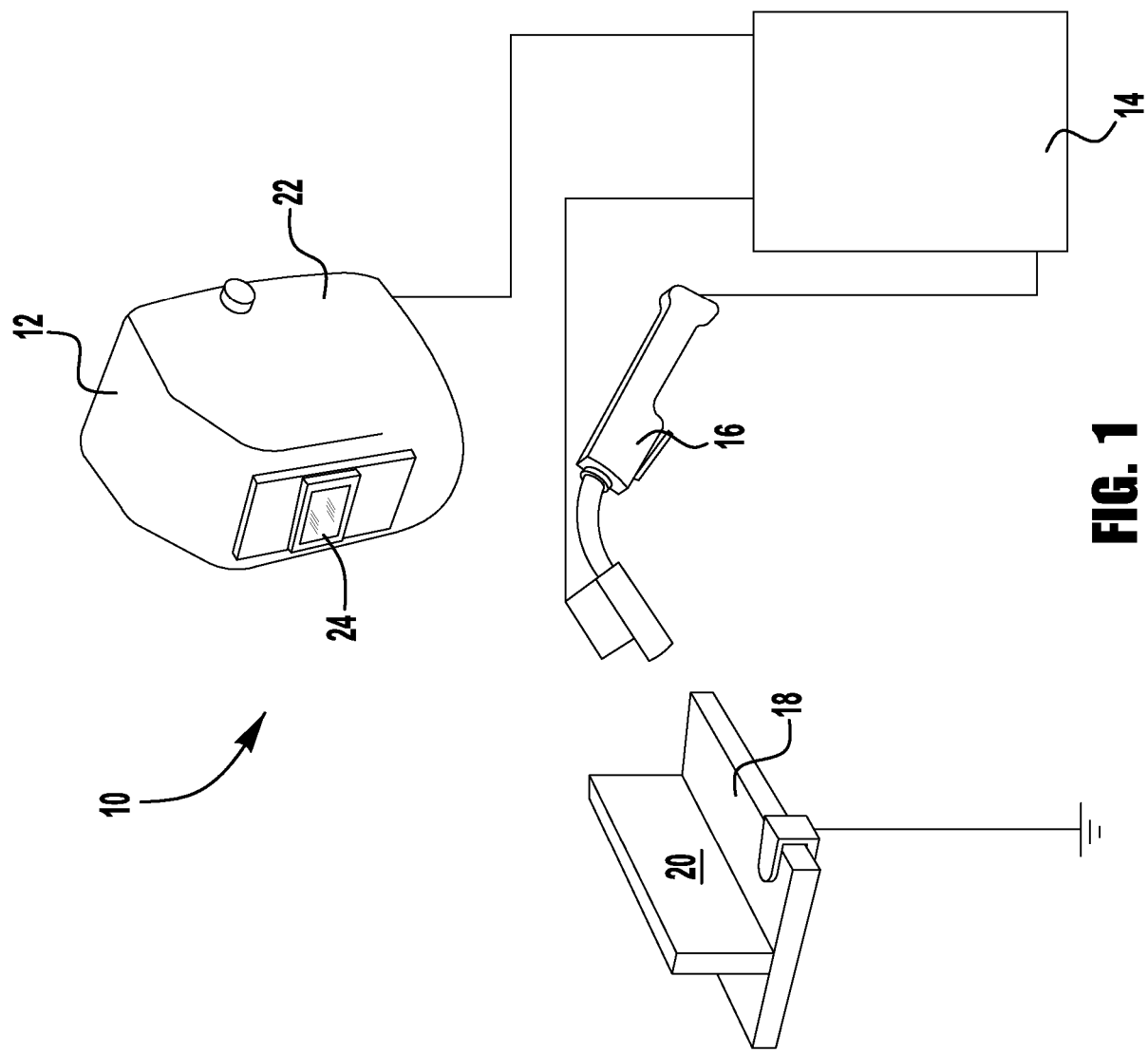
FIG. 1 is a schematic view of a welding system according to the present invention.

Exemplary embodiments of the invention will now be described below by reference to the attached Figures. The described exemplary embodiments are intended to assist the understanding of the invention, and are not intended to limit the scope of the invention in any way. Like reference numerals refer to like elements throughout.

Referring now to the drawings, there is illustrated in FIG. 1 a welding system 10. The welding system 10 includes a welding helmet 12, a welding system 14, a welding gun 16 and a work piece 18. The work piece 18 generally defines a welding work area 20 where the welding gun 16 may be used to form a weld.

The welding system 14 includes welding equipment for generating a welding current and voltage, a welding control system for controlling the welding current and voltage, and a monitoring system for monitoring the welding current and voltage. That is, the welding system, can be on known or used welding power supply having a known construction and operation. The monitoring system may also monitor a variety of other operating parameters, such as but not limited to, wire feed speed, amount of wire used/amount of wire remaining, any type of welding feedback desired by the operator and any other desired operating parameter.

The welding helmet 12 includes a main body 22 with a visual display 24 connected to the main body 22. The display 24 may be a window including a welding lens, a video monitor, such as an LCD display or LED array, or any other device suitable to allow a welder to see the welding work area 20. It must be understood that in such an example where the display 24 is a video monitor video processing may be utilized to enhance the pictures of the welding operation. Further, recording devices may optionally be included in the display, for example, to record and later playback welding operations for analysis and/or evaluation.

Figure 2:
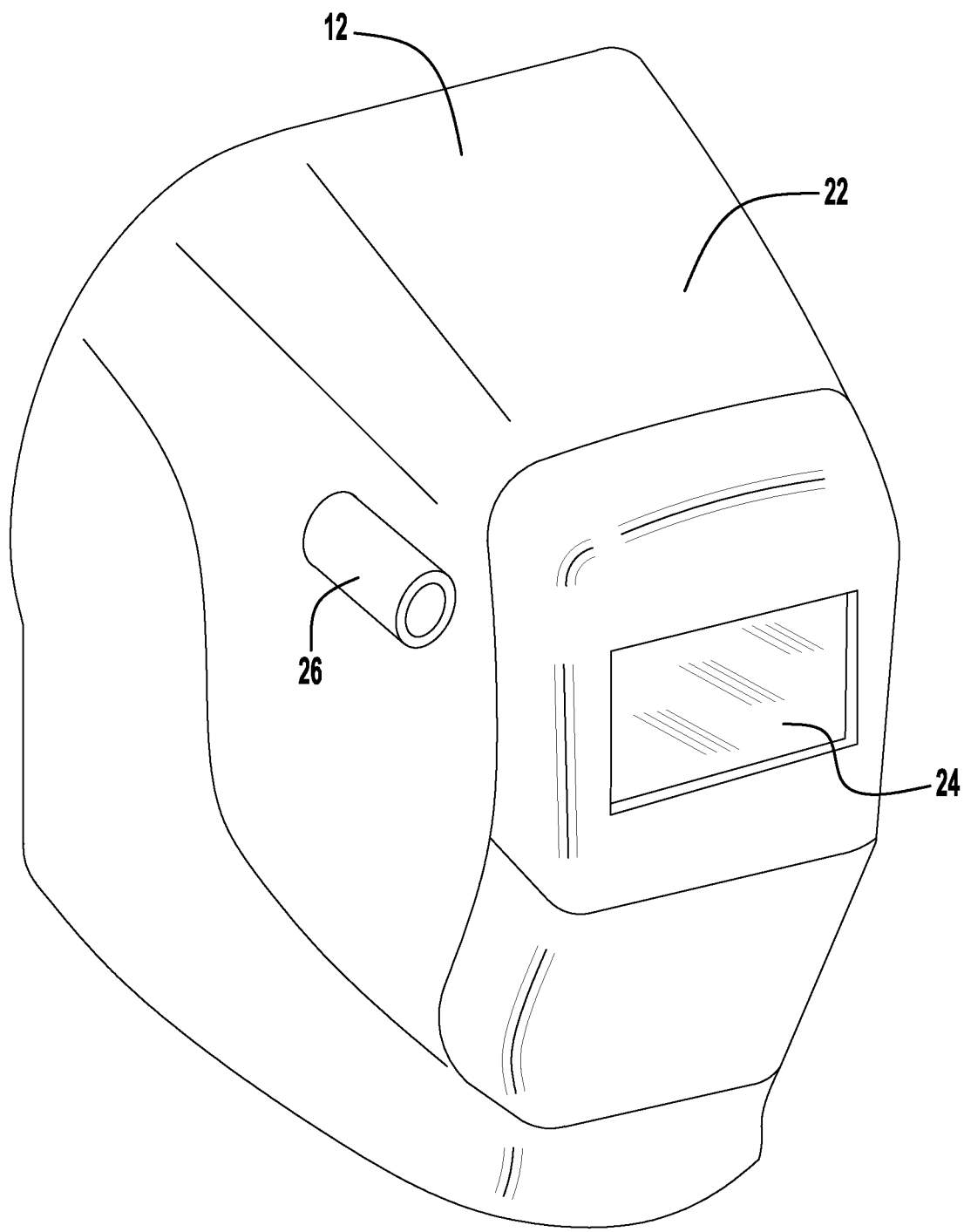
FIG. 2 is an enlarged view of a welding helmet similar to the helmet of FIG. 1 including a camera.

As shown in FIG. 2, a welding helmet 12 may include a camera 26 mounted at or proximate to the point of view of the welder. In the example where the visual display 24 is a video monitor, the camera 26 may provide video pictures of the welding work area 20 to the display 24. Further, the camera 26 can be used to record the welding operation as it is ongoing, so that the welding operation can be viewed at a later time.

Figure 3:
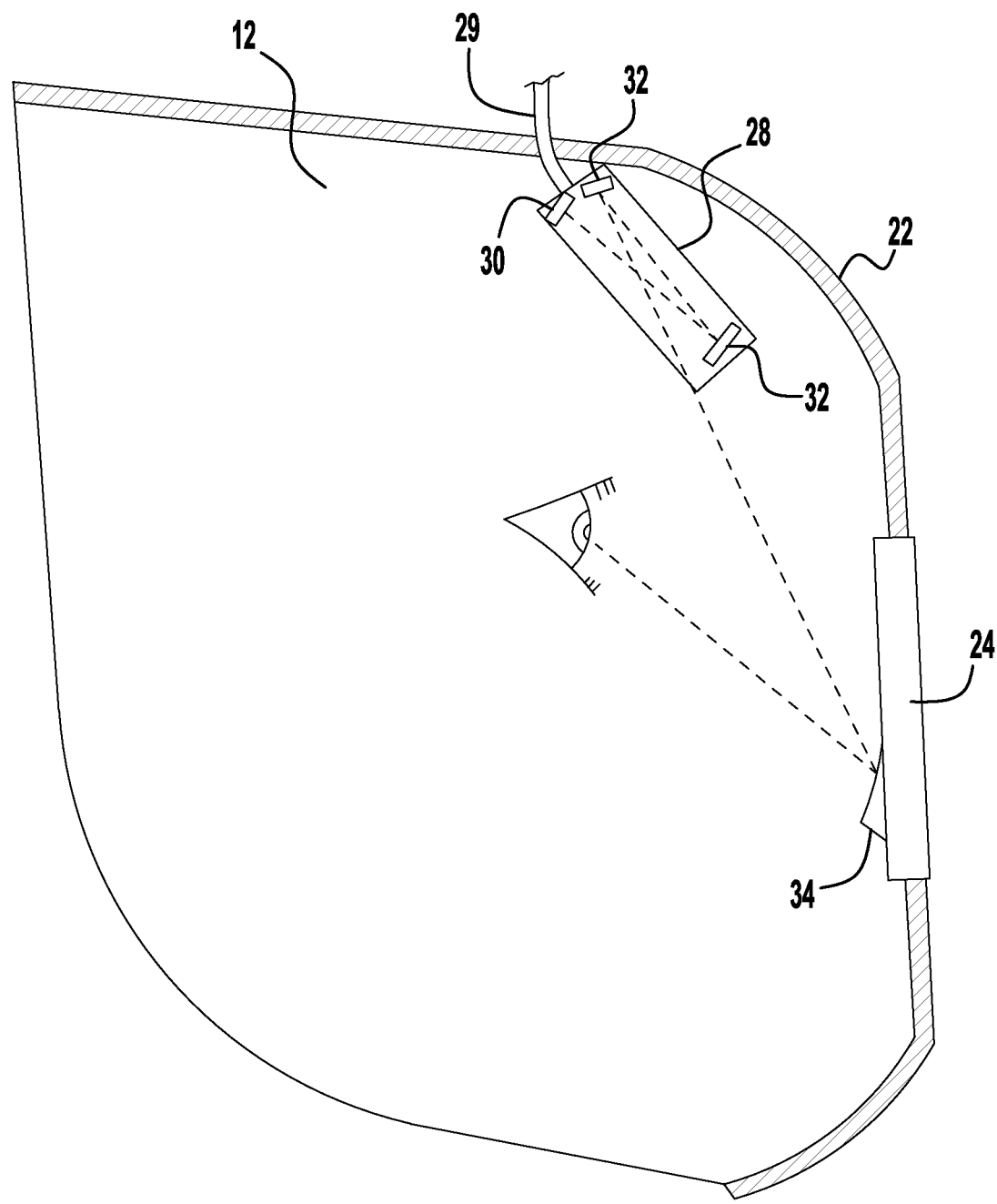
FIG. 3 is a cross-sectional diagram of a welding helmet similar to the helmet of FIG. 2 including a projector.
Figure 4:
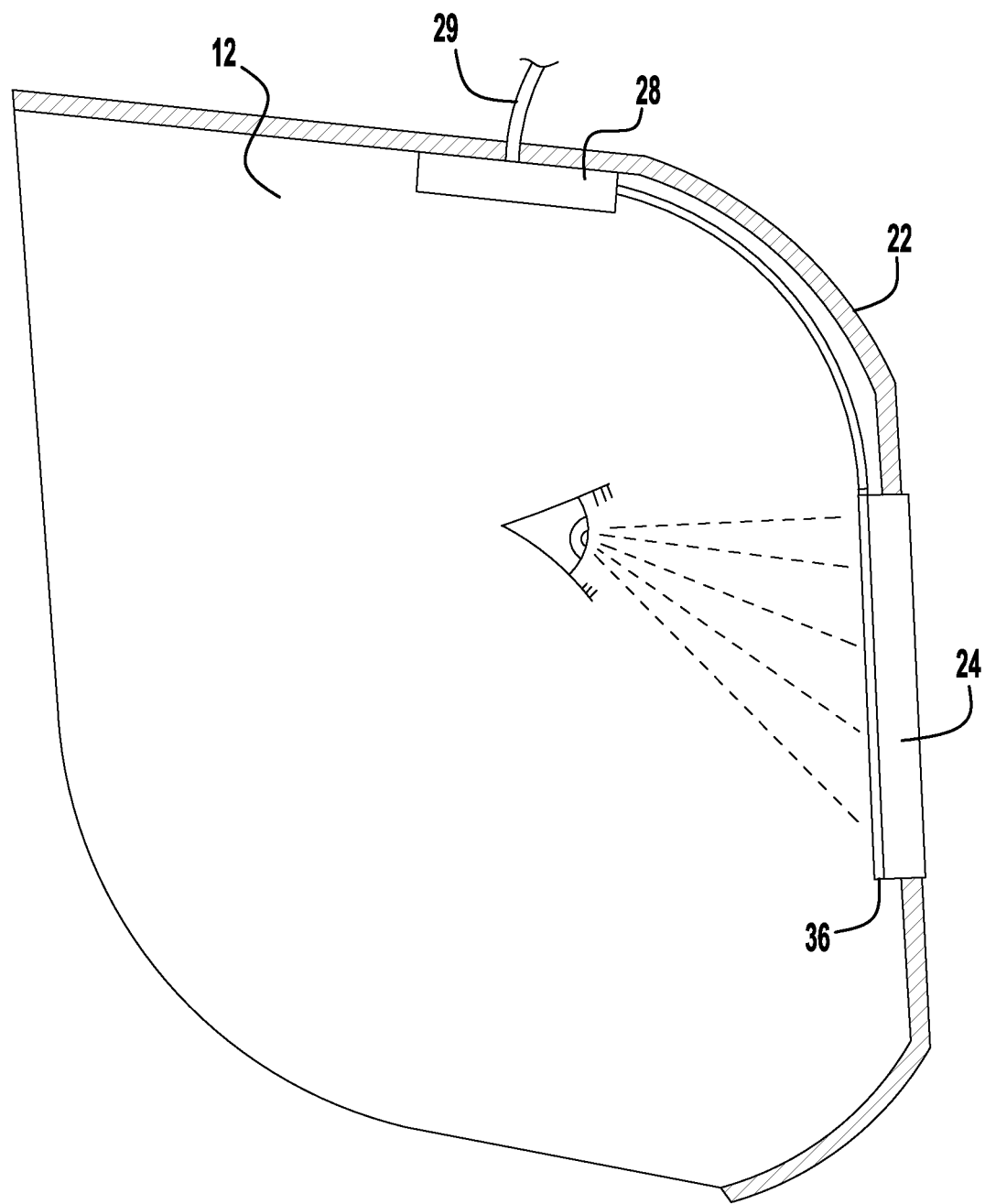
FIG. 4 is a cross-sectional diagram of a welding helmet similar to the helmet of FIG. 3 including an integrated video display.

As shown in FIGS. 3 and 4 an information generating mechanism 28 is in communication with the monitoring system of the welding system 14 and capable of generating an image representative of information from the monitoring system based upon the monitored welding parameter, such as current and voltage upon the visual display 24 where the focus of the image is at a focus range (i.e., having a focal point) with an associated welding work area, e.g. outside of the main body 22 of the welding helmet 12. That is, the focal range of the image displayed in/on the display 24 is set to be at a range associated with the location of the welding work area 20. For example, the image may be symbolic, alphanumeric, or any other device suitable to indicate the information. Thus, a welder may view an image representative of information about a welding operation without removing focus from the work area. Thus, in at least one embodiment the welder may focus on the work area and the image of information at the same time.

It must be understood that among other types of information, along with a variety of other parameter, the information based upon welding current and voltage includes, but is not limited to, welding current feedback, welding voltage feedback, control settings of the welding equipment, statistical information of the welding process, benchmarks or limits including capacity representations, alerts including material shortage or low flow, a representation of an intended or desired weld, etc.

Further, in one embodiment, the camera 26 is used to calibrate the depth of the image relative to the welding work area 20. This calibrated depth can be used to determine the focus of the information displayed on the display 24. For example, if the camera 26 determines that the distance from the helmet to the work area is 2 feet, the images and/or information shown on the display 24 is displayed such that the image has a focal point which would be at 2 feet beyond the helmet. As explained above, this allows the displayed information to be displayed at a same focal length as the weld area 20 so that the welder need not change his/her eye focus during a welding operation. In another embodiment, positions sensors on the welding gun may be used to calibrate the depth of the image. Such sensors can include, but are not limited to, magnetic sensors, optical sensors, acoustics sensors, and the like, which are sensed using an appropriate sensing system to allow for the positioning of the welding gun to be determined. This data can be used to aid in determining the focal range/distance of the work area relative to the helmet. In particular applications it is highly desirable to carefully align the image and the welding work such that the information represented in the image is easy for the welder to access and such that the information in the image is readily accepted by the welder.

In the example where the visual display 24 is a video monitor, information generating mechanism 28 may include an image representative of information from the monitoring system based upon the monitored parameter, such as welding current and voltage, in video pictures of the welding work area 20 shown on the display 24.

As indicated at 29, the information generating mechanism 28 may be in wired or wireless communication with other devices as desired.

In FIG. 3, the information generating mechanism 28 is a projector. The projector may, for example, include an internal LCD display or LED array 30 along with a number of associated mirrors 32 to reflect the image generated to the visual display 24. The reflected image gives the image the appearance of depth relative to the visual display 24 and thus puts the image at a focus range with an associated welding work area and outside of the main body 22 of the welding helmet 12 and optionally at the same focal distance as the associated welding work area 20. Optionally, a reflective surface 34 may be placed upon a portion of the visual display 24 in order to achieve a desired amount of reflection or reflection angle. In one embodiment, teleprompter type technology may be utilized to place the image upon the display 24 or surface 34. Additionally, it must be understood that one embodiment includes the use of an LCD display or other similar display within the helmet to generate the image which is then sent along an optical path, such as by reflection or fiber optics or any other suitable device to place the image display 24 or surface 34.

In FIG. 4, the information generating mechanism 28 includes a screen, film, or sheet 36 integrated into the visual display 24. The sheet 36 may be a semi-transparent LCD film, electro-optic film, or any other suitable medium for the information generating mechanism 28 to produce an image generated in the visual display 24. In one application, the information generating mechanism 28 may project a stereogram on the welding lens such that a welder's eyes will separately view the images to create the perception of depth and thus focus the image at a focus range with the associated welding work area 20 and outside of the main body 22 of the welding helmet 12.

Figure 5:
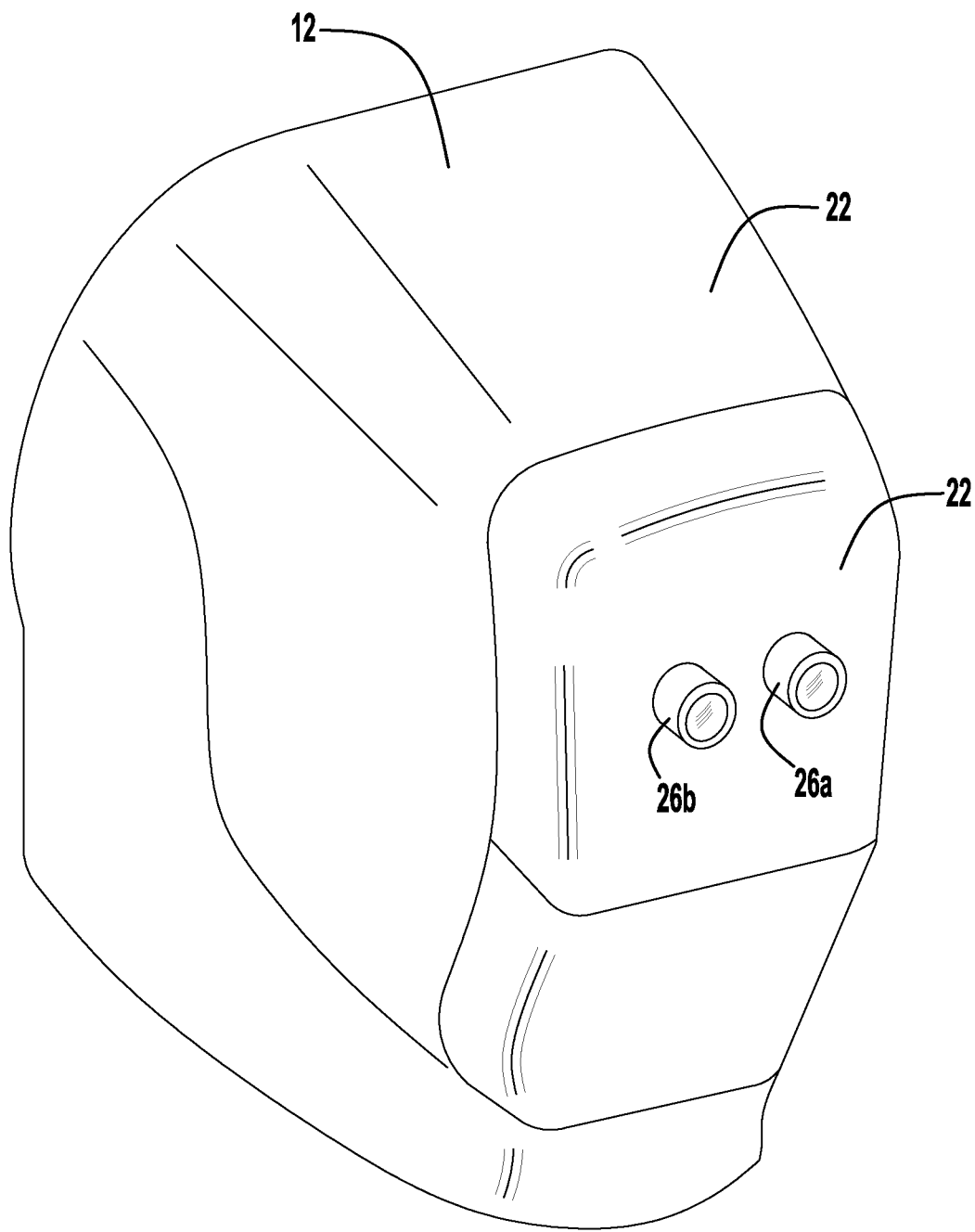
FIG. 5 is a perspective view of a welding helmet similar to the helmet of FIG. 2 including binocular cameras.
Figure 6:
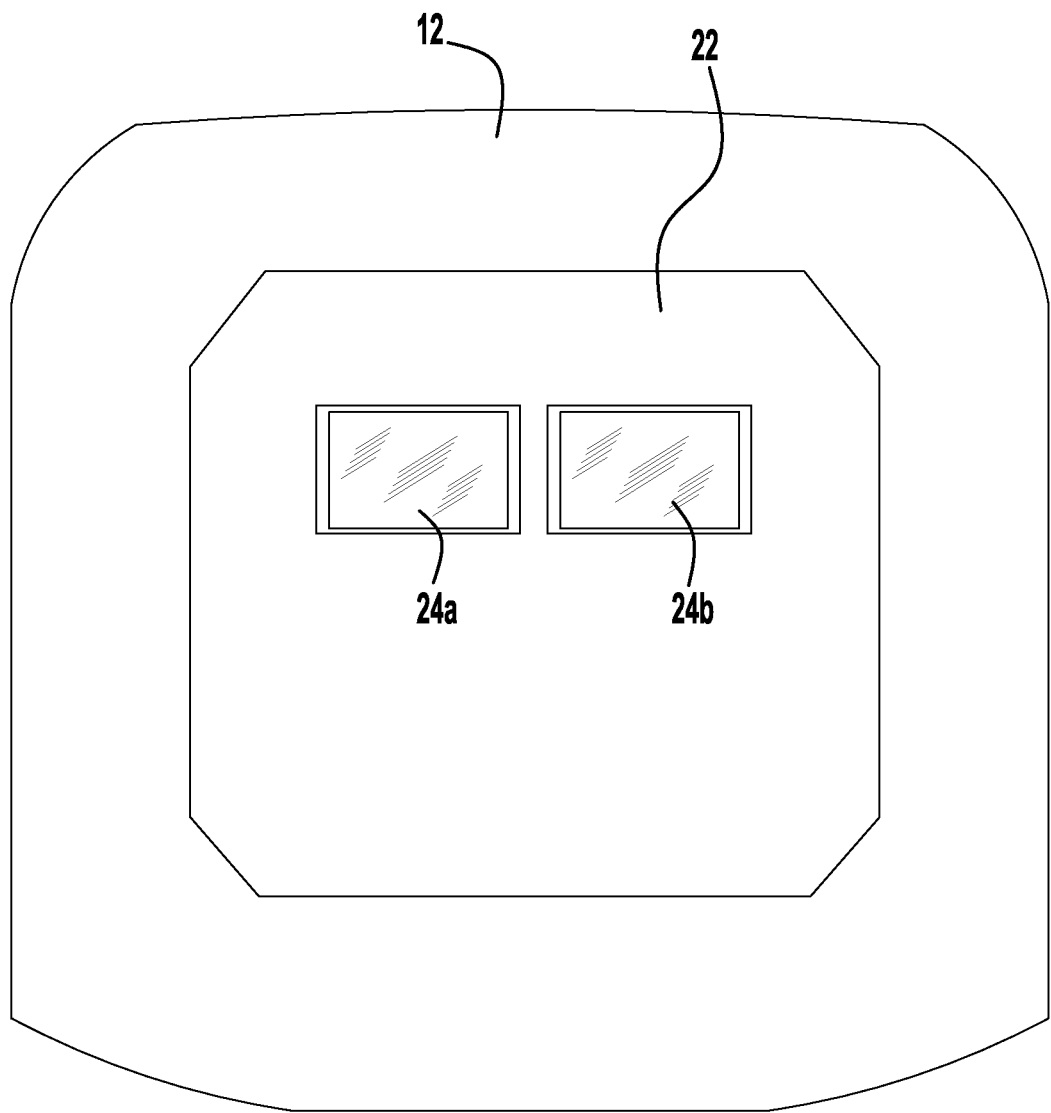
FIG. 6 is an interior view of a welding helmet similar to the helmet of FIG. 5 showing binocular viewing screens.

There is shown in FIG. 5 a welding helmet 12 including binocular cameras 26a and 26b. As shown in FIG. 6, these cameras 26a and 26b correspond to binocular viewing screens 24a and 24b. An information generating mechanism may produce an image to be generated in either of the viewing screens 24a or 24b or both. In one embodiment, the cameras 26a and 26b are placed in alignment with the screens 24a and 24b except on opposite sides of the main body 22, thus giving the welder the view directly in front of them. Additionally, in the embodiment with binocular cameras 26a and 26b and binocular viewing screens 24a and 24b the perception of depth of field is produced.

In any case, the image may be an overlay of text or graphics or video feedback. Additionally, it is contemplated that in at least one embodiment the system described above may be used in a remote welding situation, including but not limited to robotic welding or underwater welding.

While principles and modes of operation have been explained and illustrated with regard to particular embodiments, it must be understood, however, that this may be practiced otherwise than as specifically explained and illustrated without departing from its spirit or scope.

Figure 7:
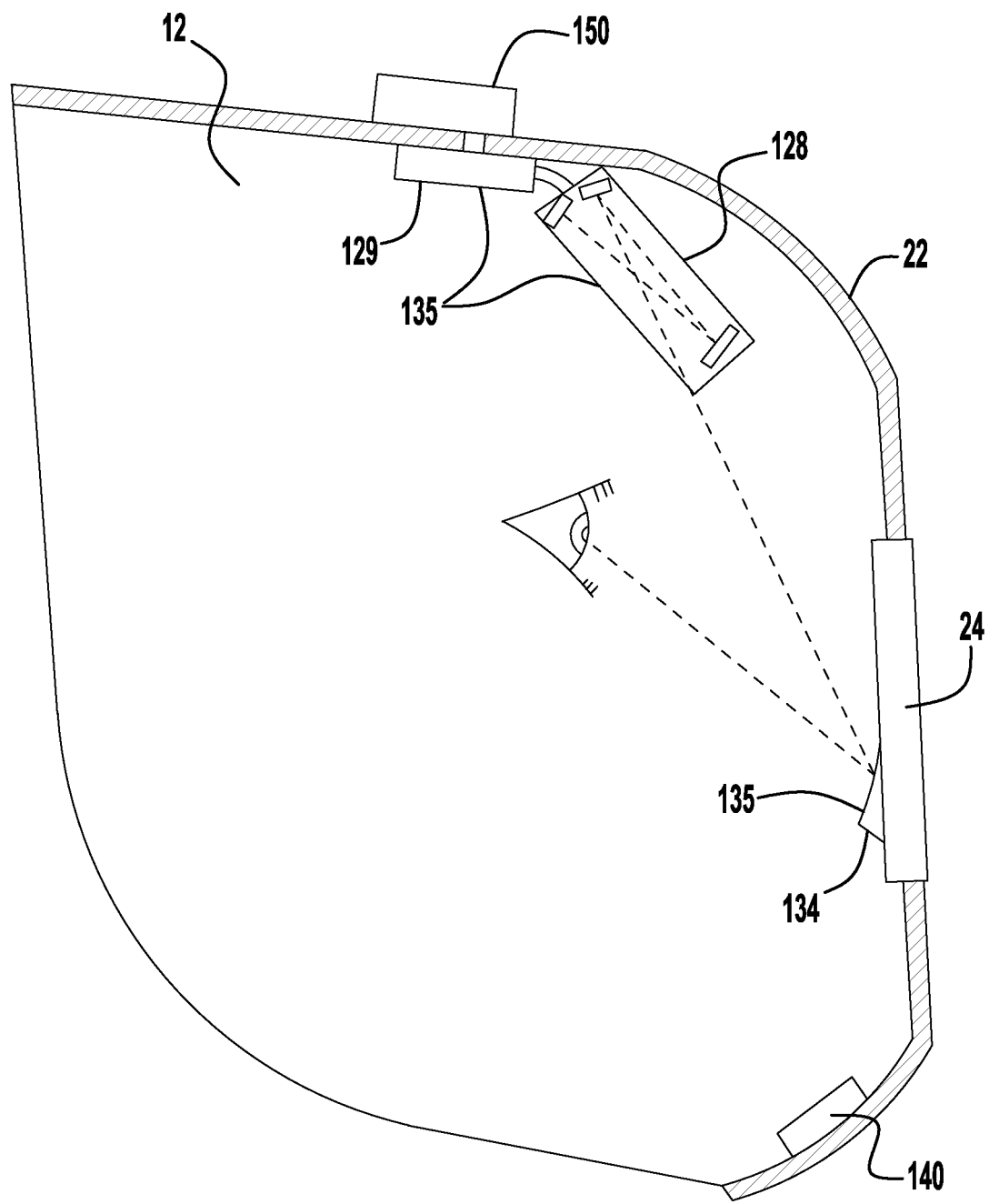
FIG. 7 is a cross-sectional diagram of an exemplary embodiment a welding helmet with a HUD.
Figure 8:
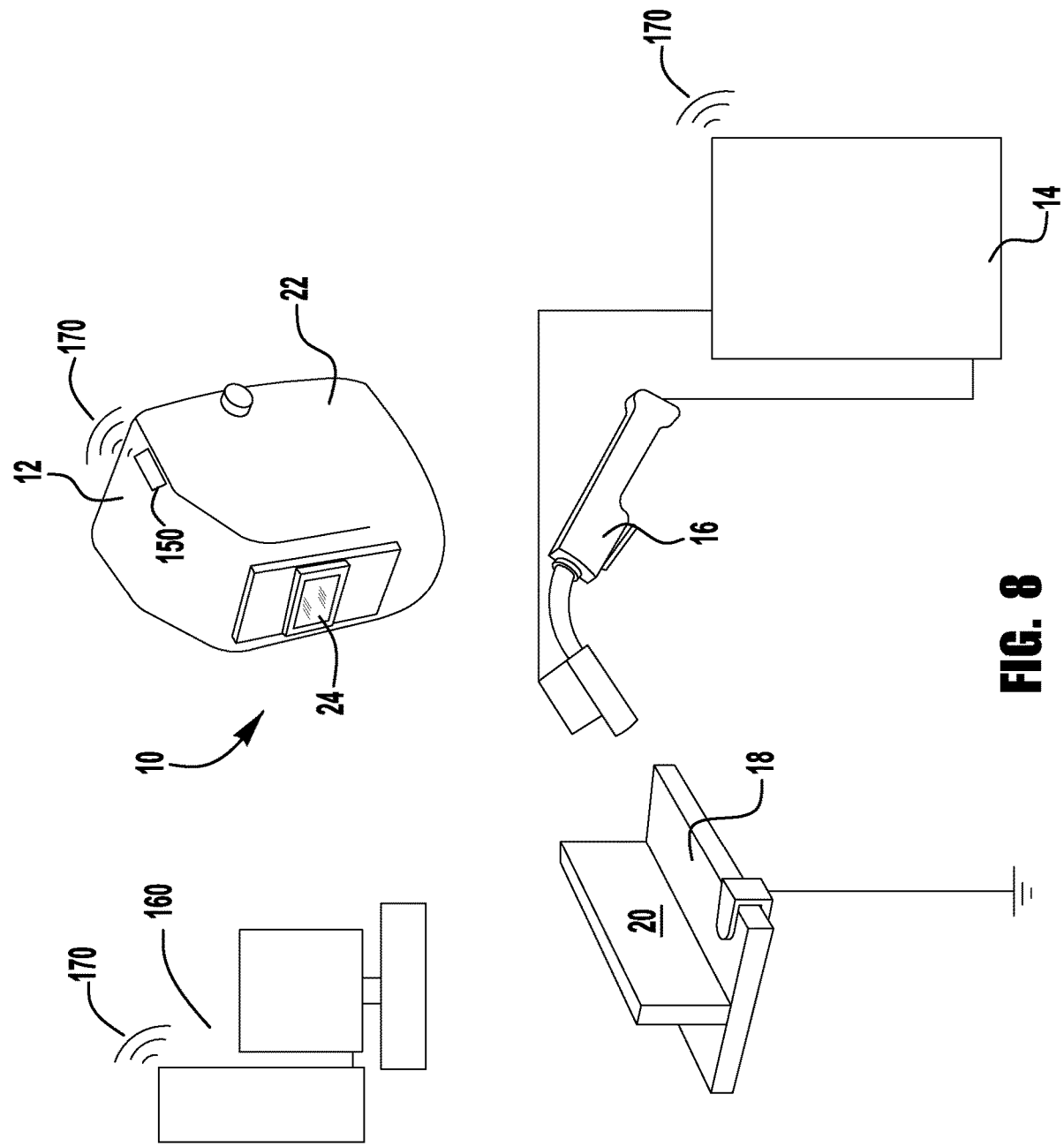
FIG. 8 is a schematic view of a welding system according to an exemplary embodiment of present invention.

Some exemplary embodiments of the present invention, as illustrated in FIG. 7, include a welding helmet 12 with a head-up display (HUD) 135 for the welder. In some embodiments, the HUD 135 includes a projector 128, a combiner 134, and an information generating device 129. The projector 128 can be, e.g., an LED array, an LCD display, a laser, a combination LED/LCD system, or some other suitable projector system. The projector 128 projects an image onto the combiner 134. The image can be in the form of text, graphics, video, etc. The projector 128 receives image information, e.g., in the form of a digital signal, from information generating device 129. The information generating device 129 generates and/or processes the image based on information received from an external source such as, e.g., a welding system 14 or a computer system 160 (see FIG. 8). This information can include, among other types of information, welding parameters such as input power, input current, input voltage, welding voltage, welding current, welding power, tip-to-work distance, arc length, wire feed speed, etc. In some embodiments, the projector 128 and information generating device 129 can be integrated into a single physical unit. In some embodiments, the computer system 160 and/or the welding system 14 generates and/or processes the image and transmits the image information directly to projector 128, which can include and/or is connected to a wireless communication device.

The combiner 134 reflects the image projected from projector 128 to the welder. In some embodiments, light transmitted through lens 24 is also transmitted through combiner 134. Thus, the welder will see both the projected image and the field of view behind the combiner 134 at the same time. The light transmitted through lens 24 can be that from a welding arc transmitted through lens 24. In some embodiments, the lens 24 is of a type that rapidly and automatically changes from transparent to dark when the lens 24 detects that a welding arc has been initiated. The auto-darkening feature protects the welder's eyes from damage that could occur if the eye is exposed to the welding arc. The auto-darkening lens is transparent when no arc is detected and thus allows the welder to see the work space even when the welding helmet 12 is flipped down over the welder's face. With an auto-darkening lens, the light transmitted through lens 24 and combiner 134 can be either the light from the welding arc or normal room lighting depending on whether a welding operation is taking place.

In some embodiments, the combiner 134 collimates the reflected image such that the projected image appears to be at optical infinity. Thus, the welder will not have to re-focus to see both the work space and the projected image—even during the welding process. In some embodiments, the combiner 134 is an appropriate transparent material, e.g., a flat piece of glass, that is angled such that the projected image from the projector 128 is reflected to the welder as illustrated in FIG. 7. In some embodiments, the mounting of the combiner 134 to welding helmet 12 and/or lens 24 is such that the angle of reflection can be adjusted by the welder, as desired.

In some embodiments, the combiner 134 includes a coating that reflects monochromatic light from the projector 128. For example, the coating on the combiner 134 can be such that only, e.g., green light is reflected and all other light is transmitted through. Thus, the HUD 135 will provide the welder a transparent display that allows the welder to see information on the combiner 134 in green while still allowing the welder to view the work space. Of course, other coatings that reflect other colors or even multiple colors can be used on the combiner 134. For example, the combiner 134 can be coated such that it reflects the colors green and red. While in the normal operating range, the information, e.g., welding current, may be displayed in green and when outside the normal operating range, the information, e.g., welding current, can be displayed in red. The information provided to the welder can include welding operating parameters such as, e.g., input current, input voltage, input power, welding current, welding voltage, wire feed speed, contact tip-to-work distance, arc length, mode of operation, etc.

Figure 9:
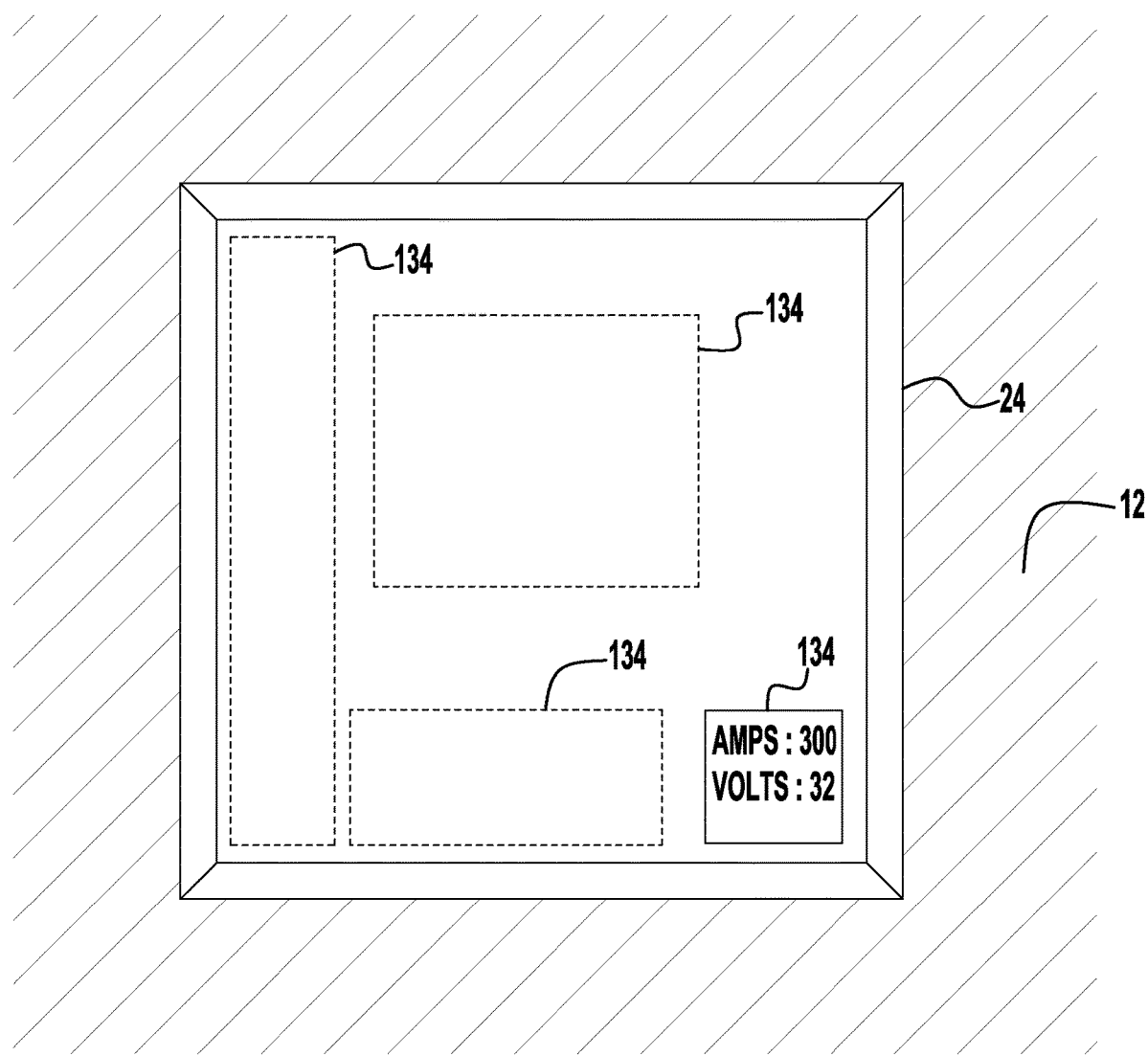
FIG. 9 is an interior view of a welding helmet with a HUD.
Figure 10A:
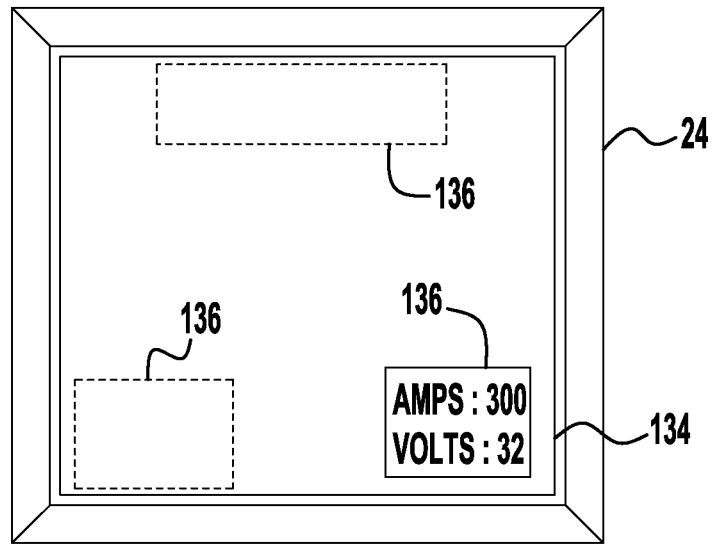
FIGS. 10A and 10B are an interior views of a welding helmet with a HUD.
Figure 10B:
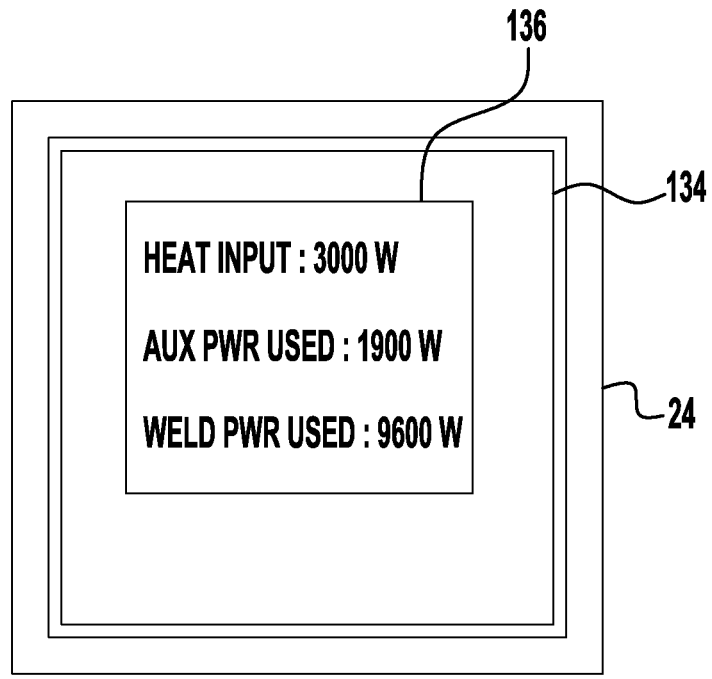

The size, shape, and placement of the combiner 134 relative to the lens 24 can vary, as desired. For example, FIG. 9 illustrates various sizes, shapes, and locations for the combiner 134. The illustrated sizes and locations are exemplary and any appropriate size, shape, and location can be utilized. For example, in some embodiments, the combiner 134 is sized such that it covers the entire opening of lens 24 (see FIGS. 10A and 10B). Similarity, an image window, i.e. the window in which actual information is displayed, on the combiner 134 can be sized and/or located as desired. For example, as seen in FIG. 10 A, during an actual welding process an image window 136 can be displayed in a corner and/or along an edge of the combiner 134 so that the welder is not distracted but still has the information available, if desired. When the welding process is not occurring, the image window 136 can be displayed larger as seen in FIG. 10B. The HUD 135 can be configured such that the image 136 is automatically resized based on whether welding system 14 is performing a welding operation. Alternately, or in addition, the HUD 135 can be configured such that the resizing of image 136 is a manual operation by the welder.

Figure 11:
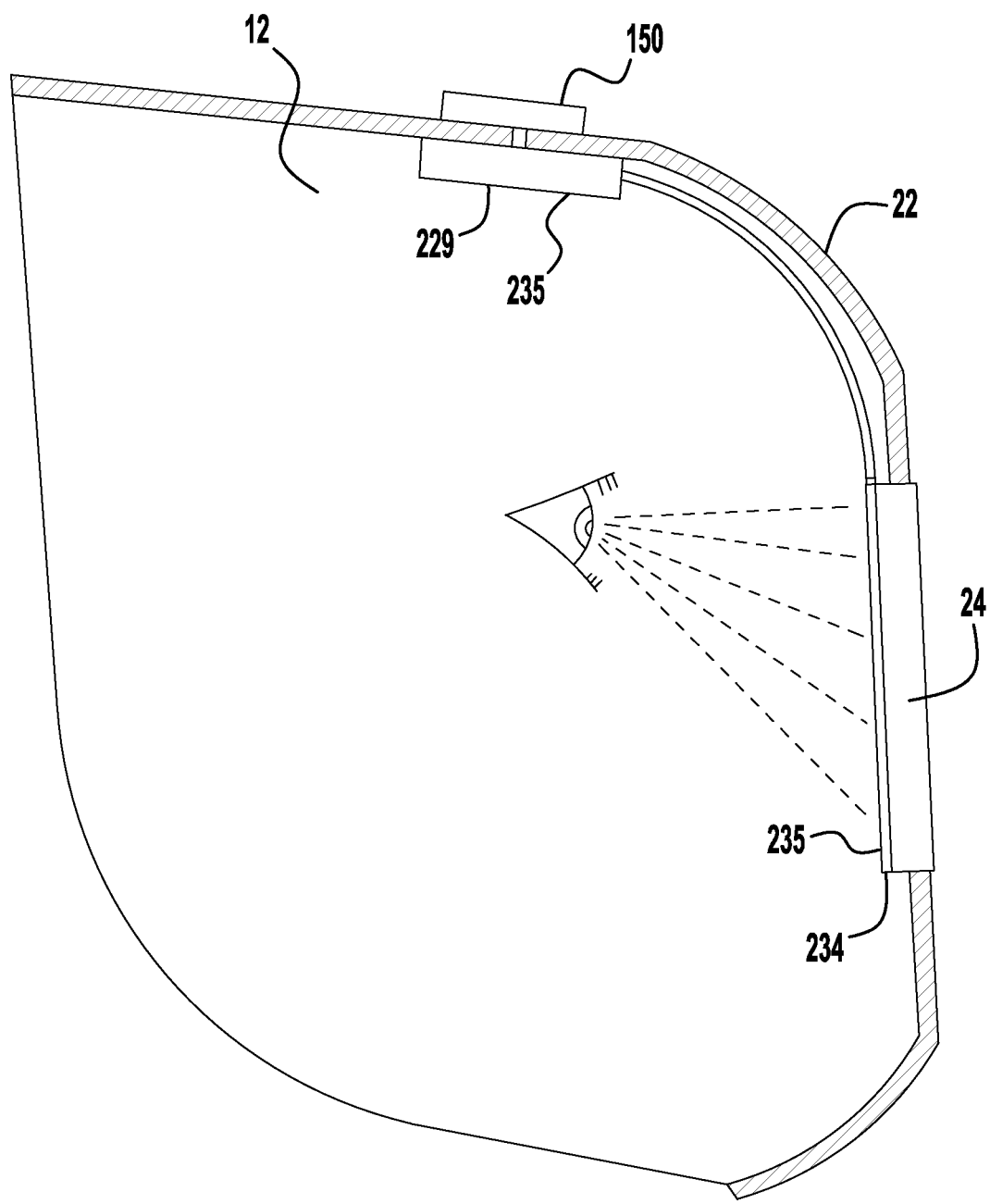
FIG. 11 is a cross-sectional diagram of an exemplary embodiment of a welding helmet with a HUD.

In some embodiments, the projector is not used. As illustrated in FIG. 11, a HUD 235 includes combiner 234 and information generating device 229. In this exemplary embodiment, the image is produced directly in the combiner 234. The combiner 234 can be, e.g., an LCD display, optical waveguide, an electro-optical medium, or some other suitable medium for producing an image. Similar to combiner 134 discussed above, the size, shape, and placement of the combiner 234 relative to the lens 24 can vary, as desired, including having a display size that is equal to the size of the window of lens 24. In addition, similar to image window 136 discussed above, an image window on combiner 234 can be sized and/or located as desired.

The combiner 234 receives image information, e.g., in the form a digital signal, from information generating device 229, which generates and/or processes the image based on information received from welding system 14 and/or computer system 160. In some embodiments, the combiner 234 and information generating device 229 can be integrated into a single physical unit. In some embodiments, the combiner 234 and lens 24 can be integrated into a single physical unit. In some embodiments, the combiner 234, information generating device 229, and lens 24 can be integrated into a single physical unit. In some embodiments, the computer system 160 and/or the welding system 14 generates and/or process the image and transmits the image information directly to combiner 234, which can include or is connected to a wireless communication device.

The information generating devices 129 and 229 can each include a communication device 150 to communicate via, e.g., a wireless network 170 or a wired network with welding system 14 and/or computer system 160. The wireless network 170 can operate using, e.g., Bluetooth, WiFi (IEEE 802.11) or some other wireless protocol. In some embodiments, the welding system 14 can provide information such as e.g., input power, input current, input voltage, welding current, welding voltage, welding power, contact tip-to-work distance, arc length, wire feed speed, etc. in real-time to, e.g., aid the welder while the welding operation is going on. Alternatively, or in addition, the welding system 14 can send welding performance information after the welder has stopped welding. For example, the welding system 14 can transmit information such as, e.g., heat input, duration of welding, etc. after, e.g., the welder system 14 is turned off, indicating that the welder is done welding. Such information might be useful to the welder in order to make corrections before starting the next welding segment.

In some embodiments, the computer system 160 performs all the calculations such as, e.g., heat input, welding duration, etc. The computer system 160 can communicate with the welding system 14 and/or the welding helmet 12 via, e.g., wireless network 170 or a wired network. In some embodiments, the computer system 160 collects, stores, and/or analyzes information received from the welding system 14. In some embodiments, the computer system 160 transmits the image information to the welding helmet 12 instead of or in addition to the welding system 14. In some embodiments, the computer system is incorporated into or is integral to the welding system 14.

Figure 12:
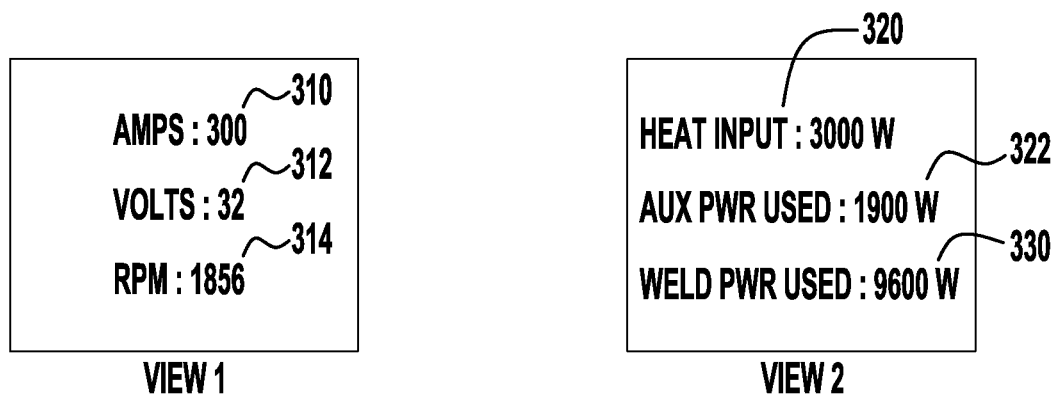
FIG. 12 illustrates exemplary views of information that can be displayed.

In some embodiments, the image information seen by the welder is configurable. For example, the computer system 160 and/or the welding system 14 can be configured with different "views" or image screens that the welder can select. For example, as illustrated in FIG. 12, the welding information can be presented to the welder using several image screens or "views." View 1 can represent real-time operating parameters of an engine-driven welder such as, e.g., welder output amps 310, welder output volts 312, engine speed 314, etc. A second "view," View 2, can represent performance totals such as, e.g., welding heat input 320, Auxiliary Power Used 322, Welding Power Used 324, etc. In other exemplary embodiments, other data can be shown. For example, the HUD can display engine related information such as RPM, engine temperature, oil pressure, air compressor output pressure (if equipped), and any trouble codes from an engine control computer to allow the welder to be warned of any issues. The views can be customized to meet the welder's needs. For example, the views can be customizable based on the type of welding (TIG, MIG, etc.), material being welded (steel, aluminum, etc.), type of weld (fillet, butt joint, etc.), or on some other basis. In addition, the views can be customized for each welder. For example, after a welder identifies himself or herself by, e.g., logging into the computer system 160 or welding system 14, by using a token such as, e.g., a RFID tag, or by some other means, the computer system 160 and/or the welding system 14 can display a set of "views" that are specific to the welder, e.g., based on the welder's preferences, experience level, etc.

The welder can turn the HUD 135, 235 on and off and scroll through the "views" using controls (not shown) located on the welding helmet 12. Alternatively, or in addition, the welder can control the HUD 135, 235 using voice commands. The welding helmet 12 can include a microphone system 140 (see FIG. 7) that picks up audio command from the welder. The microphone system 140 can then relay the audio commands to welding system 14 and/or computer system 160 using communication device 150. The welding system 14 and/or the computer system 160 interprets the commands and sends the appropriate instructions and information to the information generating device 129, 229. Information generating device 129, 229 will then control projector 128 and/or combiner 234 based on the received information and instructions. For example, a welder can say "SHOW CURRENT" and the system will display the welding current. Other voice commands can be used to allow the user to display the desired information. These voice commands can be used, prior to, during or after the completion of a welding process. In addition to the commands discussed above, the welder can adjust the size and location of the image window 136, the brightness of the image display, the color of the image display, etc. In some embodiments, the welder can control the opacity of the image to make the image more or less transparent, e.g., from nearly 100% transparent to 100% opaque. Along with welder adjustments, some display parameters such as, e.g., brightness, opacity, color, etc. can be adjusted automatically by at least one of information generating device 129, 229, computer system 160 and welding system 14 based on whether the welding arc is sensed and/or the level of ambient light in the room.

Figure 13:
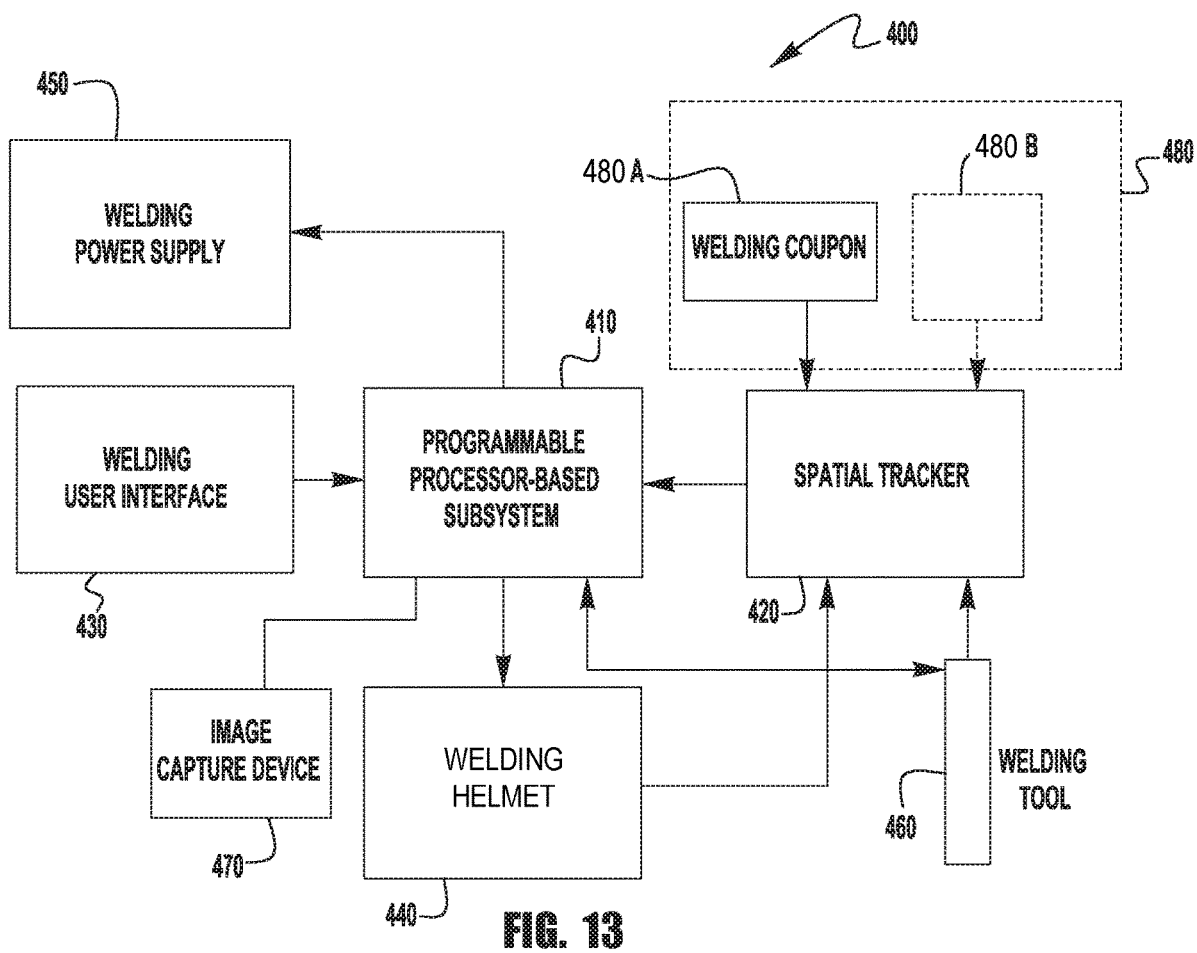
FIG. 13 illustrates a schematic block diagram of a welding system according to another exemplary embodiment of the invention.
Figure 14:
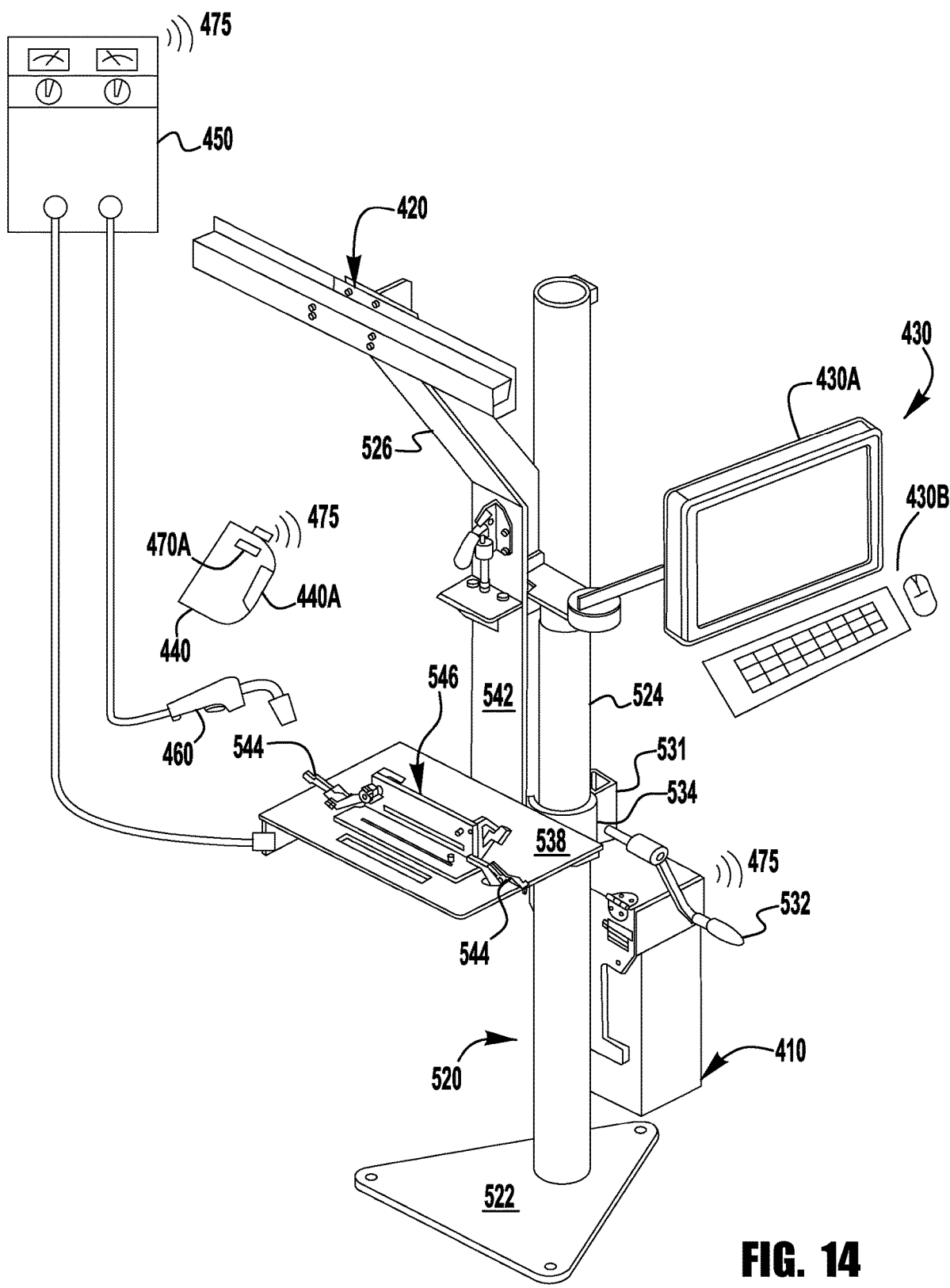
FIG. 14 illustrates a schematic view of the welding system in FIG. 13.

In another exemplary embodiment, as seen FIG. 13, system 400 provides real-time visual feedback while the user performs a weld, which can include, e.g., a real-world weld, a simulated weld, or a combination of real-world weld and a simulated weld. That is, the system 400 can be used in the training of welders in environments where students practice welds on real-world and/or simulated welding coupons and workpieces. Preferably, when performing simulated welding, the simulated objects can include, but are not limited to, the welding arc, the welding puddle, and/or the welding coupon/workpiece. As discussed below, the simulated objects are then displayed, projected or mapped onto the HUD, combiner, head-mounted display, or equivalent. The workpieces, real-world and/or simulated, can include, e.g., simple objects such as plates, pipes, etc. and complex objects such as parts, devices, and components used in, e.g., machinery. Preferably, some exemplary embodiments can be used to perform welds in the field, e.g., at a manufacturing site, at a construction site, etc. FIGS. 13 and 14 provide an overview of a system 400 in accordance with exemplary embodiments of the invention. System 400 includes a logic processor-based subsystem 410, which may be programmable and operable to execute coded instructions for generating the visual cues and audio cues to be overlaid and aligned with a digital image of the welding environment 480 and/or displayed on a combiner of a HUD. The visual and audio cues, whether by themselves or as part of a composite image stream (e.g., video stream) with the welding environment 480, are then transmitted to the user (welder) via face-mounted display device 440A mounted on welding helmet 440. As discussed below, depending on the type of display, the visual cues and/or a digital image (video) of the welding environment 480 are presented to the user. Preferably, as discussed further below, the visual cues can be aligned with preferred areas such as, e.g., corners and along the sides of the display device 440A and/or the visual cues can be aligned with objects such as the welding tool 460, welding coupon 480A or workpiece 480B, contact tip, nozzle, etc. that are visible on the display device 440A.

In addition to displaying visual cues and displaying the welding environment 480, the display device 440A can also playback or display a variety of media content such as videos, documents (e.g., in PDF format or another format), audio, graphics, text, or any other media content that can be displayed or played back on a computer. This media content can include, for example, instructional information on welding that the trainee can review prior to performing a weld (e.g., general information on welding, information on the specific weld joint or weld procedure the user wishes to perform, etc.). The media content can also include information on the trainee's performance or the quality of the weld after completion of the weld or training exercise, and/or audio/visual information provided to the trainee during the weld (e.g., if the visual cues are turned off and the trainee's performance is a problem, the system can display and/or provide audio information suggesting that the visual/audio cues be turned on).

System 400 further includes sensors and/or sensor systems, which may be comprised of a spatial tracker 420, operatively connected to the logic processor-based subsystem 410. As discussed below, the spatial tracker 420 tracks the position of the welding tool 460 and the welding helmet 440 relative to the welding environment 480. The system 400 can also include a welding user interface 430 in communication with the logic processor-based subsystem 410 for set up and control of the system 400. Preferably, in addition to the face-mounted display device 440A, which can be connected to, e.g., the logic processor-based subsystem 410, the system 400 also includes an observer/set-up display device 430A connected to, e.g., the welding user interface 430. Each display device 440A, 430A can provide a view of the welding environment 480 that has been overlaid with visual cues. Preferably, the system 400 also includes an interface that provides communication between programmable processor-based subsystem 410 and a welding power supply 450 in order to receive welding parameters such as, e.g., voltage, current, power, etc. In some exemplary embodiments, the system 400 includes a video capture device 470 that includes one or more cameras, e.g., digital video cameras, to capture the welding environment 480. The video-capture device 470 can be mounted on the welding helmet 440, similar to helmet 12 discussed above with reference to FIGS. 2 and 5. The signal from the video capture device 470 provides the field of view that the user sees while welding. The signal from the video-capture device 470 can be sent to the programmable processor-based subsystem 410 for processing of the visual cues. Depending on the type of welding helmet 440, either the visual cues or both the visual cues and video of the welding environment 480 are sent to the face-mounted display 440A. For example, in the case where the welding helmet includes a see-through lens, e.g., an auto-darkening lens (see e.g., helmet 12 of FIG. 11), the video cues are mapped and transmitted to the combiner so as to match the field of view of the user through the face-mounted display 440A.

In various exemplary embodiments, the spatial tracker 420 measures the motion of welding tool 460 and/or welding helmet 440 and gathers process data during the welding exercises. Preferably, the spatial tracker 420 uses one or more of the following tracking systems: a single or multiple camera based tracking system (e.g., based on point cloud image analysis), a magnetic-field based tracker, an accelerometer/gyroscope based tracker, an optical tracker, an infrared tracker, an acoustic tracker, a laser tracker, a radio frequency tracker, an inertial tracker, an active or passive optical tracker, and a mixed reality and simulation based tracking. Still, other types of trackers may be used without departing from the intended scope of coverage of the general inventive concepts. The exemplary embodiments of the invention are applicable to a wide range of welding and related processes including, but not necessarily limited to, GMAW, FCAW, SMAW, GTAW, cladding and cutting. For brevity and clarity, the description of system 400 will be provided in terms of welding, but those skilled in the art understand that the description will also be valid for other operations such as cutting, joining, cladding, etc.

Preferably, the logic processor-based subsystem 410 includes at least one computer for receiving and analyzing information captured by the spatial tracker 420, image capture device 470 and welding process data transmitted by the welding power supply 450. During operation, the computer is typically running software that includes a welding regimen module, an image processing and rigid body analysis module, and a data processing module. The welding regimen module includes a variety of weld types and a series of acceptable welding process parameters associated with creating each weld type. Any number of known or AWS weld joint types and the acceptable parameters associated with these weld joint types may be included in the welding regimen module, which can be accessible and configurable by user, a welding instructor, etc. to add modify or delete any information in the welding regimen module. In addition to known weld types, the logic processor-based subsystem 410 can import weld joints and/or specific welds corresponding to custom parts, devices, components, etc. into the welding regimen module. For example, the logic processor-based subsystem 410 can import design model information, e.g., CAD format (2-D or 3-D) (or another type of design format), of any complex custom part, device, component, etc. that is welded as part of the fabrication process (e.g., parts, devices, components, etc. used in any industrial, manufacturing, agricultural, or construction application or any other application). Once imported, the number and types of joints used in manufacturing the custom part, device, component, etc. can be identified and stored in the welding regimen module as a custom weld type. The acceptable parameter limits associated with these weld joint types can be input by, e.g., the instructor or, preferably, included in the design file (e.g., CAD file) from the manufacturer, and are then read by the logic processor-based subsystem 410. As an illustrative example, the logic processor-based subsystem 410 can import a design of an automobile axle, e.g., in 2-D or 3-D CAD format. The number and type of joints used in manufacturing the axle can be identified (either by, e.g., the instructor, or automatically read in as part of the file, e.g., 2-D or 3-D CAD format) and stored in the welding regimen module as a custom weld type or types. As with the known or AWS weld types, the acceptable parameters associated with the custom weld types are also stored in the welding regimen module. Preferably, information for the custom part, device, component, etc. is also used by embodiments of the logic processor-based subsystem 410 for workpiece recognition and auto-calibration of the system as discussed below.

The weld process and/or type selected by the user prior to welding determine which acceptable welding process parameters are used for any given welding exercise. The object recognition module is operative to train the system to recognize known rigid body objects, which can include two or more point markers, and then calculate position and orientation data for, e.g., welding tool 460 and welding helmet 440 as a manual weld is completed by the user. Preferably, along with known rigid body objects, the object recognition module can also be uploaded or configured with information for recognizing custom parts, devices, components, etc. discussed above. The data processing module compares the information in the welding regimen module to the information processed by the object recognition module and outputs feedback to the user. For example, the logic processor-based subsystem 410 can provide any type of feedback to the user (typically in real time) via various means including, but not limited to, one or more of in-helmet visual feedback, visual feedback on a separate monitor, audio feedback (e.g., tones, coaching, alarms) via speakers, and additional visual, audio, or tactile feedback using the welding tool (e.g., torch, welding gun). For example, the real-time visual feedback can be provided to the user and/or an observer as the user welds on a welding coupon 480A or a workpiece 480B, each of which can have a range of configurations, including large sizes, various joint types, pipe, plate, and complex shapes and assemblies. Preferably, measured parameters, which are provided as the feedback, include, but are not limited to, aim, work angle, travel angle, tool standoff, travel speed, bead placement, weave, voltage, current, wire feed speed, arc length, heat input, gas flow (metered), contact tip to work distance (CTWD), and deposition rate (e.g., lbs./hr., in./run). Preferably, the face-mounted display 440A and/or welding user interface 430 with display device 430A allows the user and/or an observer to visualize the processed data in real time and the visualized data is operative to provide the user with useful feedback regarding the characteristics and quality of the weld. In some exemplary embodiments, the feedback data is automatically recorded and saved in a data storage device, e.g., hard disk drive, or other known storage means by logic processor-based subsystem 410.

Preferably, the logic processor-based subsystem 410 can include memory, e.g., RAM, ROM, EPROM, hard disk drive, CD ROM, removable drives, flash memory, etc., that can be pre-populated with specific welding procedures, which can include procedures that have been customized, e.g., by an experienced welder, a manufacturer, etc. The procedures can include information related to the visual and audio cues such as the criteria for changing the attributes of the visual and audio cues. The procedures can include information on the target values and target ranges for parameters such as aim, work angle, travel angle, tool standoff, travel speed, bead placement, weave, voltage, current, wire feed speed, arc length, heat input, gas flow (metered), contact tip to work distance (CTWD), deposition rate (e.g., lbs./hr., in./run), etc. based on the type of welding process, the type of the welding gun, the type and orientation of the weld joint, the type of material being welded, the type of the electrode, the type and size the filler wire (if any), etc. Preferably, the logic processor-based subsystem 410 can perform real-time and a post-weld analysis that scores the performance of the welder, user. Preferably, based on the analysis, the logic processor-based subsystem 410 can provide other information such as the potential existence of faults in the weld (e.g., porosity, incomplete fusion (not enough penetration), crack in the weld, undercut, weld profile is too thin, weld profile is too thick, etc.) and how to avoid the faults in real-time and/or in a post-weld analysis. Preferably, the progress of the user is tracked over time, which can be a beneficial aid to a trainer in identifying areas where the user may need additional teaching. However, exemplary embodiments of the invention are not limited to a traditional training environments where welders, whether beginners, intermediate or experienced, practice welding on welding coupons such as, e.g., welding coupon 480A.

Exemplary embodiments of the invention can be used in actual working environments and the visual and audio cues, which are discussed further below, aid the welder in performing the weld. For example, a beginner can use the visual and audio cues to make sure the welding gun is oriented properly and the travel speed is correct. Experienced welders can also benefit from the visual and audio cues when, e.g., welding on a workpiece and/or using a filler wire whose material is new to the welder, working at an orientation that is unfamiliar, when using a non-traditional welding procedure, etc.

FIG. 14 provides an illustrative view of a welding application incorporating system 400 in accordance with an exemplary embodiment the present invention. As shown in FIG. 14, stand 520 includes a substantially flat base 522 for contact with a floor or other horizontal substrate, rigid vertical support column 524, tracking system (e.g., camera or imaging device) support 526, and rack and pinion assembly 531 for adjusting the height of the tracking system support 526. In some exemplary embodiments, a motor operated assembly can be used for adjusting the height. The portable stand 520 can be used in a training environment where the user performs welding operations (real-world and/or simulated) on welding coupon 480A and/or in a manufacturing environment in which welding is performed on workpiece 480B which can be small to medium sized objects. Of course, those skilled in the art would understand that with appropriate modification, the system 400 can also be used on larger workpieces and in construction sites. In some embodiments, e.g., when used for training, the stand 520 and attached equipment can be portable or at least moveable from one location to another, therefore the overall footprint of base 522 is relatively small to permit maximum flexibility with regard to installation and use. In other environments, e.g., in a manufacturing shop, the stand 520 and attached equipment can be fixed at a particular location, e.g., a welding booth, which can have other equipment such as an exhaust hood, Preferably, the stand 520 and attached equipment allow for any suitable arrangement of workpieces including, but not limited to, flat, horizontally, vertically, overhead, and out-of-position oriented workpieces. In the exemplary embodiment shown in FIG. 14, stand 520 is depicted as a unitary or integrated structure that is capable of supporting some of the components of the system 400. In other embodiments, stand 520 is absent and the various components of the system 400 are supported by whatever suitable structural or supportive means may be available. Thus, within the context of this disclosure, "stand" 520 is defined as any single structure or, alternately, multiple structures that are capable of supporting one or more of the components of welding system 400.

Figure 15:
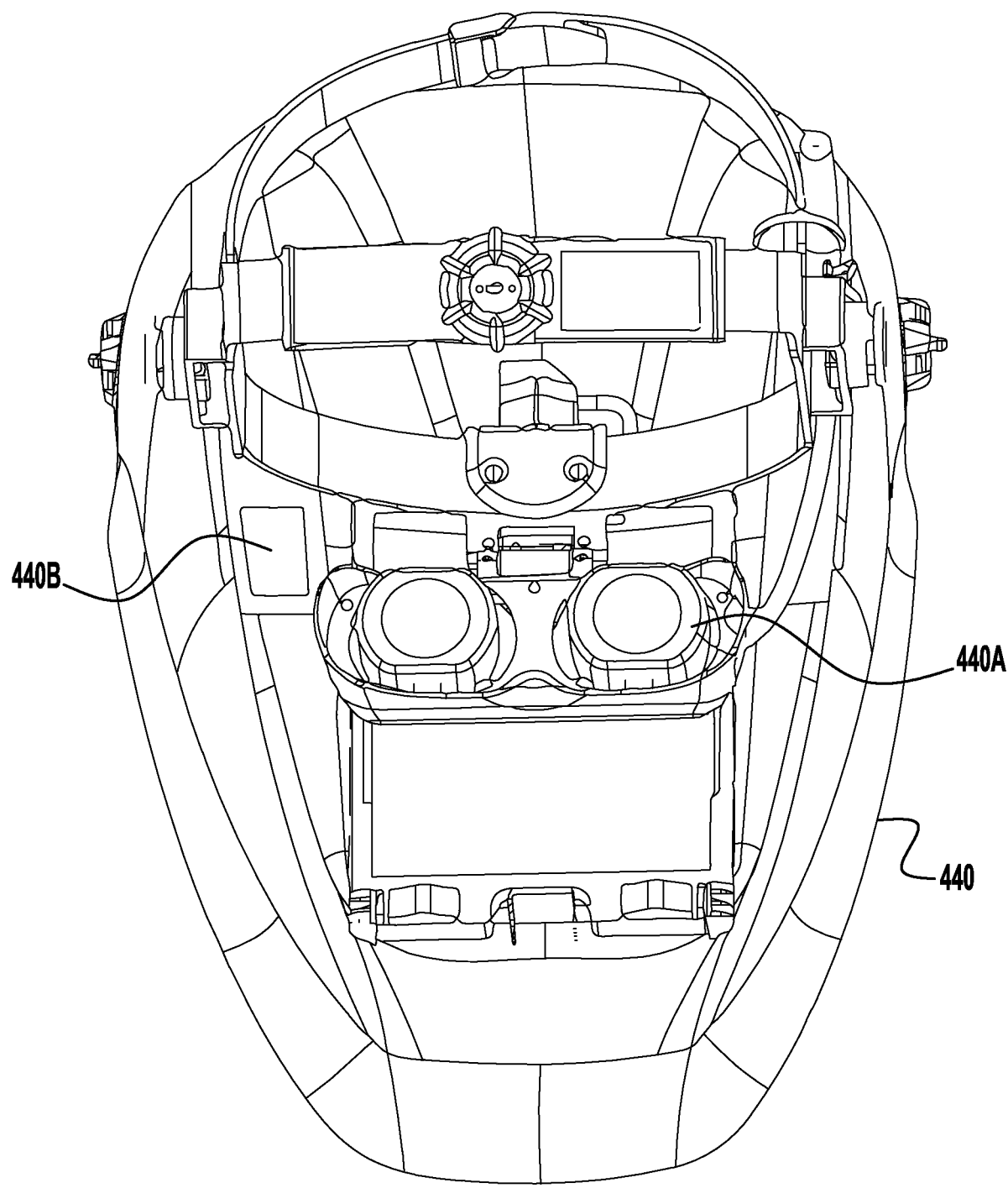
FIG. 15 illustrates a perspective view of a welding helmet with a face-mounted display device.
Figure 16A:
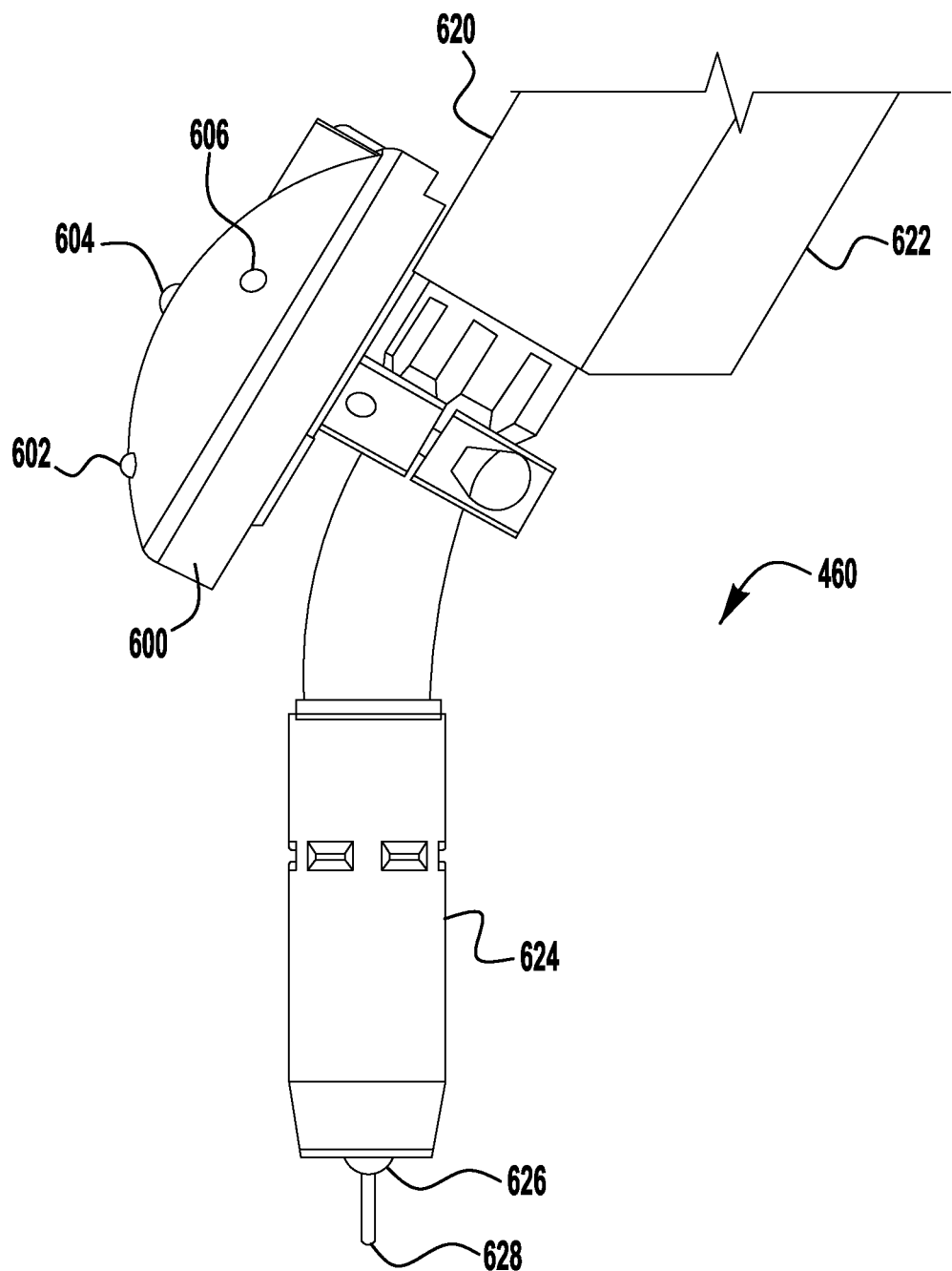
FIG. 16A illustrates an exemplary welding tool showing the placement of point markers used to define the rigid body.
Figure 16B:
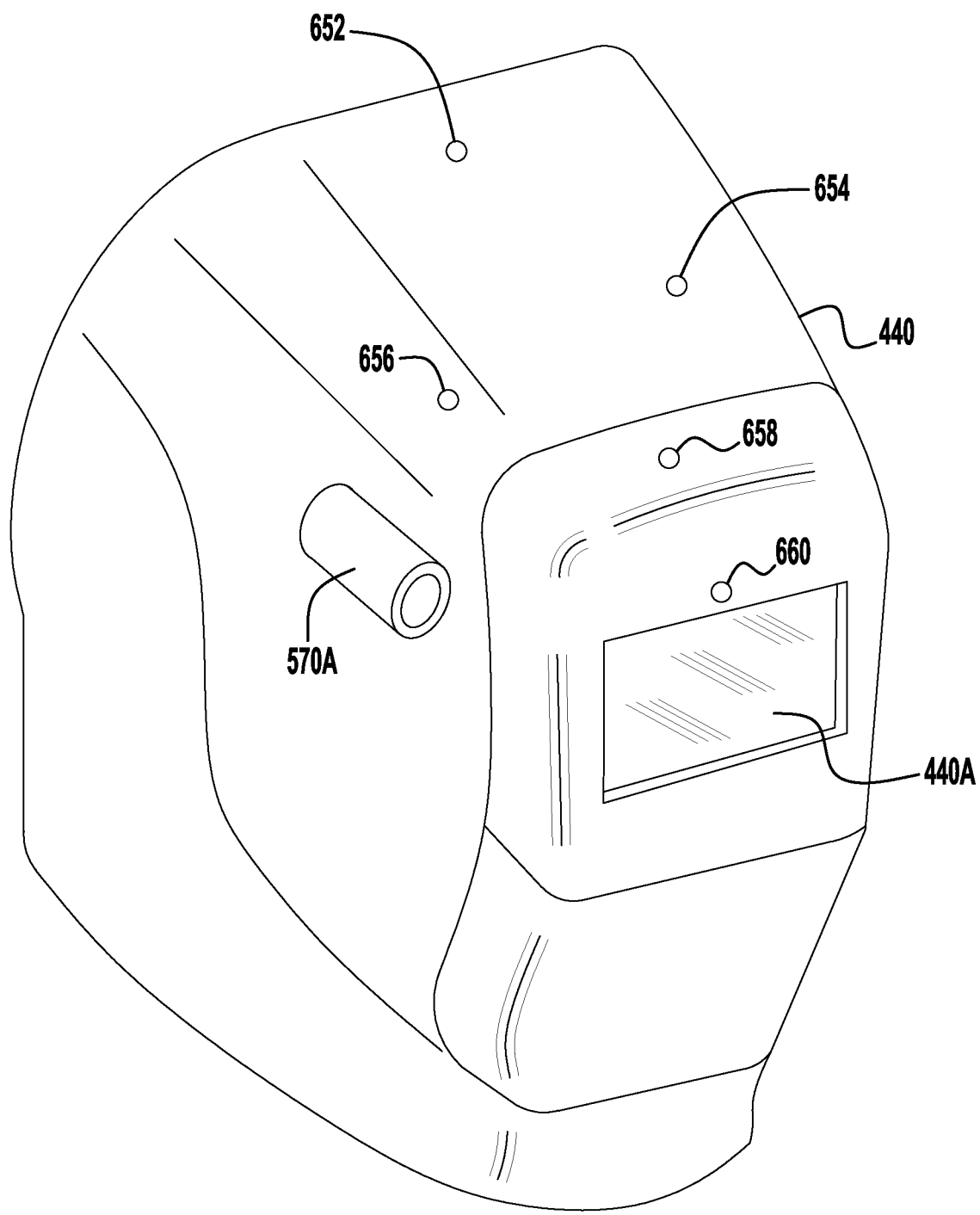
FIG. 16B illustrates an exemplary welding helmet showing the placement of point markers used to define the rigid body.

With reference now to FIG. 15, an example of welding helmet 440 with face-mounted display device 440A will now be described. The face mounted display device 440A may be integrated into a welding helmet 440. Optionally, instead of an integrated display device, the system 400 can include a display device that the user wears as glasses. The face mounted display device 440A can include two high-contrast SVGA 3D OLED micro-displays capable of delivering fluid full-motion video in the 2D and frame sequential video modes. Preferably, images (e.g., video) of the welding environment 480 are provided and displayed on the face mounted display device 440A via video capture device 470 having cameras 470A, 470B mounted on welding helmet 440, e.g., mounted as shown in FIGS. 2, 5 and 16B. The images from the welding environment 480 can be overlaid with visual cues as discussed below. Preferably, the logic processor-based subsystem 410 provides stereoscopic video to the face mounted display device 440A, enhancing the depth perception of the user. A zoom (e.g., 2×, 3×, etc.) mode may also be provided as an aid to the user. In some embodiments, the face-mounted display device 440A is a see-through type display and is constructed similar to HUD 235 of FIG. 11 with a combiner and lens, e.g., an auto-darkening lens, as discussed above.

The helmet 440 operatively connects to the logic processor-based subsystem 410 and the spatial tracker 420 via wired or wireless means, e.g., in FIG. 14, wireless network 475 is used. As discussed below, sensors (either passive or active) can be attached to the welding helmet 440 thereby allowing the face mounted display device 440A to be tracked with respect to the 3D spatial frame of reference created by the spatial tracker 420. In this way, movement of the welding helmet 440 responsively alters the visual cues seen by the end user such that the visual cues are aligned with the objects, e.g., welding tool 460, welding coupon 480A, workpiece 480B, etc., in the field of view of the user. Preferably, the face-mounted display 440A can display menu items for configuration and operation of system 400. Preferably, selection of the menu items can occur based on controls mounted on the welding tool 460 (e.g., buttons, switches, knobs, etc.). Alternatively, or in addition to displaying the menu items on the face-mounted display device 440A, the menu items can be displayed on display device 430A of welding user interface 430 and the selections can be made using traditional input devices such as, e.g., a mouse and keyboard. In some embodiments, the selection of the menu items can be accomplished voice activated commands. For example, the menu screen can be displayed by saying, e.g., "MENU" and navigating the menu screen can be accomplished by saying, e.g., "UP, DOWN, LEFT, RIGHT" and selection can be accomplished by saying, e.g., "SELECT." Preferably, the selection of the menu items can be done by tracking the eyes of the user. As the user's eyes focus on a menu item, the menu item is highlighted. Preferably, selection of the highlighted menu item is accomplished by blinking the eyes, e.g., a single-blink, double blink, etc. Of course, any combination of welding tool controls, audio input and eye tracking input can be used to navigate through the menu items. For example, the eyes can be used to highlight the menu item and voice commands and/or the welding tool controls are used to select the highlighted item.

The welding helmet 440 may further include speakers 440B, allowing the user to hear audio cues. Different sounds can be provided depending on if certain welding or performance parameters are within tolerance or out of tolerance. For example, a predetermined tone can be provided if the travel speed is too high and a different predetermined tone can be provided if the travel speed is too low. Sound may be provided to the user via speakers 440B, which may be earbud speakers or any other type of speakers or sound generating device, mounted in the welding helmet 440 and/or mounted separately, e.g., on the welding table. Still, any manner of presenting sound to the end user while engaging in welding activity may be chosen. It is also noted here that other types of sound information may be communicated through the speakers 440B. Examples include verbal instructions from an instructor or an expert, in either real time or via prerecorded messages. Prerecorded messages may be automatically triggered by particular welding activity. Real time instructions may be generated on site or from a remote location. Still, any type of message or instruction may be conveyed to end user.

Preferably, determining the orientation of the welding tool 460 and the welding helmet 440 includes capturing images of the respective objects with one or more off-the-shelf high-speed-vision cameras, which can be mounted on tracking system support 526 of stand 520 or another fixed location relative to the welding environment 480. Preferably, the processing of the captured images includes creating an image file at many (e.g., over 100) frames per second. Preferably, the one or more cameras typically capture at least two point markers located in a fixed geometric relationship to one another on each of the respective objects, welding tool 460 and welding helmet 440, 22. Of course, other objects in the welding environments 480 such as the welding coupon 480A and workpiece 480B can include point markers so that their position and orientation can also be determined based on the images captured by the cameras. Preferably, the processing of the captured images is performed in the spatial tracker 420 and/or the logic processor-based subsystem 410.

As discussed above, tracking of the objects in 3-D space, including the welding environment 480 can be accomplished by using point markers on the objects, e.g., welding tool 460, welding helmet 440, welding coupon 480A, workpiece 480B, etc. For example, as seen in FIG. 16A, target 600 is mounted on welding tool 460. A rigid body point cloud (i.e., a "rigid body") is constructed by attaching active or passive point markers 602, 604, and 606 (and possibly additional point markers) to the upper surface of target 600. Passive point markers can be, e.g., reflective markers such as e.g., reflective tape or stickers that are adhesively attached to target 600 or attached by other known means. Active markers can include LEDs (e.g., infrared LEDs), or other sensors that are, e.g., fastened to the target 600. Of course, other point marker placements are possible and fall within the scope of the general inventive concepts. Target 600 can include a power input if the point markers used are active and require a power source. Of course, the point markers can be attached or mounted directed on the "rigid body," e.g., welding tool 460 or welding helmet 440, if desired, rather than using a separate target. For example, as shown in FIG. 16B, point markers 652, 654, 656, 658 and 660 are placed on the welding helmet 440. The passive or active point markers are affixed to the target 600 and/or directly to welding tool 460 and welding helmet 440 in a multi-faceted manner so that a wide range of rotation and orientation changes can be accommodated within the field of view of the imaging system. The point markers corresponding to the welding tool 460 and welding helmet 440 are respectively correlated or calibrated so as to form "rigid bodies," i.e., the body 620, trigger 622, nozzle 624 and tip 626 of the welding tool 460 have a known spatial relationship to each other and the display 440A and the body of welding helmet 440 have a known spatial relationship to each other. In addition, after calibrating the "rigid body," additional calibration steps may be needed to calibrate the "rigid body" to other points. For example, in the case of the welding tool 460, the "rigid body" formed by points 602, 604, and 606 can then correlated or calibrated to point 628 using a known distance between point 628 and 626. Calibration of welding tools and welding helmets to tracking systems is known in the art and thus, for brevity will not be further discussed. During operation, spatial tracker 420 uses a tracking system such as e.g., Optitrack Tracking Tools or similar hardware/software to locate and track the rigid bodies.

The image processing then includes frame-by-frame point cloud analysis of the rigid bodies (i.e., the calibrated targets, which can include welding tool 460 and welding helmet 440) that includes three or more point markers. Upon recognition of a known rigid body, position and orientation are calculated relative to the camera origin and the "trained" rigid body orientation. Calibrating and "training" the spatial tracker 420 to recognize the position and orientation in three-dimensional space of rigid bodies such as the welding tool 460 and welding helmet 440 is known in the relevant art and thus, for brevity, will not be discussed in detail. For example, the spatial tracker 420 can include any suitable data capturing system such as, for example, the Optitrack Tracking Tools (provided by NaturalPoint, Inc. of Corvallis, Oreg.) or a similar commercially available or proprietary hardware/software system that provides three-dimensional marker and six degrees of freedom object motion tracking in real time. Such technologies typically utilize reflective and/or light emitting point markers arranged in predetermined patterns to create point clouds that are interpreted by system imaging hardware and system software as "rigid bodies," although other suitable methodologies are compatible with this invention. The system imaging hardware and software can be incorporated into logic processor-based subsystem 410.

Preferably, more than one camera is used to track welding tool 460 and welding helmet 440. Capturing and comparing the images from two or more cameras allows for a substantially accurate determination of the position and orientation in three-dimensional space of welding tool 460 and welding helmet 440. Images are typically processed at a rate of more than 100 times per second. One of ordinary skill in the art will appreciate that a lesser sampling rate (e.g., 10 images/sec.) or a greater sampling rate (e.g., 1,000 images/sec.) could be used. The output aspect of image processing includes creation of a data array that includes x-axis, y-axis, and z-axis positional data and roll, pitch, and yaw orientation data, as well as time stamps and software flags. Text files (including 6-D data for the welding tool 460 and welding helmet 440) may be streamed or sent by the spatial tracker 420 at a desired frequency to the programmable processor-based subsystem 410 or, in some embodiments, be generated by the logic processor-based subsystem 410. While the above exemplary embodiment of spatial tracker 420 is described as a single or multiple camera based tracking system based on point cloud image analysis, those skilled in the art understand that other type of tracking systems can be used, e.g., a magnetic-field based tracker, an accelerometer/gyroscope based tracker, an optical tracker, an infrared tracker, an acoustic tracker, a laser tracker, a radio frequency tracker, an inertial tracker, an active or passive optical tracker, and mixed reality and simulation based tracking. In addition, while the cameras 470 A, B are discussed above as providing a "field of view" of the user to the system 400, the cameras 470 A, B can also be configured to track objects in the welding environment 480, instead of the cameras on tracking system 526. Of course, an appropriate alternate fixed reference point in the welding environment 480 must be used because the cameras 470 A, B will move with the movement of the user.

Figure 17:
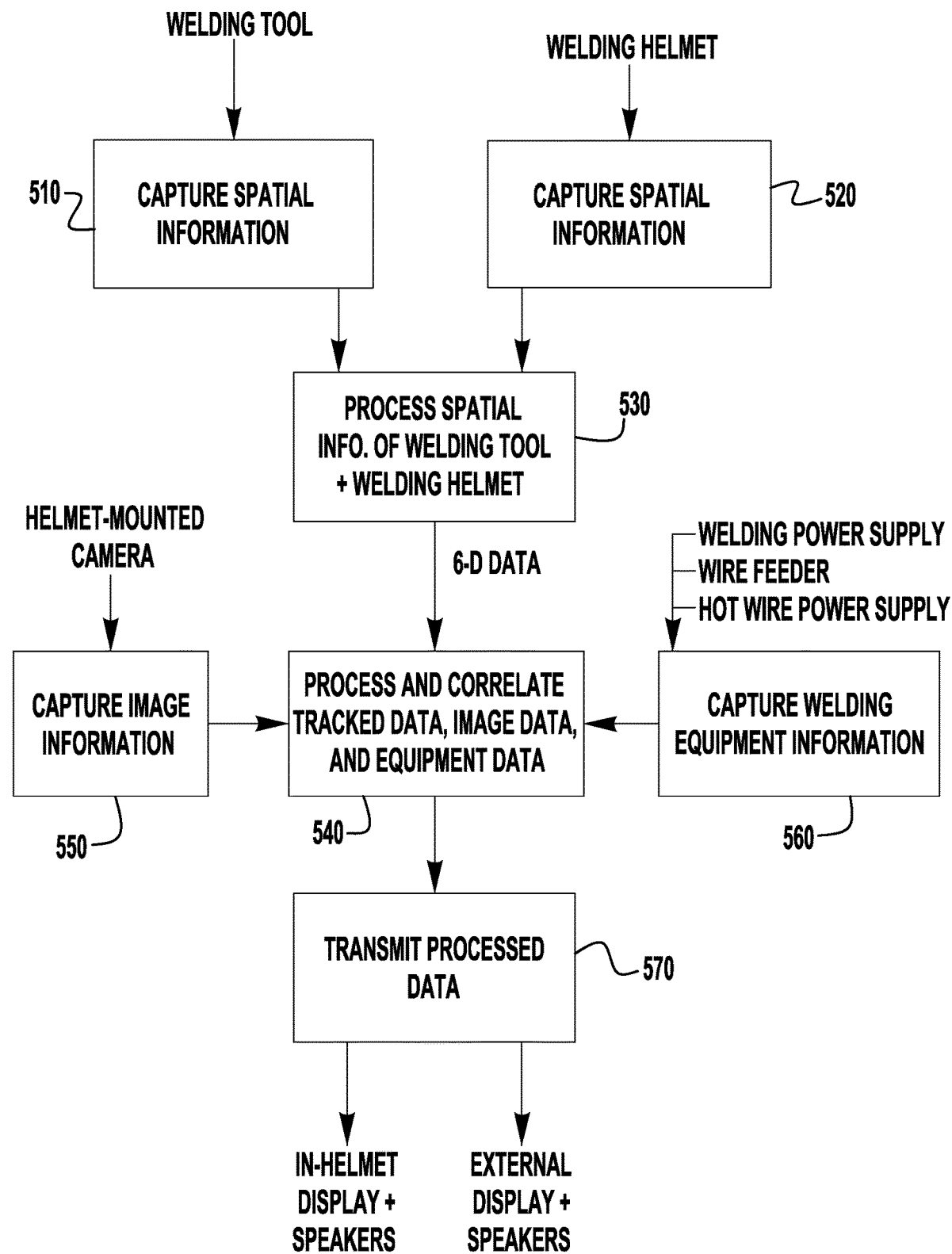
FIG. 17 illustrates a flow chart showing the flow of information in an exemplary embodiment of the invention.

In an exemplary embodiment, FIG. 17 illustrates the basic flow of information in the system 400. For clarity, the information flow is described with an exemplary embodiment using tracking cameras. However, as discussed above, other types of tracking systems can be used. In block 510, the system 400 captures spatial information regarding the position, orientation and motion of the welding tool 460. In block 520, the system 400 also captures the position, orientation and motion of the welding helmet 440 with face-mounted display device 440A. In block 530, the spatial tracking information of the welding tool 460 and the welding helmet 440 is processed to determine the position and orientation of the welding tool 460 and welding helmet 440 in three-dimensional space relative to the welding environment 480 and preferably includes creating 6-D data files for the welding tool 460 and welding helmet 440.

In block 550, the digital image data (e.g., video) from one or more cameras mounted, e.g., on the welding helmet is captured for processing in, e.g., data processing block 540. In block 560, welding process parameters such as those transmitted by welding equipment, e.g., welding power supplies (e.g., current, voltage, etc.), wire feeders (wire feed speed, etc.), hot-wire power supplies (current, voltage, temperature, etc.), or some other piece of welding equipment are captured for processing in block 540. Preferably, the welding process parameters can also include heat input (which can be calculated, e.g., using welding current, welding voltage and travel speed), arc length (which can be determined based on welding voltage) and other calculated welding parameters.

Preferably, the data processing in block 540 includes correlating the view of the welding environment 480 from the helmet-mounted cameras to the tracking data processed in block 530, i.e., the 6-D data of the tracked welding tool and the tracked welding helmet. For example, the position and orientation information of objects such as the welding tool 460, welding coupon 480A and workpiece 480B are mapped to the image data captured by image capture device 470. Preferably, the welding process parameters from block 560 are processed with the mapped image and tracking data to create an image stream showing the welding environment with visual cues.

In some exemplary embodiments, audio cues based on the welding process parameters and the tracked data are also generated in block 540 to create an audio stream that can be transmitted to the welding helmet 440 along with the image stream. Preferably, the image stream and audio stream are combined to create a composite audiovisual stream that is sent to welding helmet 440. Generally, the data processing step in block 540 includes algorithms to generate target values and target ranges for welding parameters such as, e.g., aim, work angle, travel angle, tool standoff, travel speed, bead placement, weave, voltage, current, wire-feed speed, arc length, heat input, gas flow (metered), contact tip to work distance (CTWD), deposition rate, frequency of TIG filler addition, using algorithms specific to a selected welding process, joint type, material being welded, joint orientation, etc. The data processing step in block 540 also includes algorithms to generate visual and audio cues based on the welding process parameters and tracked data and algorithms to properly place the visual and audio cues on the in-helmet display as discussed below.

As seen in step 570, the digital image data and audio data processed in block 540 is transmitted to external devices. The image data can be viewed on, e.g., a monitor, in-helmet display, heads-up display, or combinations thereof and audio data (e.g., audio coaching, alarms, tones, etc.) may be directed to external speakers, in-helmet speakers, ear buds, etc. For example, the digital image data and audio data can be transmitted to the face-mounted display 440A and speakers 440B of welding helmet 440 and optionally to display device 430A of welding user interface 430. The digital image data and audio data include visual and audio cues, respectively, relate to welding data. For example, the visual and audio cues relate to, but are not limited to, aim, work angle, travel angle, tool standoff, travel speed, bead placement, weave, voltage, current, wire-feed speed, arc length, heat input, gas flow (metered), contact tip to work distance (CTWD), deposition rate, frequency of TIG filler addition. Based on the input data, the logic processor-based subsystem 410 can also generate tactile feedback that is sent to the welding tool 460 if so configured. For example, a vibrator on the welding tool 460 can be triggered if the welding process goes into an alarm condition. In addition, the welding tool 460 can provide visual feedback using e.g., LCDs, LEDs, etc. Preferably, the feedback, whether visual, audio or tactile, is presented to the user in real time as the user is performing a weld on, e.g., the real and/or simulated welding coupon 480A or workpiece 480B.

In preferred embodiments, the visual and audio cues can be provided to the user to aid the user in the welding process. The visual cues can appear as alphanumeric characters, symbols, graphics, icons, colors, etc. The audio cues can be in the form of tones, alarms, buzzers, audio instructions (either live or pre-recorded and either a human voice or a computer-generated voice). The visual cues can be displayed in any desired location on the display of the face-mounted display device 440A. For example, FIG. 18 illustrates an image of the welding environment 480 on display 441 as seen by the user when viewing through the face-mounted display device 440A. Depending on the type of welding helmet, the display 441 is a monitor that can show a video of the welding environment 480 or is a HUD with an auto-darkening welding lens with combiner. Preferably, the visual cues can be directly mapped to any desired location on the display 441, e.g., see 720 where arc length and heat input are directly mapped on display 441. In some embodiments, the visual cues are provided in one or more image windows 702 that can be placed in the corners, along the top, bottom or side of the display 441 or any other desired location on the display 441. Preferably, related visual clues can be grouped together in a window 702. For example, current, voltage and wire feed speed can be grouped in a window 702. This allows the user to treat all the visual cues in a window as a single unit to expedite the welding setup. The image windows 702 can be moved as desired, e.g., by using appropriate controls on the welding tool 460, voice command, etc. The information provided by the visual cues can relate to, but are not limited to, parameters such as, e.g., aim, work angle, travel angle, tool standoff, travel speed, bead placement, weave, voltage, current, wire feed speed, arc length, heat input, gas flow (metered), contact tip to work distance (CTWD), TIG filler input frequency, etc.

In some embodiments, as shown in FIG. 18, the visual cues 700 can be overlaid on or adjacent to an object in the welding environment 480 as viewed on display 441. For example, the visual cues 700 can be linked to the welding tool 460 in the image stream sent to display device 440A so as to be "attached" to the welding tool, i.e., the visual cues 700 move with the welding tool 460. Preferably, the visual cues 700 can be attached to any object in the welding environment 480, even if the object is not designed to move, such as e.g., the welding coupon 480A or workpiece 480B. Preferably, the visual cues 700 are semi-transparent in that the user will be able to see objects in the welding environment that are covered by the visual cue. In the case where the user can directly observe the welding environment 480, the visual cues 700 can be "attached" to a location on the screen where the relevant object, e.g., welding tool 460, weld coupon 480A, workpiece 480B, weld joint, etc., is calculated to be in the "field of view" of user based on the tracking information from the spatial tracker 420. In either type of face-mounted display, based on the 6-D information from spatial tracker 420, the logic processor-based subsystem 410 can calculate the X and Y coordinates on the video image or display 441 where an object such as, e.g., welding tool 460, will be located, and the subsystem 410 can then map the visual cues 700 to appropriate X and Y coordinates on the video image or display 441 corresponding to the object. For example, as seen in FIG. 18, visual cues 700 for CTWD 704, work angle 706 and travel speed 708 are overlaid on the welding tool 460. As the welding tool 460 moves, the visual cues CTWD 704, work angle 706 and travel speed 708 will move with the welding tool 460 so as to maintain the same relative position to the welding tool 460. In contrast, as discussed above, other visual cues can be fixed to a location on the display 441. For example, visual cues such as welding voltage 712, welding current 714 and wire feed speed 716 are fixedly mapped to a corner of display 441 in a window 702 and visual cues 720 are fixedly mapped to a position on the display 441. The visual cues can also be fixed to a location corresponding to a fixed object such as welding coupon 480A or workpiece 480B. The visual cues 700 can be mapped to any desired location on the display 441. Preferably, the logic processor-based subsystem 410 maps the visual cues 700 such that certain aspects of the welding operation such as, e.g., the arc and weld joint, are not obstructed by the visual cues 700. To know where objects such as the welding coupon 480A, workpiece 480B and/or weld joint are located, the system 400 can use point markers as discussed above (or some other type of tracking system). The spatial tracker 420 and/or the logic processor-based subsystem 410 can then automatically identify the objects in the welding environment 480 based on analyzing the digital image from the tracking cameras. Preferably, the visual cues 700 automatically move locations on the display 441 if the programmable processor-based subsystem 410 determines that movement of the welding torch or some other obstruction will interfere with the user's ability to view the welding operation and/or visual cue.

The tracked parameters such as the position, orientation and movement of welding tool 460 and welding process parameters such as welding voltage, welding current, wire feed speed, etc. can be compared to upper and lower target thresholds, target values or preferred variations for the type of welding process (e.g., GMAW, FCAW, SMAW, GTAW), the type and orientation of the weld joint, the type materials, etc. The upper and lower thresholds or preferred variations can be based on the motions of an expert welder, based computer modeling, testing of similar prior welds, etc. For example, when a welder performs a weld (e.g., expert welder, instructor, a trainee, etc.), the position, orientation and movement of welding tool 460 of the welder and welding process parameters such as welding voltage, welding current, wire feed speed, etc. are recorded. After completing the weld, the welder can select an appropriate menu item that "clones" the procedure. The "cloned" procedure is then stored and can serve as a reference for future welding procedures. Preferably, the upper and lower target thresholds, target values or preferred variations can be entered manually by the welder and, more preferably, are automatically entered using default values, e.g., ±5% or some other appropriate value. Preferably, the upper and lower target thresholds, target values or preferred variations are configurable by the user.

Preferably, when the position, orientation or movement of the welding tool 460 and/or the welding process parameters fall outside the upper and lower target thresholds, target values or preferred variations, the programmable processor-based subsystem 410 changes an attribute, e.g., color, shape, size, intensity or brightness, position and/or some other characteristic, of the appropriate visual cue. For example, the programmable processor-based subsystem 410 can change the color of the visual cue from green to yellow to red depending on the amount of deviation, and/or the visual cues can graphically show the amount of deviation from the target. For example, as seen section A of FIG. 18, the travel speed 708 shows the target value T and the amount of deviation from the target value 730 using a pointer 732 against a meter-type graphic. As seen in section A, the current travel speed is slightly fast. For CTWD 704, the indicator 734 moves relative to target 736 as shown by arrow 738. For work angle 706, the cross-hairs 740 move relative to target circle 742. Of course, the type of graphic and method of showing deviation is not limited to just these preferred embodiments. Preferably, one or more of the visual cues 700 can be programmed to change one or more attributes such as, e.g., color, shape, size, intensity or brightness, position and/or some other characteristic of the visual cue 700 when the tracking parameter and/or welding process parameter associated with the visual cue deviates from a target, e.g. falls outside of upper and lower target thresholds, target values or preferred variations for the type of welding process. Preferably, the amount of deviation is taken into account when determining a change in one or more attributes of the visual cue. For example, a visual cue 700 can have a green color if the visual cue 700 is within upper and lower target thresholds, at the target value (within an acceptable tolerance) or within preferred variations for the type of welding process. The visual cue 700 can be programmed to change its color (e.g., to yellow), shape, size, intensity or brightness, position and/or some other characteristic to provide a warning to the user if the associated parameter falls outside the upper and lower target thresholds, target value (e.g., outside an acceptable tolerance) or outside of preferred variations for the type of welding process by a first predetermined amount or warning level, e.g., a deviation that will produce an acceptable weld but not the best weld. Preferably, the system 400 provides one or more warning levels or one or more of the visual cues 700. In addition to providing one or more warning levels, the visual cue 700 can also be programmed to further change its color (e.g., to red), shape, size, brightness, position or some other characteristic to provide an alarm to the user if the associated parameter falls outside the upper and lower target thresholds, target value (e.g., outside an acceptable tolerance) or outside of preferred variations for the type of welding process by a second predetermined amount or alarm level, which is greater than the first predetermined amount. For example, the second predetermined amount or alarm level can be a deviation that will likely produce an unacceptable weld. Preferably, the system 400 provides one or more alarm levels for one or more of the visual cues 700. Preferably, any combination of the attributes of the visual cue 700 can be changed. For example, any combination of the color, the size, brightness and/or any other attribute of the visual cue 700 can be changed. Of course, any number and combination of warning and alarm levels can be programmed into the logic processor-based subsystem 410.

Visual cues 700 are not limited to just providing warnings and alarms. In exemplary embodiments of the invention, visual cues 700 can aid in identifying to the user the weld start position, the weld stop position and the total length of the weld. For example, in cases were the entire joint between two workpieces is not welded but only certain portions, the visual cues 700 can aid the user in identifying the start position by having a marker such as, e.g., a green spot at the start position and a second marker such as, e.g., a red spot at the stop position. In some embodiments, the visual cues aid in achieving the proper weld length. For example, an indication, e.g. a green spot, is turned on at the start position (or any other desired location on display 441) to start the weld and the user welds until the indication is turned off or changes color to achieve the desired weld length. Preferably, the visual cues 700 aid in the welding sequence to be followed. For example, if the welding should be done from the center of the workpiece and outward to the ends in order to reduce stresses in the workpiece, the visual cues 700 can alert the user, e.g., by displaying a message in text, e.g., in a corner of the display 441, or by using visual cues 700 to identify the start position, stop position and weld length as discussed above. In some embodiments, the visual cues 700 provide an indication of the welding progression. For example, a visual cue can provide the percent completion of a weld joint in, e.g., a corner of the display 441 or some other desired location, and/or provide an indication of the pass number in a multi-pass weld. Preferably, the visual cues 700 also aid the user in performing the weld. For example, in a weld procedure requiring a weave pattern, a visual cue can provide an indication, e.g. a bright spot that cycles in the preferred weave pattern at the end of the welding tool tip for the user to copy while welding. Similarly, when performing a TIG welding operation, the visual cues can indicate the proper frequency at which the filler wire should be added to the weld puddle. For example, a pulsating marker, e.g., a green spot that changes brightness, can be displayed at the end of the welding tool tip and the user knows to add the filler wire at the frequency of the pulsations, e.g., dip the filler wire in the weld puddle whenever the marker is ON or brighter (or when the marker is OFF or dimmer).

Audio cues can also be used to aid the user. For example, similar to visual cues, audio warning and alarms can be sent to speakers in the welding helmet 440 to alert the user if the position, orientation or movement of the welding tool 460 and/or the welding process parameters fall outside the upper and lower target thresholds, target value (e.g., outside an acceptable tolerance) or outside of preferred variations for the type of welding process. The warnings can be in any audio format, e.g., tones of different frequencies, buzzers, and voice alerts. Different frequencies and/or pitches can indicate to the user which parameter is not on target and the amount of deviation. Preferably, the logic processor-based subsystem 410 provides voice alerts to inform the user of problems. For example, the voice alert can instruct the user that the travel speed is too fast or too slow. Voice alerts can provide instructions or suggestions to the user in making any necessary corrections. Similar to the visual cues discussed above, voice alerts can also aid the user in making the weld, e.g., weave pattern, TIG welding, start and stop indicators, weld length, sequencing, and/or welding progression. Audio cues can be provided in place of the visual cues discussed above. Preferably, a combination of audio cues and visual cues are provided by logic processor-based subsystem 410.

Preferably, the visual and audio cues can be selectively turned ON or OFF by the user. In addition, with respect to the visual cues, the user can select whether to fixedly locate the visual cues 700 in a desired location on display 441 such as, e.g., a corner or along one of the sides of display 441, or "attach" the visual cues 700 to an object on the display 441 such as, e.g., welding tool 460. In some embodiments, the user 441 can individually select the visual cue 700 or audio cue to turn ON or OFF. Preferably, the visual cues 700 and/or the audio cues are grouped so that the user can select a group of cues to turn ON or OFF. For example, cues related to information from the welding power supply 450 can be grouped together and information related to welding tool 460 can be grouped together. The grouping can be preprogrammed or custom programmed, e.g., by the user. In some embodiments, the user can use the display 441 and user controls on, e.g., welding tool 460 or a remote control device, to activate or deactivate the visual and audio cues. Preferably, the user can use welding user interface 430 for activating and deactivating the cues. In some embodiments, the user can activate and deactivate the cues using voice commands. For example, the user can say "GROUP 1 ON" to activate the visual cues and/or audio cues related to the welding tool 460. To "attach" the GROUP 1 visual cues to the welding tool 460, the user can say "GROUP 1 ATTACH". In some embodiments, eye tracking, as discussed above, can be used to highlight and select an appropriate menu item(s) to activate and deactivate the cues.

In preferred exemplary embodiments, welding data related to the position, orientation and movement of welding tool 460 and/or welding process parameters is stored as the user performs the weld. The stored data can be retrieved for subsequent review for training or certification purposes. For example, the programmable processor-based subsystem 410 can store the welding data (e.g., as a *.dat file), for reviewing the progress and/or performance of the welder at a later time. In some embodiments, the stored weld data can be used as the target values for the visual and audio cues. The stored target weld data can be that of a successful weld by an expert welder or even a successful prior welding run by the user. In some embodiments, the stored target weld data is based on computer modeling for the specific type of weld and/or testing of similar prior welds. Preferably, the stored target weld data includes information related to the weld weave pattern, TIG welding information such as filler frequency, welding start and stop indicators, weld length, welding sequencing, and welding progression. When a welding operation is started, visual and audio cues based on the stored target weld data will aid the user in creating the new weld. By using the target weld data, even experienced welders can benefit as the visual and audio cues can provide guidance in performing an unfamiliar weld sequence, an unusual weld joint configuration, etc.

Preferably, welding system training software to train welders, whether beginners or experienced, can be loaded into and executed by the logic processor-based subsystem 410. The user selects the appropriate welding training procedure and starts to perform the welding. The training software monitors and records the performance of the user as the user performs a weld. Generally, in related art real-weld training systems, welding equipment such as the power supply, wire feeder, hot-wire power supply, etc. do not communicate with the welding training computer. This means that, before or after the user selects a welding training procedure to run, the user must set up the power supply and possibly other welding equipment such as the wire feeder and/or a hot-wire power supply based on the selected welding training session. Typically, the welding equipment, e.g., the power supply, is located remotely from the welding training area. This means that any changes to the settings or verification of the settings on the welding equipment, e.g., the power supply, will require the user to exit the training area, and the trips to the welding equipment can occur multiple times during a welding training session, which can become cumbersome.

Because the tracking and monitoring of the welding tool 460 and/or the welding helmet 440 as the user performs the welding are discussed above with respect to system 400, for brevity, the tracking and monitoring will not be repeated. In addition, the following exemplary embodiments will be described in terms of the welding training system communicating with a power supply. However, those skilled in the art will understand that the welding training system can also communicate with other welding equipment such as wire feeders, hot-wire power supplies, etc.

Figure 19:
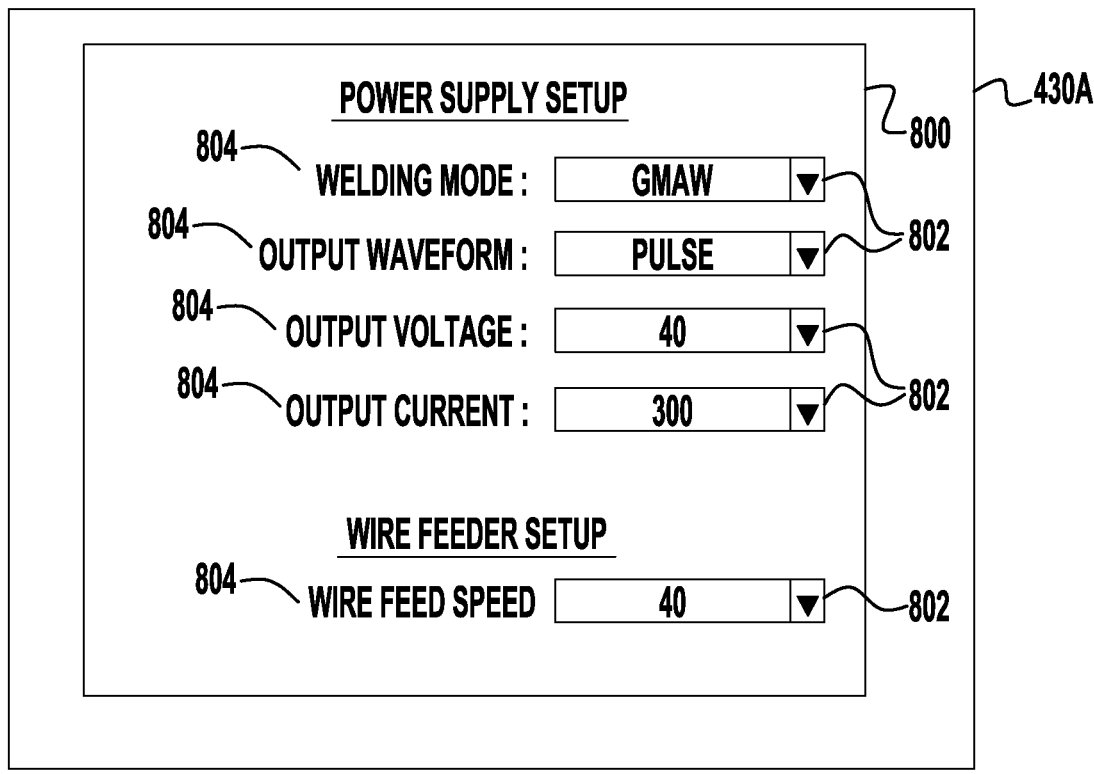
FIG. 19 illustrates an exemplary user input screen for setting parameters on welding equipment.

In exemplary embodiments, user can communicate with welding equipment such as the power supply 450 using either the face-mounted display device 440A or the observer/set-up display device 430A connected to the welding user interface 430. Preferably, along with monitoring outputs of the power supply 450 such as voltage and current as discussed above, the user can also setup, view and change settings on the power supply 450. Preferably, the user uses display 430A and input device 430B (e.g., keyboard, mouse, or any other known inputting device) of the welding user interface 430 to communicate with the power supply 450 via the logic processor-based subsystem 410. Preferably, after providing login information on a login screen, the user can select a setup screen for setting parameters of the welding equipment. FIG. 19 illustrates an exemplary embodiment of a setup screen 800 for setting, viewing and/or changing power supply settings. The screen 800 includes power supply settings that can be changed manually via input fields. As seen in FIG. 19, the user can set the welding mode of the power supply 450. For example, depending on the type of power supply, the user can select, e.g., by using a dropdown box 802 or some other input means, a mode of operation for the power supply 450 such as, e.g., GMAW, FCAW, SMAW, GTAW. Depending on the selection, one or more additional parameters 804 can be made available to the user for review and to change, if needed. For example, as seen in FIG. 19, settings such as waveform type (short-arc welding, pulse welding, etc.), output voltage and output current have been shown for viewing and/or modification. Of course other parameters such as polarity (positive or negative), inert gas flow setting, etc. can also be made available to the user. Similar to the welding mode setting, the selection of values for each of the parameters 804 can be made via dropdown boxes 802 or some other input means. Preferably, the parameter settings can have an initial default value in order to minimize the setup time for the user. In some embodiments, the power supply 450 and/or the logic processor-based subsystem 410 can also communicate with a wire feeder, hot-wire power supply, or some other welding equipment. The settings for the other equipment can also be made via screen 800 and/or other setting screens. For example, as seen in FIG. 19, the wire feed speed can also be input using dropdown boxes 802 or another input means.

In some exemplary embodiments, the face-mounted display 440A can be used to view, setup and change the settings on the welding equipment such as the power supply 450, wire feeder, hot-wire power supply, etc. The user can be shown the display prior to welding operation and the user can navigate through the selection screen using. e.g., voice commands, eye tracking and/or other input devices. In some embodiments, a manual remote control device can be used. The manual remote control device can be especially useful when used with a welding helmet 440 where the user can see through the display 440A. In either type of face-mounted display 440A, the user can navigate through the setting screen(s) and verify the settings prior to starting the weld training session. If the settings need to be modified for any reason, the user can immediately change the settings rather than having to stop and walk over to the welding equipment to change the settings.

The welding equipment, e.g., power supply 450, and/or the logic processor-based subsystem can include the software that transmits the screen 800 to the display 440A and/or 430A. For example, the programmable processor-based subsystem 410 can include software that receives the requests for information from the user and retrieves the information from the welding equipment. Preferably, the screen 800 is a web page transmitted by a webserver hosted on the programmable processor-based subsystem 410 and/or power supply 450 or some other welding equipment. In some embodiments, and app-based system can be used. Such client-server type software is known to those skilled in the art and thus will not be further discussed except as needed to describe exemplary embodiments of the invention.

Figure 20:
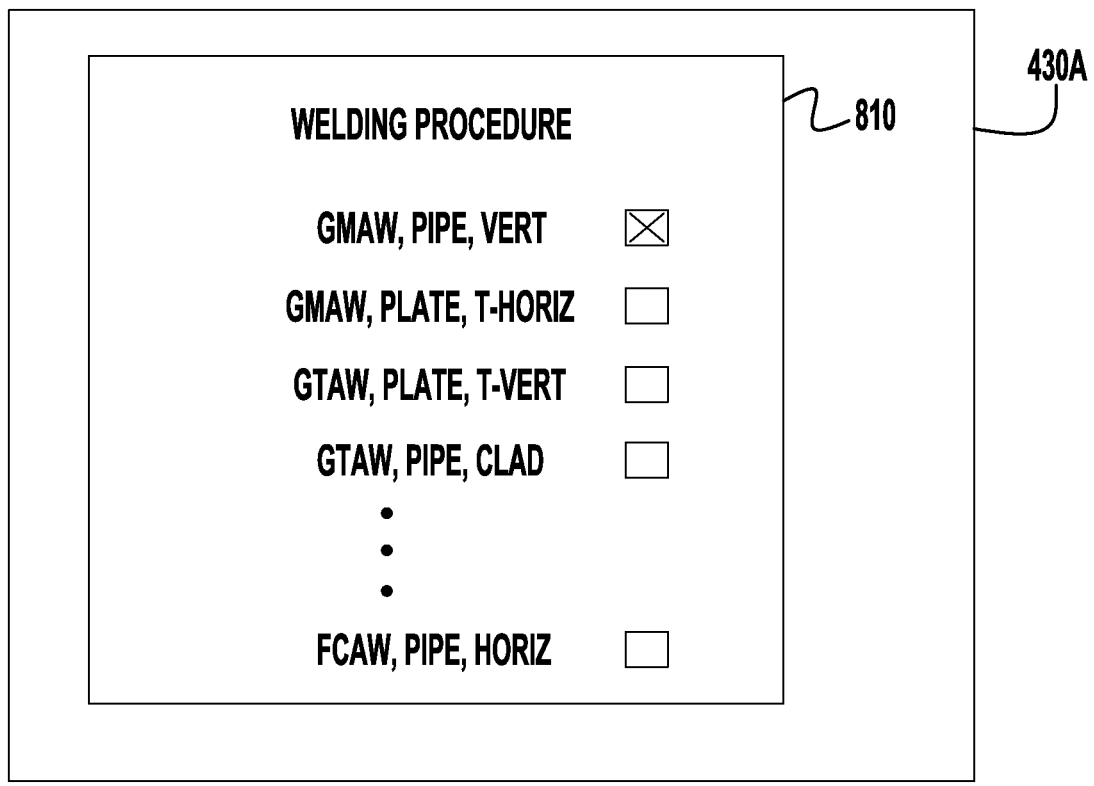
FIG. 20 illustrates an exemplary user input screen for selecting a welding procedure.

Preferably, the power supply 450 and/or other welding equipment are automatically set up based on the welding training session selected by the user. For example, as seen in FIG. 20, on screen 810, the user can select a welding procedure to perform during a welding training session. Preferably, the welding procedure determines the type of welding mode (e.g., GMAW, FCAW, SMAW, GTAW), the type of welding coupon (e.g., pipe, plate, etc.), the orientation of the weld joint (vertical, horizontal), etc. Preferably, based on the selection, default settings for the appropriate welding equipment such as welding power supply 450, wire feeder, hot-wire power supply, etc. are determined and automatically populated and presented to the user for review on screen 800 (see FIG. 19). Preferably, the user can modify the settings, if desired, as discussed above. Preferably, safeguards are set up so that the user can only change the settings in a range that is safe and/or practical for the selected welding procedure and/or welding equipment, e.g., safeguards are set in place so that a user cannot change the settings so as to create a dangerous condition either to the user or the welding equipment. Preferably, the safeguards are based on the level of skill of the user and/or the type of welding procedure selected. Once the selection made, the programmable processor-based subsystem 410 can transmit to the settings for the selected welding procedure to the power supply 450 and/or other equipment such as a wire feeder, hot-wire power supply, etc. By providing default values for the selected welding procedure and automatically updating the settings on the power supply 450 and/or the other equipment, there is less chance for the user to improperly set the power supply 450 and/or the other equipment prior to the start of the welding session. Of course, the user can still have the option to view and change the default settings, e.g., by using screen 800, as discussed above.

Preferably, the programmable processor-based subsystem 410 and the power supply 450 (and/or some other welding equipment) communicate via the network 475 (see FIG. 14). Although illustrated as a wireless network, the network can be wired or a combination of both. Preferably, the network is Ethernet, but other types of networks such as Arclink, CAN, etc. can be used. In addition to communicating with the power supply 450, the programmable processor-based subsystem 410 can communicate with one or more other programmable processor-based subsystems and their respective power supplies via an intranet, WAN, LAN, Internet, etc. Preferably, monitoring equipment is connected to the network 475, e.g., via a WAN, Internet, etc. so that instructors, other trainees or any other interested party can monitor the trainees/welders on the programmable processor-based subsystem 410 from another location, e.g., remote monitoring from an off-site location. Preferably, a web-based and/or an app-based interface can be used to monitor the progress of one or more trainees/welders by uploading information from the respective programmable processor-based subsystem. For example, an observer can display the progress of one or more trainees/welders on a remote console that is connected to the network 475 via an intranet or the Internet. The display can use any appropriate format such as graphs, graphics, text, numeric values, etc. to show the progress of the trainees/welders.

Figure 21:
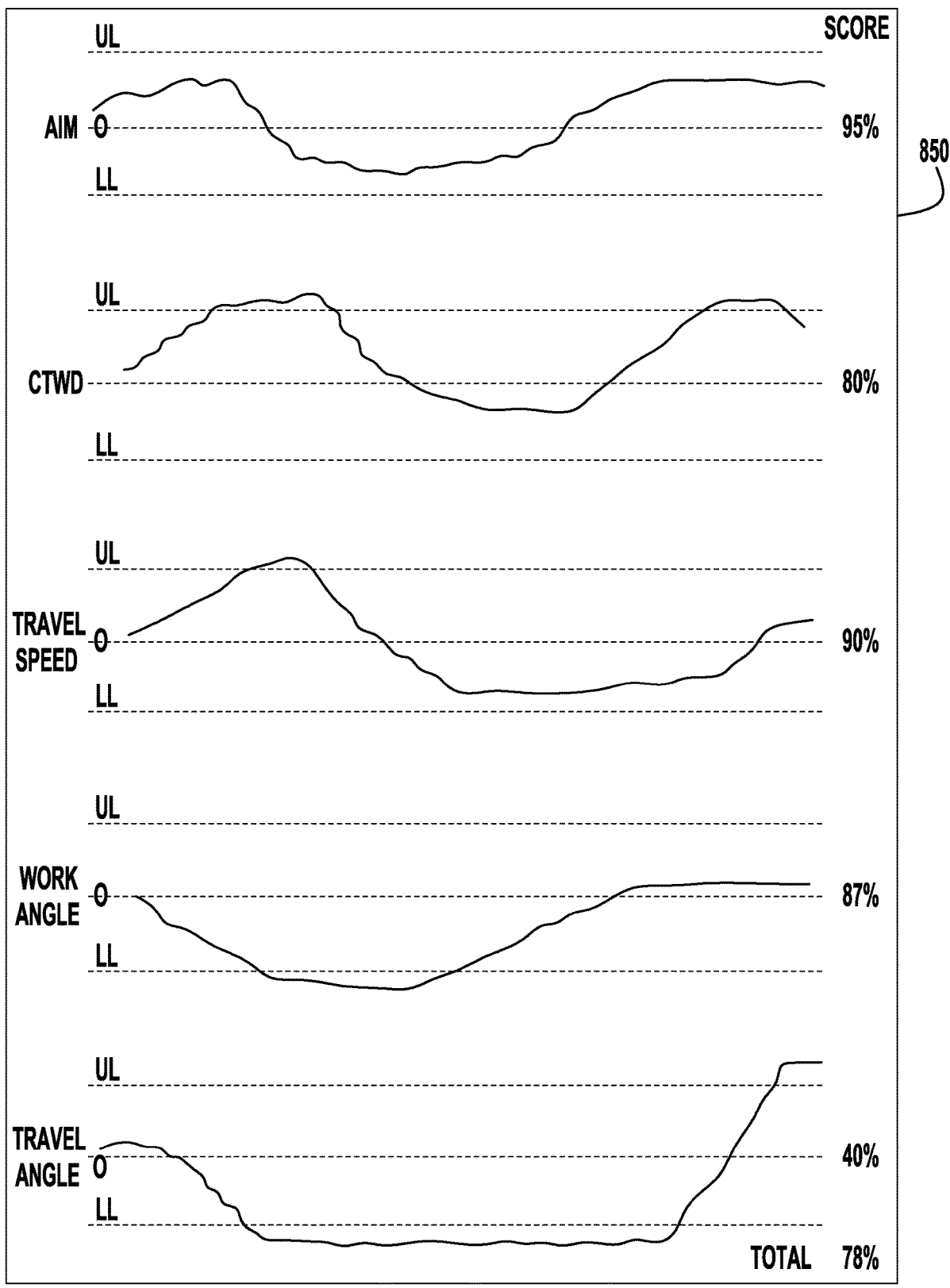
FIG. 21 illustrates an exemplary graph with various plots of welding tool parameters.

In preferred embodiments of the invention, when the user presses the trigger of the welding tool 460, the power supply 450 sends a signal to the processor-based subsystem 410 indicating that the welding process (whether real or simulated) has started. Of course, when the weld is simulated, the power supply 450 does not provide a real-world voltage or current output and any voltage, current and power readings are simulated along with a simulated weld bead. The trigger signal can be used by the processor-based subsystem 410 to start recording the performance of user. For example, once the trigger signal is received by the processor-based subsystem 410 indicating the welding has started, the processor-based subsystem 410 can start recording performance parameters of the user such as CTWD, travel speed, work angle, travel angle and aim. In addition, the logic processor-based subsystems 410 can include parameters from the welding equipment such as welding voltage, welding current, wire feed speed, hot-wire current, etc. Preferably, as seen in FIG. 21, one or more of the performance parameters, e.g., CTWD, travel speed, work angle, travel angle and aim, and one or more of the welding voltage, welding current, wire feed speed, etc. can be plotted on a graph 850 that is shown on, e.g., display 430A so that can an observer, such as an instructor, can view the welding session of the user. Preferably, each of the plotted parameters has an upper and lower threshold values and/or an optimum value, which are displayed on the graph 850 along with the actual values. Preferably, a score based on the performance or welding equipment parameter staying with the upper and lower threshold values and/or on the deviation of the performance or welding equipment parameter from the optimum value is provided on the display 430A for one or more of the plotted parameters. Preferably, one or more of the individual scores are used to generate a total score indicative of the performance of the welder and/or the quality of the weld. Preferably, the processor-based subsystem 410 provides an analysis of potential flaws (e.g., porosity, incomplete fusion (not enough penetration), crack in the weld, undercut, weld profile is too thin, weld profile is too thick, etc.) in the weld. Preferably, the graph 850 is displayed on display 430A or a remote computer in real-time. As indicated above the data for the welding session can be stored and analyzed at a later time. Thus, the graph 850 and/or any other information can be displayed or printed for analysis at a later time.

In some embodiments, the welding equipment itself may provide a score for the welding session when performing a weld. For example, Lincoln Electric PowerWave™ welding power supplies provide a weld score based on the current value, voltage value and the stability of the current and voltage values throughout the welding session. Preferably, the weld score is incorporated into the total score. Preferably, a real-time indication of the weld score is provided to the user via the face-mounted display 440A, e.g., as a visual cue as discussed above. For simulated welding, the user can practice setting up the welding power supply 450 and the processor-based subsystem 410 can communicate with the welding power supply 450 to determine if the user properly set up the machine. Preferably, if the welding power supply 450 is set up incorrectly the processor-based subsystem 410 can be configured such that the user will be unable to proceed and/or the score will be negatively impacted.

Preferably, one or more of the plotted parameters or the scores are provided to the user in real-time via the face-mounted display 440A as the user is welding, e.g., as a plotted graph or as a visual cue as discussed above. In some embodiments, the attributes of these parameters can be changed as discussed above whenever the parameter goes into a warning state or an alarm state based on the upper and lower threshold values and/or deviation from the optimum value.

In another exemplary embodiment, along with the visual and audio cues discussed above, the system 400 can overlay virtual objects on or over the real-world objects in the welding environment in real-time to provide a mixed reality and simulated scene of the welding environment. Preferably, the virtual objects are generated by the logic process-based subsystem 410. The virtual objects can include any object that can aid or train the user when performing a weld (e.g., real-world, simulated or a combination thereof) whether in a training environment or out in the field, e.g., a manufacturing site or a construction site. Preferably, the logic process-based subsystem 410 generates virtual objects to be overlaid on the welding environment 480 in real-time such that the user can see the virtual objects on display 441 during the welding process. In some embodiments, the generated virtual objects can also be transmitted to display 430A to been seen by other observers such as a welding instructor.

Figure 22:
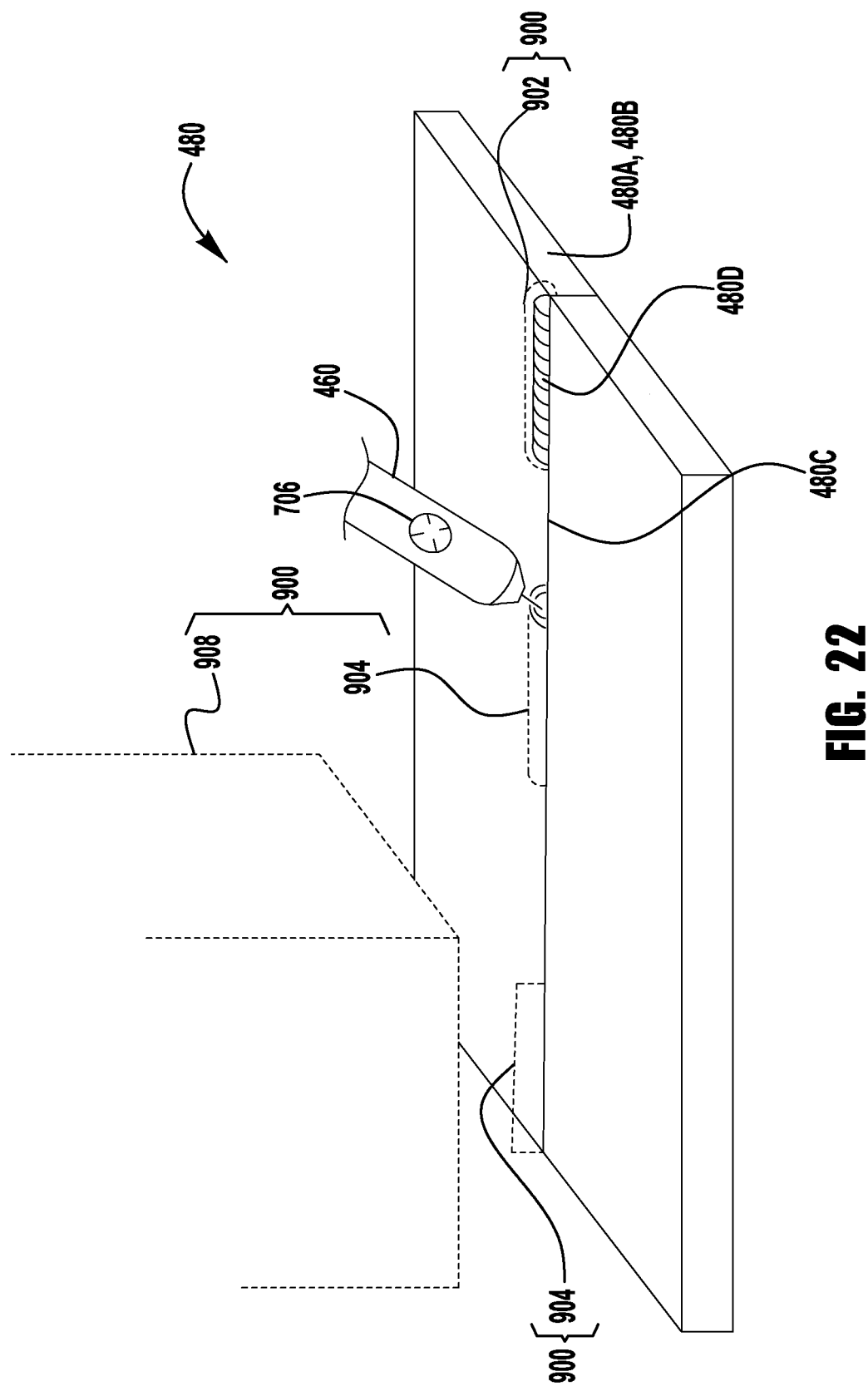
FIG. 22 illustrates a perspective view of a welding environment showing real-world objects, visual cues and virtual objects.

FIG. 22 illustrates and exemplary view of welding environment 480 as seen by the user via, e.g., display 441 of the face-mounted display device 440A and/or as seen by another observer on the display 430A during welding operations by the user. The view of the welding environment 480 includes real-world objects such as, e.g. welding tool 460 (including any arc), welding coupon 480A or workpiece 480B (including any weld puddle), weld 480D and weld joint 480C. Of course one or all of the welding tool 460 (including the arc), welding coupon 480A or workpiece 480B (including the weld puddle), weld 480D and weld joint 480C can be simulated or a mix of real-world and simulated depending on the type of session. For example, for a simulated welding session, the weld 480D and weld joint 480C can be simulated. In some sessions, one or more of the welding tool 460, welding coupon 480A or workpiece 480B, weld 480D and/or weld joint 480C can be a real-world object that is overlaid with a simulated texture, shape, etc. to resemble a real-world item. For example, the welding coupon 480A or workpiece 480B can be a simple real-world object that is overlaid with a virtual object to simulate a complex part (e.g., an automotive axle or some other real-world part, device or component). However, for brevity and clarity in describing the present exemplary embodiment, the welding tool 460, welding coupon 480A or workpiece 480B, weld 480D and weld joint 480C are depicted as real-world objects in FIGS. 22 and 23. Preferably, the view on display 441 also includes virtual cues 700 as discussed above. For example, work angle 706 is illustrated in FIG. 22. However, other visual cues 700 can also be included in the display 441 as discussed above. In addition to real-world objects and visual cues 700, preferred embodiments can also generate and overlay virtual objects onto the real-world image signal (e.g., video) captured by image capture device 470 or, in the case of a HUD with a see-through lens (e.g., an auto-darkening lens), onto the image signal sent to the combiner of a HUD, as discussed above.

For example, as seen in FIG. 22, virtual objects 900 are overlaid onto the real-world welding environment 480 seen by user. The virtual objects 900 can include any object that provides information to the user to aid in performing the welding operation and/or provide information on performance of the user and/or quality of the weld. Preferably, virtual objects 900 can have attributes similar to those discussed above with respect to visual cues 700. For example, virtual objects 900 can have attributes such as, e.g., color, shape, size, intensity or brightness, position and/or some other characteristic, which can be displayed and/or changed to aid the user during welding and/or provide information about the weld and/or user performance. However, while virtual objects 900 can perform a similar function as visual cues 700, the virtual objects are virtual representations of objects, e.g., objects that can be found in a typical real-world weld environment (welds, walls, pipes, overhanging obstructions or any other object that can be virtually generated to aid the user in weld training).

Figure 23:
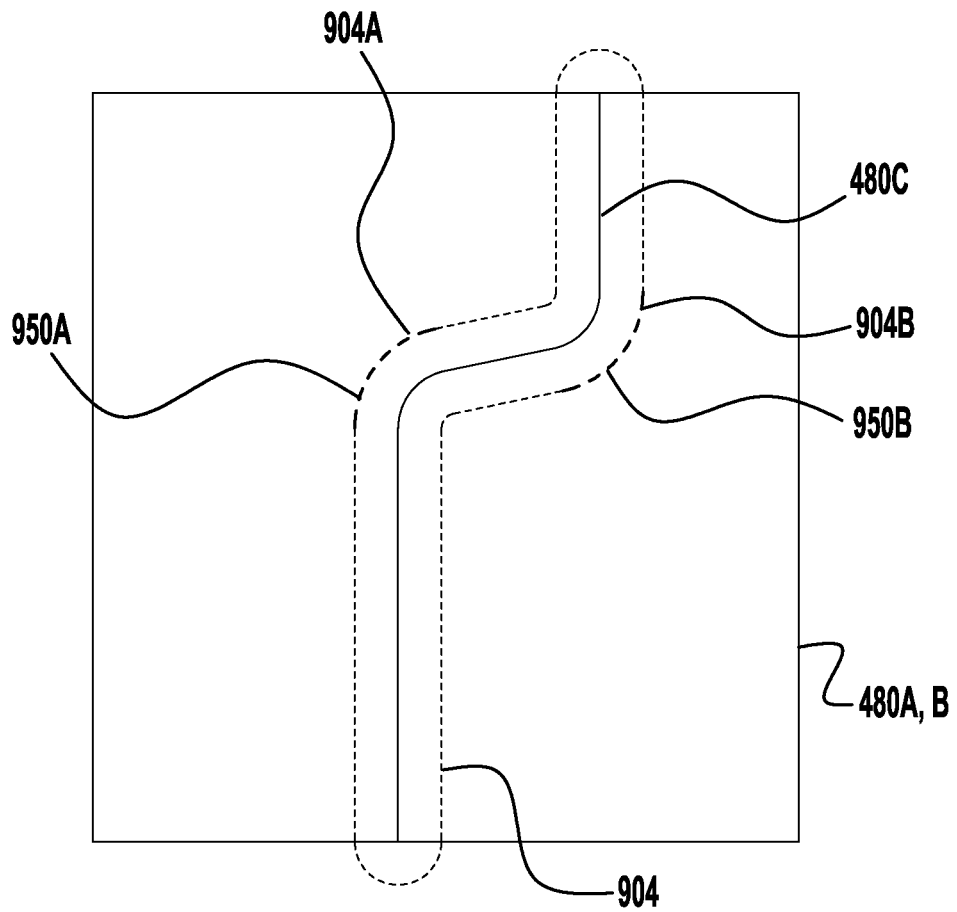
FIG. 23 illustrates a top view of a welding environment showing real-world objects and virtual objects.

For example, the logic processor-based subsystem 410 can generate virtual weld objects 904 that visually show where the user should place the welds on a coupon/workpiece 480 A, B. Similar to the weld start/stop visual aids discussed above, the weld objects 904 show where the user should place the weld and how long the weld should be. For example, as seen in FIG. 22, a virtual weld object 904 is shown at the spot where the user is welding to aid the user in showing how long the current weld should be and where to stop welding. In addition, a virtual weld object 904 at the left end of coupon/workpiece 408 A, B visually indicates to the user where the next weld should be placed after the current weld is done. Preferably, the virtual weld object 904 is partially transparent so that the user's view of the weld joint 480C is not obstructed. In addition, certain attributes of the virtual weld object 904 can be changed or displayed differently from the rest of the virtual weld object 904 to provide information that can aid the user. For example, as seen in FIG. 23, real-world objects such as the coupon/workpiece 480A, B and the weld joint 480C are visible to the user on display 441. In FIG. 23, the weld joint 480C is not a straight path and some sections of the weld joint 480C include curves. To aid the user in navigating the curved weld path, in exemplary embodiments, a virtual weld object 904 can be overlaid onto the weld joint 480C. For example, FIG. 23 shows virtual weld object 904 with curves 904A and 904B overlaid onto the weld joint 480C. While just displaying the virtual weld object 904 provides indication to the user that the weld path is curved prior to welding, the focus of the user during the actually welding process will be at the torch tip and the user may not immediately realize the weld path goes in different direction as the user hits the curves 904A, B. To further aid the user, the attributes of the virtual weld object 904 and/or a part of the virtual object 904 can change as the user approaches the curves 904A, 904B. For example, the color, shape, size and/or intensity (or brightness) of the curves 904A, B of the virtual weld object 904 can change to aid the user. In the embodiment of FIG. 23, the attributes 950A and 950B along the curves 904A, B, respectively, of the virtual weld object 904 can be displayed differently from the rest of the virtual weld object 904 and/or can change when the welding tool 460 is at (or immediately prior to) the curve 904A and/or 904B in order to inform the user that there is a change in direction of the weld path. For example, the attributes 950A and 950B can be set to a different color than the rest of the virtual weld 904. In addition, different colors can be assigned to the attributes 950A and 950B to indicate the direction of the change in the weld path of joint 480C. For example, 950A can be red to indicate a change to the right and 950B can be blue to indicate a change to the left. Of course, the use of the color attribute is exemplary and other attributes can be displayed or changed as desired. For example, 950A, B can have a different intensity than the rest of the virtual weld object 904. In addition, although virtual welding objects 900 (e.g., virtual weld object 904) can be used by themselves, the logic processor-based subsystem 410 can also generate one or more visual cues 700 and audio cues, as discussed above, to aid the user in perform the weld. For example, visual cues related to the weld tool position, orientation and motion, e.g., CTWD, travel speed, work angle, travel angle and aim, can be, e.g., displayed on a fixed location on the display 441 and/or "attached" to the welding tool 480 to help the user in navigating the weld path. Preferably, the characteristics of the virtual weld object, e.g., height, width, length, shape, profile, weld path, etc. is based on the type of weld joint (e.g., straight, orbital, curved, fillet, lap, groove, etc.), orientation of the weld joint (horizontal, vertical, out-of-position, etc.), the type of welding operation (e.g., GMAW, FCAW, SMAW, GTAW), etc. Preferably, a variety of virtual weld objects are pre-loaded and/or can be custom built and stored in the system 400, e.g., in logic processor-based subsystems 410.

Preferred embodiments can also generate and display other virtual objects that can aid or train the user. For example, as seen in FIG. 22, virtual object 908 represents an obstruction that welder may encounter in a real-world welding scenario. The virtual obstruction object 908 can be generated and displayed on the display 441 next to the weld joint 480C to simulate an object that will prevent the user from either properly seeing the weld joint 480C and/or properly positioning the welding tool 460 as desired in a real-word scenario. Preferably, attributes of the virtual obstruction object 908 change whenever the user "hits" the simulated object during the welding. For example, the virtual object 908 can change colors whenever it "hit." Preferably, the virtual obstruction object 908 is opaque. In some embodiments, visual and audio cues can be used to aid the user in navigating the obstruction. For example, visual cues related to the weld tool position, orientation and motion, e.g., CTWD, travel speed, work angle, travel angle and aim, can be, e.g., displayed on a fixed location on the display 441 and/or "attached" to the welding tool 480, as discussed above, to help the user in navigating the obstruction and/or indicate when the obstruction has been "hit." In addition, audio and/or tactile feedback can be provided to help the user in navigating the obstruction and/or indicate when the obstruction has been "hit," e.g., an audible buzzer and/or the welding tool 460 can vibrate. The simulated obstructions can simulate walls, ceilings, pipes, fixtures, and/or any other type of obstructions. Preferably, the logic processor-based subsystem 410 and/or another computer includes a database of predefined obstruction categories such as e.g., an overhanging obstruction over the weld joint, an obstruction between the user and the weld joint, and obstruction that is very close to the weld joint, and/or another type of obstruction, which can be uploaded, by e.g., the user and/or the instructor, into welding training sessions. In some embodiments, real-world welding scenarios where obstructions are common such as welding girders or beams on bridges, in buildings, etc. are pre-loaded and/or can be custom built and stored in the system 400, e.g., in logic processor-based subsystem 410, for the user to select and practice on.

In addition to aiding the user in real-time during the welding process, virtual objects 900 can also provide information on the performance of the user and/or the quality of the weld. For example, the weld tool position, orientation and motion, e.g., CTWD, travel speed, work angle, travel angle and aim, can be used to determine if there is a potential flaw (e.g., porosity, incomplete fusion (not enough penetration), crack in the weld, undercut, weld profile is too thin, weld profile is too thick, etc.) or other problem in the weld. Preferably the position, orientation and motion, e.g., CTWD, travel speed, work angle, travel angle and/or aim, of the welding tool 460 is compared to upper and lower target thresholds, target values or preferred variations for the type of welding process (e.g., GMAW, FCAW, SMAW, GTAW), the type and orientation of the weld joint, the type materials, etc., to determine whether a potential flaw or other problem in the weld exists. In addition to the user's performance with respect to the position, orientation and motion of welding tool 460, other system parameters such as voltage, current, wire feed speed, arc length, heat input, gas flow (metered) and/or deposition rate (e.g., lbs./hr., in./run) can be analyzed to determine whether the weld 480D is acceptable. For example, based on one or more of the user's performance parameters and/or one or more of the other system parameters, the system 400, e.g. logic processor-based subsystem 410, can include algorithms that determine areas in the weld 480D that can have potential flaws or other problems such as, e.g., porosity, incomplete fusion (not enough penetration), crack in the weld, undercut, weld profile is too thin, weld profile is too thick, etc. Algorithms to determine potential problems such as, e.g., porosity, incomplete fusion, crack in the weld, undercut and/or weld profile are known in the art and thus will not be discussed further except as needed to describe the preferred embodiments. The algorithms compare one or more of the user's performance parameters thresholds and/or the other system parameters to set point values, e.g., upper and lower threshold values, optimum values and/or preferred variation, to see if the set point values are exceeded by a predetermined amount at any point on the weld 480D. If so, the system 400, e.g., logic processor-based subsystem 410, keeps track of the point in the weld that the set point values were exceeded. Based on the whether the set point values were exceeded, the attribute, e.g., color, intensity, etc., at the appropriate point on the virtual weld object 902 can be changed to indicate the potential flaw or problem in the weld.

Figure 24:
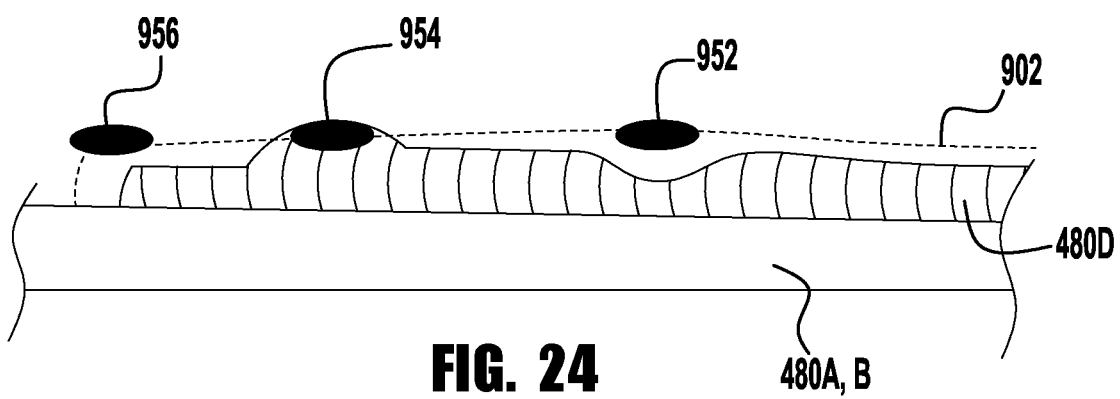
FIG. 24 illustrates a side view of a welding environment showing real-world objects and virtual objects.

For example, as seen in FIGS. 22 and 24, a virtual weld object 902 can be overlaid on completed weld 480D to indicate the quality of the weld. Preferably, as seen in FIG. 24, the overlaid virtual weld object 902 is a representation of an ideal weld profile. Preferably, the virtual weld object 903 is partially transparent so that the user can readily see the underlying weld 480D. By overlaying the virtual weld object 902 on top of the completed weld 408D, the user and/or another observer can visually see a comparison of the actual weld produced by the user with an ideal weld. As used herein, the terms "ideal weld" and "ideal weld object" do not necessarily represent perfect weld profiles but rather weld profiles that can be used for comparison purposes. Preferably, in addition to providing a visual comparison, attributes of the virtual weld object 902 can be displayed and/or changed to show areas of the weld that may be problematic. For example, as seen in FIG. 24, based on a comparison of the user's performance parameters and/or the other system parameters to predetermined set point values, the attributes (e.g., the color, shape, size, intensity (or brightness) and/or another attribute) along one or more portions of the virtual weld object 902 can be displayed or changed over the potential problem areas. As seen in FIG. 24, the attribute 952 can be, e.g., red (or another color) to indicate that the weld profile is too thin in that area or there is a potential crack, etc. Similarity, the attribute 954 can be, e.g., red (or another color) to indicate that too much weld filler has been laid down at the a spot, and attribute 956 can indicate that the user has stopped short of completing the full weld length. Of course, the visual indications of problem areas can be overlaid directly on the weld 480D on display 441 without overlying an ideal virtual weld object 902 on the weld 480D. However, by overlaying the ideal virtual weld object 902 over the weld 480D, the user is able to see a complete profile of the actual weld as compared to an ideal weld and not just the potential problem areas.

Preferably, ideal weld objects are pre-loaded and/or can be custom built and stored in the system 400, e.g., in logic processor-based subsystems 410. The ideal weld objects can represent a variety of ideal weld profiles for the types of welding procedures, training procedures, that can be selected the system 400. Preferably, the ideal weld profile is based on the type of weld joint (e.g., straight, orbital, curved, etc.), orientation of the weld joint (horizontal, vertical, out-of-position, etc.), the type of welding operation (e.g., GMAW, FCAW, SMAW, GTAW), etc. The ideal weld object profiles (e.g., width and thickness of the weld seam) can be based on computer-generated models, based on data from analysis of test welds, based on a weld profile of an expert welder or another welder, and/or based on weld profiles know to be acceptable in the industry. In some embodiments, the virtual weld object can be based on a user's previous weld history in order to, e.g., compare the current weld with a previous weld. In some embodiments, a computer generated model of the actual weld profile is created during the welding process from one or more of the user's performance parameters, e.g., CTWD, travel speed, work angle, travel angle and/or aim, and/or one of more of the other system parameters, e.g., voltage, current, wire feed speed, arc length, heat input, gas flow (metered) and/or deposition rate (e.g., lbs./hr., in./run). The computer generated model of the actual weld profile can then be overlaid on weld 480D with the indications of any potential problem areas as discussed above. By seeing the computer-generated model, the user may see additional features of in generated weld that are difficult or impossible to see in the actual weld 480D, e.g., a potential flaw in the center of the weld. Preferably, in the above exemplary embodiments, the user has the option to turn ON and OFF the virtual objects 900, e.g., individually, all at one time and/or by groups (e.g., as discussed above with respect to visual cues).

In some exemplary embodiments, the coupon/workpiece 480A, B can be automatically calibrated by the system 400, e.g., by the logic processor-based subsystem 410. Typically, in order for a system such as system 400 to know where the actual weld path is (e.g. a fillet weld path, a lap weld path and a weld groove path), a person must first calibrate the system, especially the tracking subsystem such as spatial tracker 420, so that the system knows where the location of the weld path, the orientation of the weld path and the length of the weld path on the welding coupon or workpiece. The calibration typically involves placing the welding coupon or workpiece in a known calibration block that includes two or more markers (e.g. active or passive markers as discussed above) and allowing the system to capture the position of the markers, e.g., similar to the tracking discussed above with respect to spatial tracker 420 and processor-based subsystem 410. After the markers have been located, the system calculates the weld path location, orientation and length in the 3-D space of the welding environment. This allows the system to determine parameters such as aim, CTWD, etc. However, the system calibration requires human intervention and takes time to calibrate, which must be done every time a different type of coupon or workpiece is used.

Figure 25:
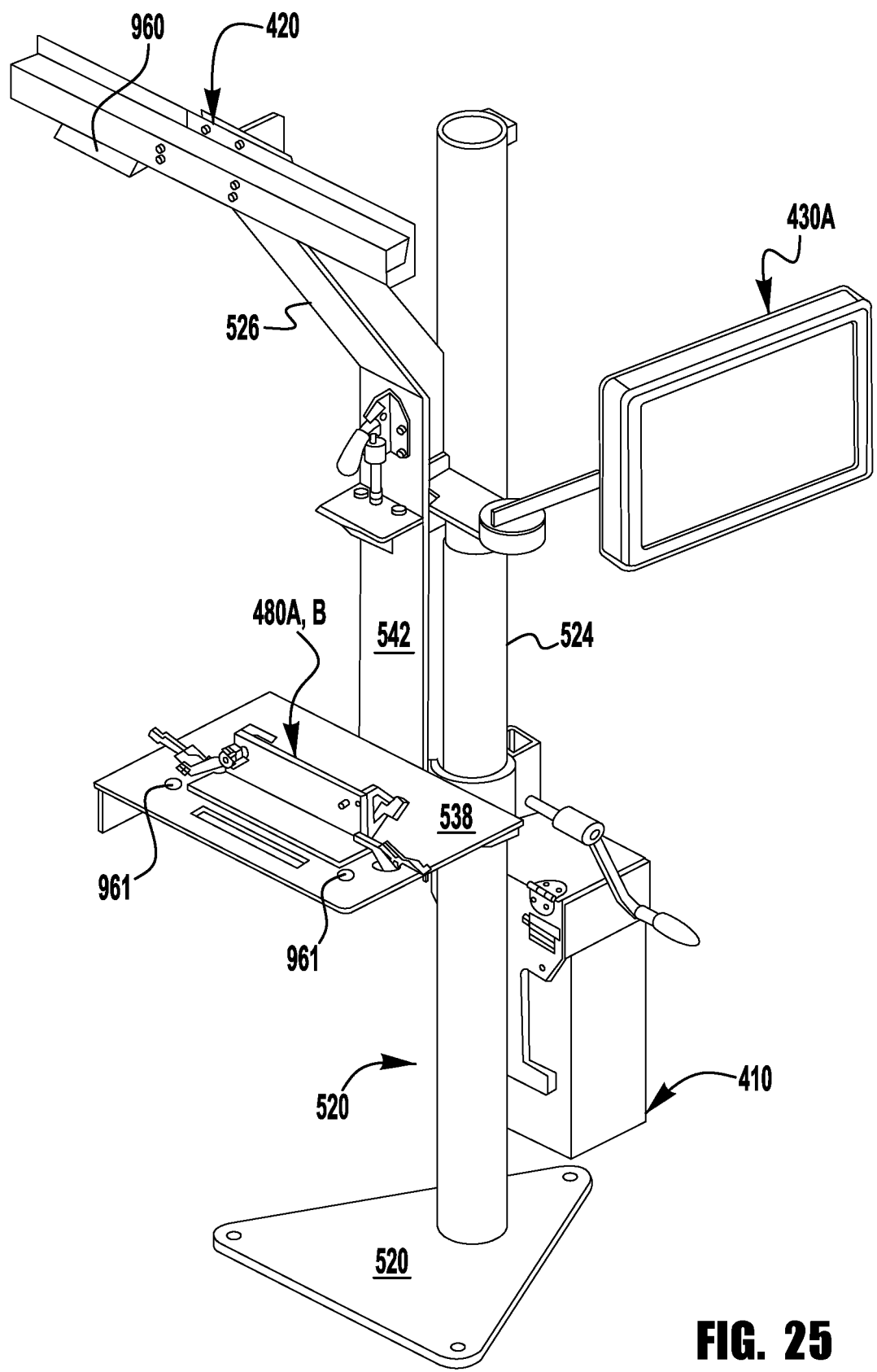
FIG. 25 illustrates a schematic view of another exemplary embodiment of a welding system.

In exemplary embodiments, the system 400 can include a coupon/workpiece recognition device. The coupon/workpiece recognition device can include a transmitter-receiver 960. As seen in FIG. 25, the transmitter-receiver 960 can be mounted to the tracking system support 526 (e.g. along with tracking cameras discussed above) of stand 520 or in another fixed location. Preferably, the transmitter-receiver 926 can be a known laser-radar type system that transmits laser light and senses the laser light after it has bounced off an object or objects. The transmitter-receiver 960 bounces the laser off the coupon/workpiece 480A, B and other objects on the table 538 of stand 520. As seen in FIG. 25, some of the other objects on table 538 include marker objects 961 which provide known reference points for both the coupon/workpiece recognition device and the tracking system of system 400 discussed above, which tracks welding helmet 440 and welding tool 460. Because the marker objects 961 are captured in both systems (the coupon/workpiece recognition device and the tracking system of system 400), the marker objects 961 serve as a common features that can calibrate the images captured by the coupon/workpiece recognition device discussed further below with the 3-D space of the welding environment 480.

Figure 26:
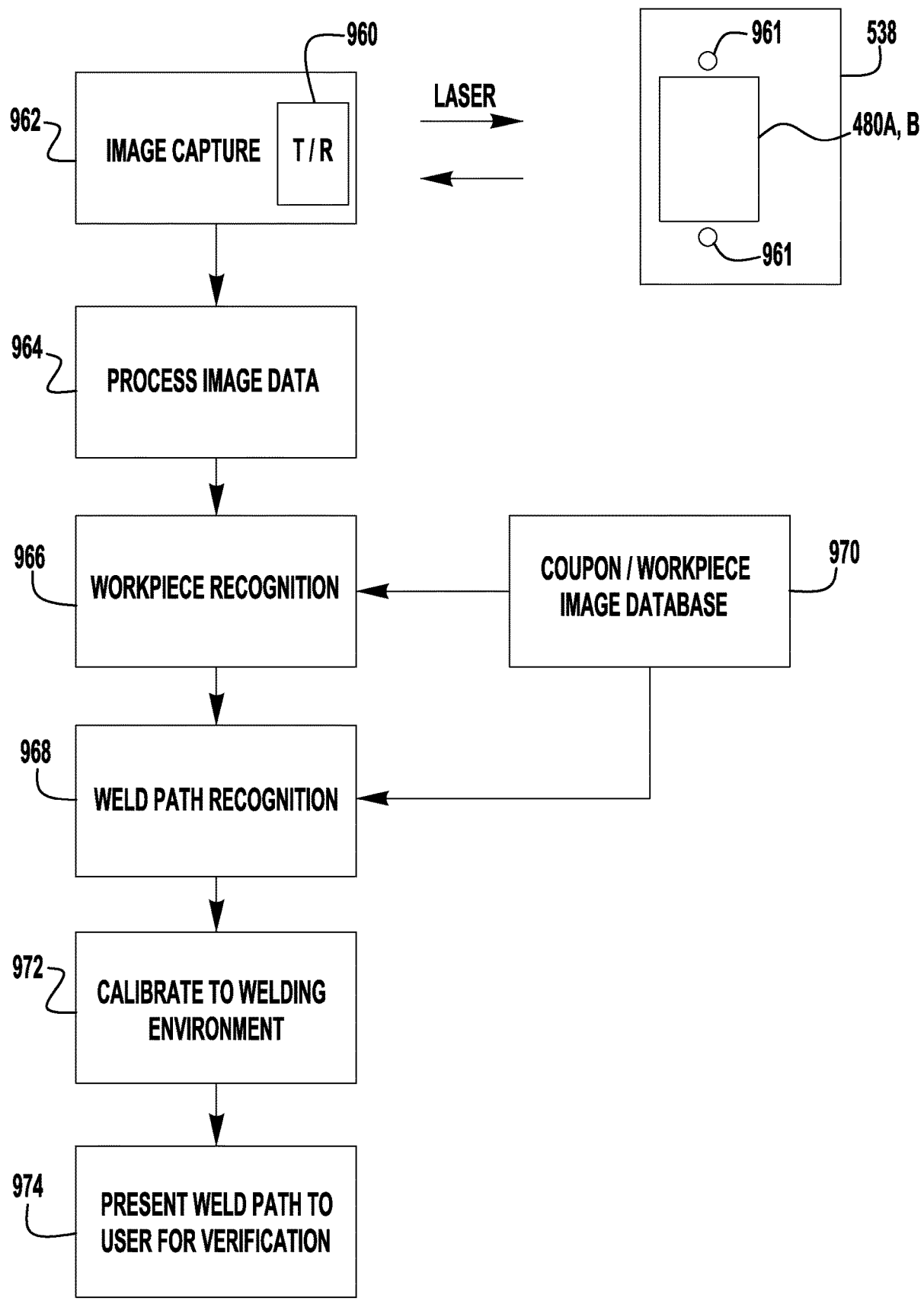
FIG. 26 illustrates a flow chart showing the flow of information in an exemplary embodiment of an object recognition device.

As seen in FIG. 26, a laser is used to scan the table 538 of stand 520, including coupon/workpiece 480A, B and marker objects 961. In block 962, the image of the table 538, including the objects on the workpiece is captured and the captured image is sent for further processing. In block 964, the captured image data is processed. The data processing can include recognizing different areas of the captured image such as the background and identifying potential objects of interest in the captured image. The processed image data is then sent for workpiece recognition. In block 966, the potential objects of interest identified in the processed image are compared against an image database that includes stored models of known welding coupons and workpieces, e.g., in CAD format (2-D or 3-D). The models can include different types of coupons and workpieces such as pipe, plate, T-joint, etc. In some embodiments, the models can include the custom parts, devices, components, etc. imported into the system, as discussed above. Once a type of coupon/workpiece is recognized, the identified workpiece image data is sent for further image processing in block 968 for recognition of the weld path. In block 968, the image with the identified workpiece is compared against the coupon/workpiece image data base again to identify the weld path associated with that workpiece, e.g., a fillet weld path, a lap weld path and a weld groove path. In addition to identifying the type of weld path, the length and orientation of the weld path is also determined based on the marker objects 961. In block 972, the image with the recognized coupon/workpiece and weld path is calibrated to the welding environment 480 based on the marker objects 961, which have known fixed orientation in the 3-D welding environment. Once calibrated to the welding environment 480 the image with the weld path is sent to the user via display 441 of the face-mounted display device 440A and/or the display 430A for confirmation. Preferably, the weld path is highlighted in some manner, e.g., by using a virtual welding object, etc., so that the user can confirm that the coupon/workpiece recognition device auto-calibrated the coupon/workpiece 480A, B properly. If the calibration was successful, the user can start the training on the coupon/workpiece 480A, B. If not, the user can have the coupon/workpiece recognition device re-start the calibration process. Preferably, the coupon/workpiece recognition device can auto-identify a range of welding joint types such as butt-type joint, orbital joint, T-joint, etc. and the weld paths associated with each joint type. While the above exemplary embodiments of an object recognition system were described using a laser device, other known recognition systems can be used such as those that use optical devices, ultrasonic devices, etc.

While the invention has been particularly shown and described with reference to exemplary embodiments thereof, the invention is not limited to these embodiments. It will be understood by those of ordinary skill in the art that various changes in form and details may be made therein without departing from the spirit and scope of the invention as defined by the above embodiments.

What is claimed is:

1. A system for aiding a user in at least one of welding, cutting, joining, and cladding operation, the system comprising:
    a welding tool for performing at least one of a real-world weld and a simulated weld on one of a coupon or workpiece;
    a see-through face-mounted display to allow the user to see a view of a welding environment including the one of a coupon or a workpiece, the face-mounted display having a combiner;
    a spatial tracker configured to track position, orientation and movement of the face-mounted display and the welding tool in 3-D space relative to the one of a coupon or a workpiece and determine 6-D data that corresponds to the tracking;
    a processor based subsystem configured to
        receive the 6-D data from the spatial tracker,
        generate at least one visual cue based on at least one of one or more performance parameters related to the 6-D data and one or more process parameters related to the at least one welding, cutting, joining, and cladding operation, wherein the at least one visual cue corresponds to at least one of a deposition rate and a frequency of TIG filler addition, and
        map the at least one visual cue to a respective location on the face-mounted display; and
    a projector configured to project the at least one visual cue onto the combiner of the face-mounted display such that the face-mounted display reflects and shows the at least one visual cue overlaid onto the view of the welding environment, wherein the combiner is configured to allow adjustment of an angle of reflection by the user, and
    wherein the at least one visual cue provides information to the user that aids in performing the at least one of a real-world weld and a simulated weld.

2. The system of claim 1, wherein the at least one visual cue further corresponds to at least one of aim, tool standoff, bead placement, work angle, travel angle, travel speed, weave, arc length, and contact tip to work distance (CTWD).

3. The system of claim 2, wherein at least one attribute of the at least one visual cue is changed based on whether the one or more performance parameters respectively associated with the at least one visual cue falls outside at least one of a target value and a target range for the performance parameter.

4. The system of claim 3, wherein the at least one attribute is at least one of a color, a shape, a size, an intensity, and a location on the face-mounted display of the at least one visual cue.

5. The system of claim 1, wherein the at least one visual cue is semitransparent to show an underlying view of the welding environment.

6. The system of claim 1, wherein the mapping is done such that the at least one visual cue is displayed at a fixed location on the face-mounted display that corresponds to at least one of a corner of the display, a top of the display, a side of the display, a top of the display and a middle of the display.

7. The system of claim 1, wherein the mapping is done such that the at least one visual cue is displayed in a same relative location with respect to the welding tool.

8. The system of claim 1, wherein the at least one visual cue identifies at least one of a start position and an end position of the at least one of a real-world weld and a simulated weld.

9. The system of claim 1, wherein the at least one visual cue provides an indication of a progress of the welding, cutting, joining, and cladding operation.

10. The system of claim 1, wherein the spatial tracker includes at least one camera mounted on the welder's helmet and the tracking is based on the at least one camera.

11. The system of claim 1, further comprising at least one speaker, and
wherein the processor based subsystem generates an audio cue based on at least one of the one or more performance parameters and the one or more process parameters and transmits the audio cues to the at least one speaker, and
wherein the audio cue is at least one of a tone, a buzzer and a voice alert.

12. The system of claim 1, wherein the spatial tracker is at least one of a camera based tracker, a magnetic-field based tracker, an accelerometer based tracker, a gyroscope based tracker, an optical tracker, an infrared tracker, an acoustic tracker, a laser tracker, a radio frequency tracker, and an inertial tracker.

13. The system of claim 1, further comprising:
at least one of a welding power supply, a wire feeder, and a hot wire power supply,
wherein the at least one visual cue provides an indication of at least one of a voltage and current of the welding power supply, a wire feed speed of the wire feeder, and at least one of a voltage and current of the hot wire power supply.

14. The system of claim 1, wherein the face-mounted display includes an auto-darkening lens.

15. The system of claim 1, wherein the processor based subsystem is configured to transmit to the face-mounted display media content related to at least one of instructional information on welding, information related to the user's performance and information related to a quality of the at least one of a real-world weld and a simulated weld.

16. The system of claim 1, wherein the processor based subsystem is configured to display menu items on the face-mounted display for configuring the system, and
wherein a navigation through the menu items is based on at least one of controlling the welding tool, audio commands, and eye tracing input.

17. A method for aiding a user in at least one of welding, cutting, joining, and cladding operation, the method comprising:
performing at least one of a real-world weld and a simulated weld on one of a coupon or workpiece using a welding tool;
providing a see-through face-mounted display having a combiner to provide the user a view of a welding environment including the one of a coupon or a workpiece;
tracking a position, an orientation, and a movement of the face-mounted display and the welding tool in 3-D space relative to the one of a coupon or a workpiece;
determining 6-D data that corresponds to the tracking;
generating at least one visual cue based on at least one of one or more performance parameters related to the 6-D data and one or more process parameters related to the at least one welding, cutting, joining, and cladding operation; and
mapping the at least one visual cue to a respective location on the face-mounted display, and
transmitting the at least one visual cue to the combiner of the face-mounted display such that the face-mounted display shows the at least one visual cue overlaid on the view of the welding environment,
wherein the at least one visual cue provides information to the user that aids in the performing of the at least one of a real-world weld and a simulated weld, and wherein the at least one visual cue corresponds to at least one of a deposition rate and a frequency of TIG filler addition.

18. The method of claim 17, wherein at least one attribute of the at least one visual cue is changed based on whether the one or more performance parameters respectively associated with the at least one visual cue falls outside at least one of a target value and a target range for the performance parameter.

19. The method of claim 18, wherein the at least one attribute is at least one of a color, a shape, a size, an intensity, and a location on the face-mounted display of the at least one visual cue.

20. The method of claim 17, wherein the at least one visual cue is semitransparent to show an underlying view of the welding environment.

21. The method of claim 17, wherein the mapping comprises displaying the at least one visual cue on the face-mounted display at a fixed location that corresponds to at least one of a corner of the display, a top of the display, a side of the display, a top of the display and a middle of the display.

22. The method of claim 17, wherein the mapping comprises displaying the at least one visual cue on the face-mounted display in a same relative location with respect to the welding tool.

23. The method of claim 17, wherein the at least one visual cue identifies at least one of a start position and an end position of the at least one of a real-world weld and a simulated weld.

24. The method of claim 17, wherein the at least one visual cue provides an indication of a progress of the welding, cutting, joining, and cladding operation.

25. The method of claim 17, wherein the tracking is based on at least one camera mounted on a welder's helmet.

26. The method of claim 17, further comprising:
generating an audio cue based on at least one of the one or more performance parameters and the one or more process parameters; and
transmitting the audio cue to at least one speaker,
wherein the audio cue is at least one of a tone, a buzzer and a voice alert.

27. The method of claim 17, wherein the tracking is based on at least one of a camera based tracker, a magnetic-field based tracker, an accelerometer based tracker, a gyroscope based tracker, an optical tracker, an infrared tracker, an acoustic tracker, a laser tracker, a radio frequency tracker, and an inertial tracker.

28. The method of claim 17, wherein the at least one visual cue provides an indication of at least one of a voltage and current of a welding power supply, a wire feed speed of a wire feeder, and at least one of a voltage and current of a hot wire power supply.

29. The method of claim 17, wherein the face-mounted display includes an auto-darkening lens.

30. The method of claim 17, further comprising:
transmitting to the face-mounted display media content related to at least one of instructional information on welding, information related to the user's performance and information related to a quality of the at least one of a real-world weld and a simulated weld.

31. The method of claim 17, further comprising:

displaying menu items on the face-mounted display related to configuration of a respective at least one of welding, cutting, joining, and cladding system; and navigating through the menu items based on at least one of controlling the welding tool, audio commands, and eye tracing input.

\* \* \* \* \*